(12) United States Patent
Shepard et al.

(10) Patent No.: US 7,462,605 B2
(45) Date of Patent: *Dec. 9, 2008

(54) PHOSPHORAMIDATE COMPOUNDS AND METHODS OF USE

(75) Inventors: H. Michael Shepard, Encinitas, CA (US); Andrew Rein Vaino, San Diego, CA (US); Danielle M. Lehsten, San Diego, CA (US)

(73) Assignee: Celmed Oncology (USA), Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/119,927

(22) Filed: Apr. 9, 2002

(65) Prior Publication Data

US 2003/0109697 A1 Jun. 12, 2003

(51) Int. Cl.
*A61K 31/70* (2006.01)
*C07H 19/10* (2006.01)

(52) U.S. Cl. ................ 514/51; 536/26.8

(58) Field of Classification Search ............ 514/45, 514/50, 51; 536/26.7, 26.8, 27.13, 28.59, 536/28.52, 28.54, 28.55
See application file for complete search history.

(56) References Cited

U.S. PATENT DOCUMENTS

| | | | |
|---|---|---|---|
| 3,852,266 A * | 12/1974 | Kiyanagi et al. | 536/28.55 |
| 4,247,544 A | 1/1981 | Bergstrom et al. | |
| 4,267,171 A | 5/1981 | Bergstrom et al. | |
| 4,542,210 A | 9/1985 | Sakata et al. | |
| 4,668,777 A | 5/1987 | Caruthers et al. | |
| 4,816,570 A | 3/1989 | Farquhar | |
| 4,948,882 A | 8/1990 | Ruth | |
| 4,963,263 A | 10/1990 | Kauvar | |
| 4,963,533 A | 10/1990 | De Clercq et al. | |
| 4,975,278 A | 12/1990 | Senter et al. | |
| 5,070,082 A * | 12/1991 | Murdock et al. | 514/105 |
| 5,077,282 A * | 12/1991 | Murdock et al. | 514/80 |
| 5,077,283 A * | 12/1991 | Murdock et al. | 514/94 |
| 5,085,983 A | 2/1992 | Scanlon | |
| 5,116,822 A | 5/1992 | De Clercq et al. | |
| 5,116,827 A * | 5/1992 | Murdock et al. | 514/82 |
| 5,133,866 A | 7/1992 | Kauvar | |
| 5,137,724 A | 8/1992 | Balzarini et al. | |
| 5,212,161 A * | 5/1993 | Moriniere et al. | 514/50 |
| 5,212,291 A * | 5/1993 | Murdock et al. | 536/6.4 |
| 5,217,869 A | 6/1993 | Kauvar | |
| 5,233,031 A | 8/1993 | Borch et al. | |
| 5,264,618 A | 11/1993 | Felgner et al. | |
| 5,274,162 A | 12/1993 | Glazier | |
| 5,300,425 A | 4/1994 | Kauvar | |
| 5,338,659 A | 8/1994 | Kauvar et al. | |
| 5,430,148 A | 7/1995 | Webber et al. | |
| 5,433,955 A | 7/1995 | Bredehorst et al. | |
| 5,457,187 A * | 10/1995 | Gmeiner et al. | 536/25.5 |
| 5,459,127 A | 10/1995 | Felgner et al. | |
| 5,502,037 A | 3/1996 | Kondratyev | |
| 5,516,631 A | 5/1996 | Frisch | |
| 5,521,161 A | 5/1996 | Malley et al. | |
| 5,527,900 A | 6/1996 | Balzarini et al. | |
| 5,556,942 A | 9/1996 | Kauvar et al. | |
| 5,596,018 A | 1/1997 | Baba et al. | |
| 5,616,564 A * | 4/1997 | Rapaport et al. | 514/44 |
| 5,627,165 A | 5/1997 | Glazier | |
| 5,643,893 A | 7/1997 | Benson et al. | |
| 5,645,988 A | 7/1997 | Vande Woude et al. | |
| 5,663,321 A | 9/1997 | Gmeiner et al. | |
| 5,733,896 A | 3/1998 | Holy et al. | |
| 5,798,340 A | 8/1998 | Bischofberger et al. | |
| 5,968,910 A | 10/1999 | Balzarini | |
| 5,981,507 A | 11/1999 | Josephson et al. | |
| 6,057,305 A | 5/2000 | Holy et al. | |
| 6,245,750 B1 * | 6/2001 | Shepard | 514/51 |
| 6,339,151 B1 * | 1/2002 | Shepard et al. | 536/26.8 |
| 6,495,553 B1 * | 12/2002 | Shepard | 514/256 |
| 6,589,941 B1 | 7/2003 | Fahrig et al. | |
| 6,599,499 B1 | 7/2003 | Rosen et al. | |
| 6,677,314 B2 | 1/2004 | Klecker et al. | |
| 6,677,315 B2 | 1/2004 | Klecker et al. | |
| 6,682,715 B2 | 1/2004 | Klecker et al. | |
| 6,683,045 B2 | 1/2004 | Klecker et al. | |

(Continued)

FOREIGN PATENT DOCUMENTS

DE 32 29 169 A1 2/1984

(Continued)

OTHER PUBLICATIONS

Firestone et al., "A Comparison of the Effects of Antitumor Agents Upon Normal Human Epidermal Keratinocytes and Human Squamous Cell Carcinoma," *Journal of Investigative Dermatology*, 94(5), 657-661 (May 1990).*

(Continued)

*Primary Examiner*—Shaojia Anna Jiang
*Assistant Examiner*—Lawrence E. Crane
(74) *Attorney, Agent, or Firm*—Antoinette F. Konski; Foley & Lardner LLP

(57) ABSTRACT

This invention provides compounds, compositions and methods for treating cancer, infectious disease, an autoimmune disorder or an inflammatory condition. Therapeutic compounds useful in the methods of this invention are 5'-phosphoramidatyl, 1,5-substituted pyrimidine compounds, derivatives, analogs and pharmaceutically acceptable salts thereof.

28 Claims, 10 Drawing Sheets

U.S. PATENT DOCUMENTS

| | | | |
|---|---|---|---|
| 6,683,061 B1 * | 1/2004 | Shepard et al. | 514/50 |
| 6,703,374 B1 | 3/2004 | Klecker et al. | |
| 7,138,388 B2 * | 11/2006 | Shepard | 514/80 |
| 2001/0016329 A1 * | 8/2001 | Shepard | 435/7.23 |
| 2001/0034440 A1 * | 10/2001 | Shepard et al. | 536/26.8 |
| 2002/0022001 A1 | 2/2002 | Klecker et al. | |
| 2002/0034473 A1 | 3/2002 | Klecker et al. | |
| 2002/0119094 A1 | 8/2002 | Klecker et al. | |
| 2002/0147175 A1 * | 10/2002 | Shepard et al. | 514/49 |
| 2002/0151519 A1 * | 10/2002 | Shepard et al. | 514/50 |
| 2002/0165199 A1 | 11/2002 | Klecker et al. | |
| 2003/0049201 A1 | 3/2003 | Klecker et al. | |
| 2003/0095921 A1 | 5/2003 | Klecker et al. | |

FOREIGN PATENT DOCUMENTS

| | | |
|---|---|---|
| EP | 0 095 294 A1 | 11/1983 |
| EP | 0 283 065 A1 | 9/1988 |
| EP | 0 311 107 A2 | 4/1989 |
| EP | 0 311 108 A2 | 4/1989 |
| EP | 0 316 592 | 5/1989 |
| GB | 982 776 | 2/1965 |
| GB | 982776 * | 2/1965 |
| RO | 88451 | 1/1986 |
| WO | WO 89/05817 | 6/1989 |
| WO | WO 90/03978 | 4/1990 |
| WO | WO 91/17424 | 11/1991 |
| WO | WO 92/19767 | 11/1992 |
| WO | WO 92/20344 | 11/1992 |
| WO | WO 94/03467 | 2/1994 |
| WO | WO 94/22483 | 10/1994 |
| WO | WO 94/22483 A2 * | 10/1994 |
| WO | WO 95/01806 | 1/1995 |
| WO | WO 95/08556 A1 * | 3/1995 |
| WO | WO 95/08558 | 3/1995 |
| WO | WO 95/09865 | 4/1995 |
| WO | WO 95/12678 | 5/1995 |
| WO | WO 96/03151 | 2/1996 |
| WO | WO 96/03151 A2 * | 2/1996 |
| WO | WO 96/07431 A1 * | 3/1996 |
| WO | WO 96/07413 | 4/1996 |
| WO | WO 96/10030 | 4/1996 |
| WO | WO 96/10300 A1 * | 4/1996 |
| WO | WO 96/29338 | 6/1996 |
| WO | WO 96/23506 | 8/1996 |
| WO | WO 96/33168 | 10/1996 |
| WO | WO 96/40088 | 12/1996 |
| WO | WO 96/40706 | 12/1996 |
| WO | WO 96/40708 A1 * | 12/1996 |
| WO | WO 96/40739 | 12/1996 |
| WO | WO 97/25342 | 7/1997 |
| WO | WO 97/28179 | 8/1997 |
| WO | WO 97/28179 A1 * | 8/1997 |
| WO | WO 97/49717 | 12/1997 |
| WO | WO 98/49177 | 11/1998 |
| WO | WO 99/06072 | 2/1999 |
| WO | WO 99/08110 | 2/1999 |
| WO | WO 99/20741 | 4/1999 |
| WO | WO 99/20741 A1 * | 4/1999 |
| WO | WO 99/23104 | 5/1999 |
| WO | WO 99/37753 | 7/1999 |
| WO | WO 00/18755 | 4/2000 |
| WO | WO 00/33888 | 6/2000 |
| WO | WO 01/07454 | 2/2001 |
| WO | WO 01/07454 A1 * | 2/2001 |
| WO | WO 01/83501 | 11/2001 |
| WO | WO 01/85749 | 11/2001 |
| WO | WO 2005/012327 A2 | 2/2005 |

OTHER PUBLICATIONS

Dagle et al., "Targeted Degradation of mRNA in *Xenopus* oocytes and Embryos Directed by Modified Oligonucleotides: Studies of An2 and Cyclin in Embryogenesis," *Nucleic Acids Research*, 18(16), 4751-4757 (Aug. 25, 1990).*

Hakimelahi et al., "Design, Synthesis, and Structure-Activity Relationship of Novel Dinucleotide Analogs as Agents Against Herpes and Human Immunodeficiency Viruses," *Journal of Medicinal Chemistry*, 38(23), 4648-4659 (Nov. 10, 1995).*

Naesens et al., "Anti-HIV Activity and Metabolism of Phosphoramidate Dericatives of D4T-MP with Variations in the Amino Acid Moiety," Poster Session 1, *The Tenth International Conference on Antiviral Research*, Hotel Nikko, Atlanta, GA, Apr. 6-11, 1997; published in *Antiviral Research*, 34(2), p. A54 (Abstract 40), (Apr. 1997).*

Evrard et al., "An in vitro Nucleoside Analog Screening Method for Cancer Gene Therapy," *Cell Biology and Toxicology*, 12, 345-350 (1996).*

Berkow et al. (eds.), *The Merck Manual of Diagnosis and Therapy, 16th Ed.*, Merck & Co., Rahway, NJ, May 1992, only page 1278 supplied.*

Morrison & Boyd (eds.), *Organic Chemistry*, Allyn & Bacon, Inc., Boston, MA, 1973, onlyh pp. 1170-1180 supplied.*

L. B. Townsend (ed.), *Chemistry of Nucleosides and Nucleotides*, vol. 3, Plenum Press, New York, NY, 1974, only Table of Contents, Bibliograhy pp. 529-535, and Index pp. 537-552 supplied.*

*The American Heritage College Dictionary*, Third Edition, Houghton Mifflin Co., New York, NY, 1997, only p. 668 supplied.*

Smith et al., "Second Passage Human Breast Cancer Cells,"*Cancer Research*, 50(10), 2943-2948 (May 1990).*

(RA) Smith et al., "Second Passage Human Breast Cancer Cells," Cancer Research, 50(10), 2943-2948 (May 1990).*

(RA) Smith et al., "Second Passage Human Breast Cancer Cells," □□Cancer Research, 50(10), 2943-2948 (May 1990).*

Abraham et al., "Synthesis and biological activity of aromatic amino acid phosphoramidates of 5-fluoro-2'-deoxyuridine and 1-β-arabinofuranosylcytosine: Evidence of phosphoramidase activity" *J. Med. Chem.* 39:4569-4575 (1996).

Akdas et al., "Glutathione S-transferase and multidrug-resistant phenotype in transitional cell carcinoma of the bladder" *Eur. Urol.* 29:483-486 (1996).

Almasan et al. "Deficiency of retinoblastoma protein leads to inappropriate S-phase entry, activation of E2F-responsive genes, and apoptosis" *PNAS*, USA 92:5436-5540 (Jun. 1995).

Almasan et al., "Genetic instability as a consequence of inappropriate entry into and progression through S-phase" *Can. Metastasis Rev.* 14:59-73 (1995).

Andersen et al., "Detection of c-erbb-2 related protein in sera from breast cancer patients" *Acta Oncol.* 34(4):499-504 (1995).

Anglada et al., "N,N'-cyclization of carbodiimides with 2-(bromomethyl)acrylic acid. A direct entry to the system 5-methylene-6H-pyrimidine-2,4-dione, a new class of thymine analogues" *J. Heterocyclic Chem.* 33:1259-1270 (Jul.-Aug. 1996).

Antelman et al., "Inhibition of tumor cell proliferation in vitro and in vivo by exogenous p110RB, the retinoblastoma tumor suppressor protein" *Oncogene* 10:697-704 (1995).

Aoki et al., "Inhibition of the p53 tumor suppressor gene results in growth of human aortic vascular smooth muscle cells. Potential role of p53 in regulation of vascular smooth muscle cell growth" *Hypertension* 34(2):192-200 (Aug. 1999).

Asakura et al., "Cerium(IV) catalyzed iodination at C5 of uracil nucleosides" *Tetrahedron Lett.* 29(23):2855-2858 (1988).

Asakura et al., "Cerium(IV)-mediated halogenation at C-5 of uracil derivatives" *J. Org. Chem.* 55:4929-4933 (1990).

Aupperle et al., "Regulation of synoviocyte proliferation, apoptosis, and invasion by the p53 tumor suppressor gene" *Am. J. Pathol.* 152(4):1091-8 (Apr. 1998).

Ayisi et al. "Comparison of the antiviral effects of 5-methoxymethyldeoxyuridine-5'-monophosphate with adenine arabinoside-5'-monophosphate" *Antivirals Res.* 3:161-174 (1983).

Bajetta et al. "A pilot safety study of capecitabine, a new oral fluoropyrimidine, in patients with advanced neoplastic disease" *Tumor* 82:450-452 (1996).

Balzarini et al., "Incorporation of 5-substituted pyrimidine nucleoside analogues into DNA of a thymidylate synthetase-deficient murine FM3A carcinoma cell line" *Meth. Find. Exptl. Clin. Pharmacol.* 7(1):19-28 (1985).

Balzarini et al., "Thymidylate synthase is the principal target enzyme for the cytostatic activity of (E)-5-(2-bromovinyl)-2'-deoxyuridine against murine mammary carcinoma (FM3A) cells transformed with the herpes simplex virus type 1 or type 2 thymidine kinase gene" *Mol. Pharmacol.* 32:410-416 (1987).

Balzarini et al., "Differential mechanism of cytostatic effect of (E)-5-(2-bromovinyl)-2'-deoxyuridine, 9-(1,3-dihydroxy-2-propoxymethyl)guanine, and other antiherpetic drugs on tumor cells transfected by the thymidine kinase gene of herpes simplex virus type 1 or type 2" *J. Biol. Chem.* 268(9):6332-6337 (1993).

Balzarini et al. "The cytostatic activity of 5-(1-azidovinyl)-2'-deoxyuridine (AzVDU) against herpes simples virus thymidine kinase gene-transfected FM3A cells is due to inhibition of thymidylate synthase and enhanced by UV light ($\lambda$=254 nm) exposure" *FEBS Lett.* 373:41-44 (1995).

Balzarini et al., "Anti-HIV and anti-HBV activity and resistance profile of 2', 3'-dideoxy-3'-thiacytidine (3TC) and its arylphosphoramidate derivative CF 1109" *Biochem. Biophys. Res. Commun.* 225:363-369 (1996).

Balzarini et al. "Mechanism of anti-HIV action of masked alaninyl d4T-MP derivatives" *PNAS USA* 93:7295-7299 (Jul. 1996).

Balzarini et al., "Conversion of 2',3'-dideoxyadenosine (dda) and 2',3'-didehydro-2',3'-dideoxyadenosine (d4A) to their corresponding aryloxyphosphoramidate derivatives markedly potentiates their activity against human immunodeficiency virus and hepatitis B virus" *FEBS Lett.* 410:324-328 (1997).

Banerjee et al., "Molecular mechanisms of resistance to antifolates, a review" *Acta Biochimica Polonica* 42(4):457-464 (1995).

Banerjee et al., "Role of E2F-1 in chemosensitivity" *Can. Res.* 58:4292-4296 (Oct. 1998).

Barbato et al., "Synthesis of bridged pyrimidine nucleosides and triazo [4, 3-c] pyrimidine nucleoside analogues" *Nucleosides & Nucleotides* 8(4):515-528 (1989).

Barbour et al., "A naturally occurring tyrosine to histidine replacement at residue 33 of human thymidylate synthase confers resistance to 5-fluoro-2'-deoxyuridine in mammalian and bacterial cells" *Mol. Pharmacol.* 42:242-248 (1992).

Barr, "Inhibition of thymidylate synthetase by 5-alkynyl-2'-deoxyuridylates" *J. Med. Chem.* 24(12):1385-1388 (1981).

Barr et al., "Thymidylate synthetase-catalyzed conversions of E-5-(2-bromovinyl)-2'-deoxyuridylate" *J. Biol. Chem.* 258(22):13627-13631 (1983).

Barr et al., "Reaction of 5-ethynyl-2'-deoxyuridylate with thiols and thymidylate synthetase" *Biochem.* 22:1696-1703 (1983).

Barret et al., "Trapping of the C5 methylene intermiediate in thymidylate synthase" *J. Am. Chem. Soc.* 120:449-450 (1998).

Bathe et al. "Increased thymidylate synthase gene expression in liver metastases from colorectal carcinoma: implications for chemotherapeutic options and survival" *Cancer J. Sci. Am.* 5(1):34-40 (1999).

Benzaria et al., "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability" *J. Med. Chem.* 39:4958-4965 (1996).

Bergstrom et al., "C-5-substituted pyrimidine nucleosides. 3. Reaction of allylic chlorides, alcohols, and acetates with pyrimidine nucleoside derived organopalladium intermediates" *J. Org. Chem.* 46(7):1432-1441 (1981).

Bergstrom et al., "Synthesis of (E)-5-(3,3,3-trifluoro-1-propenyl)-2'-deoxyuridine and related analogues: potent and unusually selective antiviral activity of (E)-5-(3,3,3-trifluoro-1-propenyl)-2'-deoxyuridine against herpes simplex virus type 1" *J. Med. Chem.* 27:279-284 (1984).

Berkow et al. (eds), *The Merck Manual of Diagnosis and Therapy*, 16th ed., Merck & Co., Rahway, NJ, May 1992, only page 1278 supplied.

Bertino et al., "Resistance mechanisms to methotrexate in tumors" *Stem Cells* 14:5-9 (1996).

Bible et al. "Cytotoxic synergy between flavopiridol (NSC 649890, L86-8275) and various antineoplastic agents: the importance of sequence of administration" *Cancer Res.* 57(16):3375-80 (Aug. 15, 1997).

Bigge et al., "Palladium-catalyzed coupling reactions of uracil nucleosides and nucleotides" *J. Am. Chem. Soc.* 102(6):2033-2038 (1980).

Bosslet et al., "A novel one-step tumor-selective prodrug activation system" *Tumor Targeting* 1:45-50 (1995).

Bosslet et al., "Elucidation of the mechanism enabling tumor selective prodrug monotherapy" *Can. Res.* 58:1195-1201 (1998).

Brison, "Gene amplification and tumor progression" *Biochem. Biophys. Acta* 1155:25-41 (1993).

Carl et al., "Protease-activated 'prodrugs' for cancer chemotherapy" *PNAS USA* 77(4):2224-2228 (1980).

Carreras et al., "The catalytic mechanism and structure of thymidylate synthase" *Annu. Rev. Biochem.* 64:721-762 (1995).

Carson and Haneji, "Fighting arthritis with a senescence gene" *Nature Medicine* 5(7):731-732 (Jul. 1999).

Carter et al., "Humanization of an anti-p185$^{HER2}$ antibody for human cancer therapy" *PNAS USA* 89:4285-4289 (May 1992).

Cass et al. "Recent advances in the molecular biology of nucleoside transporters of mammalian cells" *Biochem. Cell Biol.* 76(5):761-770 (1998).

Catucci et al. "Development and significance of the HIV-1 reverse transcriptase M184V mutation during combination therapy with lamivudine, zidovudine, and protease inhibitors" *J. Acquir. Immune Defic. Syndr.* 21:203-208 (1999), (Jul. 1, 1999).

Cava et al., "Thionation reactions of lawesson's reagents" *Tetrahedron* 41(22):5061-5087 (1985).

Chakravarty et al., "Plasmin-activated prodrugs for cancer chemotherapy. 2. Synthesis and biological activity of peptidyl derivatives of doxorubicin" *J. Med. Chem.* 26(5):638-644 (1983).

Chaudhuri et al., "Very high affinity DNA recognition by bicyclic and cross-linked oligonucleotides" *J. Am. Chem. Soc.* 117:10434-10442 (1995).

Chen et al., "Sensitization of human breast cancer cells to cyclophosphamide and ifosfamide by transfer of a liver cyctochrome P450 gene" *Can. Res.* 56:1331-1340 (Mar. 15, 1996).

Cho et al., "(E)-5-(3-oxopropen-1-yl)-2'-deoxyuridine and (E)-5-(3-oxopropen-1-yl)-2',3'-dideoxyuridine; new antiviral agents: Syntheses and biological activity" *Tetrahedron Lett.* 35(8):1149-1152 (1994).

Chou and Talalay, "Quantitative analysis of dose-effect relationships: the combined effects of multiple drugs or enzyme inhibitors" *Adv. Enzyme Regul.* 22:27-55 (1984).

Clarke, "Animal models of breast cancer: Their diversity and role in biomedical research" *Breast Can. Res. Treat.* 39:1-6 (1996).

Clayman, "The current status of gene therapy" *Semin Oncol* 27(4 Suppl 8):39-43 (Aug. 2000).

Coderre et al. "Mechanism of action of 2',5-difluoro-1-arabinosyluracil" *J. Med. Chem.* 26(8):1149-1152 (1983).

Colacino, "Mechanisms for the anti-hepatitis B virus activity and mitochondrial toxicity of fialuridine (FIAU)" *Antiviral Res.* 29:125-139 (1996).

Collins et al. "Suicide prodrugs activated by Thymidylate synthase: Rationale for treatment and noninvasive imaging of tumors with deoxyuridine analogues" *Clin. Cancer Res.* 5:1976-1981 (Aug. 1999).

Connors, "Prodrugs in cancer chemotherapy" *Xenobiotica* 16(10/11):975-988 (1986).

Connors, et al., "Prodrugs in cancer chemotherapy" *Stem Cells* 13:501-511 (1995).

Connors, "Is there a future for cancer chemotherapy?" *Annals Oncol.* 7:445-452 (1996).

Copur et al., "Thymidylate synthase gene amplification in human colon cancer cell lines resistant to 5-flouorouracil" *Biochem. Pharmacol.* 49(10):1419-1426 (1995).

Cordon-Cardo and Prives, "At the crossroads of inflammation and tumorigenesis" *J. Exp. Med.* 190(10):1367-1370 (Nov. 15, 1999).

Costi et al. "Phthalein derivatives as a new tool for selectivity in thymidylate synthase inhibition" *J. Med. Chem.* 42(12):2112-2124 (1999) (Web published May 29, 1999).

Crisp, "Synthesis of 5-alkenyl-2'-deoxyuridines via organostannanes" *Synthetic Commun.* 19(11&12):2117-2123 (1989).

Curt, "Cancer drug development: new targets for cancer treatment" *Oncologist* 1(3):II-III (1996).

Dagle, et al., "Targeted degradation of mRNA in *Xenopus* oocytes and embryos directed by modified oligonucleotides: Studies of An2 and Cyclin in embryogenesis" *Nucleic Acids Research* 18(16):4751-4757 (Aug. 25, 2000).

Dale et al., "The synthesis and enzymatic polymerization of nucleotides containing mercury: Potential tools for nucleic acid sequencing and structural analysis" *PNAS USA* 70(8):2238-2242 (Aug. 1973).

Davisson et al., "Expression of human thymidylate synthase in *Escherichia coli*" *J. Biol. Chem.* 264(16):9145-9148 (1989).

Davisson et al. "Expression of human thymidylate synthase in *Escherichia coli*. (Additions and corrections)" *J. Biol. Chem.* 269(48):30740 (1994).

DeClercq et al. "Antiviral Activity of Novel Deoxyuridine Derivatives" *Current Chemotherapy: Proceedings of the International Congress of Chemotherapy* 1:352-354 (Sep. 18, 1978).

DeClercq et al., "Nucleic acid related compounds. 40. Synthesis and biological activities of 5-alkynylauracil nucleosides" *J. Med. Chem.* 26:661-666 (1983).

DeClercq, "Antiviral Activity Spectrum and Target of Action of Different Classes of Nucleoside Analogues" *Nucleosides & Nucleosides* 13(6&7):1271-1295 (1994).

DeClercq, "In search of a selective antiviral chemotherapy" *Clin. Micro. Review* 10(4):674-693 (Oct. 1997).

DiCiommo et al., "Retinoblastoma: the disease, gene and protein provide critical leads to understand cancer" *Seminars in Cancer Biology* 10:255-269 (2000).

Dicker et al., "Methotrexate resistance in an in vivo mouse tumor due to a non-active-site dihydrofolate reductase mutation" *PNAS USA* 90:11797-11801 (1993).

Dirven et al., "The role of human glutathione S-transferase isoenzymes in the formation of glutathione conjugates of the alkylating cytostatic drug thiotepa" *Can. Res.* 55:1701-1706 (1995).

Dorr et al. (Eds.) "PALA" in: *Cancer Chemotherapy Handbook*, 2nd Ed., Appleton & Lange, Norwalk, Connecticut, pp. 768-773 (1994).

Drake et al., "Resistance to Tomudex (ZD1694): Multifactorial in Human Breast and Colon Carcinoma Cell Lines" *Biochem. Pharmacol.* 51(10):1349-1355 (1996).

Dunn et al., "Solution of the conformation and alignment tensors for the binding of trimethoprim and its analogs to dihydrofolate reductase: 3D-quantitative structure-activity relationship study using molecular shape analysis, 3-way partial least-squares regression, and 3-way factor analysis" *J. Med. Chem.* 39:4825-4832 (1996).

Dyer et al., "Nucleic Acids Chemistry: Improved and new synthetic procedures, methods, and techniques" Townsend, L. B. & Tipson, R. S., eds. (Wiley-Interscience, New York, NY) vol. 4:79-83 (1991).

Eccles et al., "Significance of the c-*erB* family of receptor tyrosine kinases in metastatic cancer and their potential as targets for immunotherapy" *Invasion Metastasis* 14(1-6):337-348 (1994-1995).

Eisenbrand et al., "An approach towards more selective anticancer agents" *J. Synthetic Organic Chem.* 10:1246-1258 (1996).

Elliott et al., "Randomised double-blind comparision of chimeric monoclonal antibody to tumour necrosis factor α (cA2) versus placebo in rheumatoid arthritis" *Lancet* 344(8930):1105-1110.

Evard et al. "An in vitro nucleoside analog screening method for cancer gene therapy" *Chem. Abstracts* 126:Abstract No. 26514 (1996).

Evard et al. "An in vitro nucleoside analog screening method for cancer gene therapy" *Cell Biology and Toxicology* 12:345-350 (1996).

Farquhar et al., "Synthesis and antitumor evaluation of bis[(pivaloyloxy)methyl] 2'-deoxy-5-fluorouridine 5'-monophosphate (FdUMP): A strategy to introduce nucleotides into cells" *J. Med. Chem.* 37:3902-3909 (1994).

Farquhar et al., "5'-[4-pivaloyloxy)-1,3,2-dioxaphosphorinan-2-yl]-2'-deoxy-5-fluorouridine: A membrane-permeating prodrug of 5-fluoro-2'-deoxyuridylic acid (FdUMP)" *J. Med. Chem.* 38:488-495 (1994).

Feldmann et al., "Biological insights from clinical trials with anti-TNF therapy" *Springer Semin. Immunopathol.* 20(1-2):211-228 (1998).

Felip et al., "Overexpression of c-*erbB*-2 in epithelial ovarian cancer" *Cancer* 75(8):2147-2152 (1995).

Felmingham and Washington, "Trends in the antimicrobial susceptibility of bacterial respiratory tract pathogens—findings of the Alexander Project 1992-1996" *J. Chemother.* 11(Suppl 1):5-21 (1999).

Finch et al., "Radiation Injury" In: *Harrison's Principles of Internal Medicine*, 12th edition: McGraw-Hill, Inc., New York, NY, pp. 2204-2208 (1991).

Finer-Moore et al., "Refined structures of substrate-bound and phosphate-bound thymidylate synthase from *Lactobacillus casei*" *J. Mol. Biol.* 232:1101-1116 (1993).

Finer-Moore et al., "Crystal structure of thymidylate synthase from T4 phage: Component of a deoxynucleoside triphophate-synthesizing complex" *Biochem.* 33:15459-15468 (1994).

Firestone et al., "A comparison of the effects of antitumor agents upon normal human epidermal kerartinocytes and human squamous cell carcinoma" *J. of Investigative Dermatology* 94(5):657-661 (May 1990).

Firestone et al., "A comparison of the effects of antitumor agents upon normal human epidermal kerartinocytes and human squamous cell carcinoma" *Chem Abstracts* 113:Abstract No. 254 (1990).

Freed et al., "Evidence for acyloxymethyl esters of pyrimidine 5'-deoxyribonucleotides as extracellular sources of active 5'-deoxyribonucleotides in cultured cells" *Biochem. Pharnacol.* 38(19):3193-3198 (1989).

Fries et al., "Synthesis and biological evaluation of 5-fluoro-2'-deoxyuridine phosphoramidate analogs" *J. Med. Chem.* 38(14):2672-2680 (1995).

Garrett et al., "Thymidylate synthetase. Catalysis of dehalogenation of 5-bromo-and 5-iodo-2'-deoxyuridylate" *Biochem.* 18(13):2798-2804 (1979).

Goldberg et al. "Novel cell imaging techniques show induction of apoptosis and proliferation in mesothelial cells by asbestos" *Am. J. Respir. Cell.Mol. Biol.* 17:265-271 (1997).

Goldstein et al., "Genetic aspects of disease" In: *Harrison's Principles of Internal Medicine*, 12th edition: McGraw-Hill, Inc., New York, NY, pp. 21-76 (1991).

Goodwin et al., "Incorporation of alkylthiol chains at C-5 of deoxyuridine" *Tetrahedron Lett.* 34(35):5549-5552 (1993).

Gottesman et al., "Genetic analysis of the multidrug transporter" *Ann. Rev. Gen.* 29:607-649 (1995).

Graham et al., "DNA duplexes stabilized by modified monomer residues: synthesis and stability" *J. Chem. Soc. Perkin Trans.* 1:1131-1138 (1998).

Grem, "Biochemical modulation of fluorouracil by dipyridamole: preclinical and clinical experience" *Semin Oncol.* 19(2 Suppl 3):56-65 (Apr. 1992).

Gros et al., "Isolation and expression of a complementary DNA that confers multidrug resistance" *Nature* 323:728-731 (1986).

Gros et al., "Mammalian multidrug resistance gene: Complete cDNA sequence indicates strong homology to bacerial transport proteins" *Cell* 47:371-380 (1986).

Gros et al., "Isolation and characterization of DNA sequences amplified in multidrug-resistant hamster cells" *PNAS USA* 83:337-341 (1986).

Gudkov et al., "Cloning and characterization of DNA sequences amplified in multidrug-resistant djungarian hamster and mouse cells" *Somat. Cell Mol. Genet.* 13(6):609-619 (1987).

Guevara et al., "The absence of p53 accelerates atherosclerosis by increasing cell proliferation in vivo" *Nat Med* 5(3):335-9 (Mar. 1999).

Hakimelahi et al., "Design, synthesis, and structure-activity relationship of novel dinucleotide analogs as agents against herpes and human immunodeficiency viruses" *Journal of Medicinal Chemistry* 38(23):4648-4659 (Nov. 10, 1995).

Han et al., "Dominant-negative p53 mutations in rheumatoid arthritis" *Arthritis Rheum* 42(6):1088-92 (Jun. 1999).

Hardy et al., "Atomic structure of thymidylate synthase: Target for rational drug design" *Science* 235:448-455 (1987).

Harris et al., "Adenovirus-mediated p53 gene transfer inhibits growth of human tumor cells expressing mutant p53 protein" *Can. Gene Ther.* 3(2):121-130 (1996).

Hashimoto et al., "Simple separation of tritiated water and [3H] deoxyuridine from [5-3H] deoxyuridine 5'-monophosphate in the thymidylate synthase assay" *Anal. Biochem.* 167:340-346 (1987).

Hengstschläger et al., "The role of p16 in the E2F-dependent thymidine kinase regulation" *Oncogene* 12:1635-1643 (1996).

Hobbs, "Palladium-catalyzed synthesis of alkynylamino nucleosides. A universal linker for nucleic acids" *J. Org. Chem.* 54:3420-3422 (1989).

Holy et al., "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base" *J. Med. Chem.* 42(12):2064-2086 (Web Published May 15, 1999).

Hong et al. "Profiling the downstream genes of tumor suppressor *PTEN* in lung cancer cells by complementary DNA microarray" *Am. J. Respir. Cell. Mol. Biol.* 23(3):355-63 (2000).

Hooker et al. "An in vivo mutation from leucine to tryptophan at position 210 in human Immunodeficiency virus type 1 reverse transcriptase contributes to high-level resistance to 3'-azido-3'-deoxythymidine" *J. Virol.* 70(10):8010-8018 (Nov. 1996).

Horikoshi et al., "Quantitation of thymidylate synthase, dihydrofloate reductase, and DT-diaphorase gene expression in human tumors using the polymerase chain reaction" *Can. Res.* 52:108-116 (1992).

Horn et al., "Fialuridine is phosphorylated and inhibits DNA synthesis in isolated rat hepatic mitochondria" *Antiviral Res.* 34:71-74 (1997).

Hostetler et al., "Enhanced oral absorption and antiviral activity of 1-o-octadecyl-sn-glycero-3-phospho-acyclovir and related compounds in hepatitis B virus infection, in vitro" *Biochem. Pharmacol.* 53:1815-1822 (1997).

Houze et al., "Detection of thymidylate synthase gene expression levels in formalin-fixed paraffin embedded tissue by semiquantitative, nonradioactive reverse transcriptase polymerase chain reaction" *Tumor Biol.* 18:53-68 (1997).

Hsiao et al., "Synthesis of 5'-thymidinyl bis(1-aziridinyl) phosphinates as antineoplastic agents" *J. Med. Chem.* 24:887-889 (1981).

Huang et al., "Active site general catalysts are not necessary for some proton transfer reactions of thymidylate synthase" *Biochem.* 36:1869-1873 (1997).

Hudson et al., "A proinflammatory cytokine inhibits p53 tumor suppressor activity" *J. Exp. Med.* 190(10):1375-1382 (Nov. 15, 1999).

Hudziak et al., "Selection for transformation and met protooncogene amplification in NIH 3T3 fibroblasts using tumor necrosis factor I" *Cell Growth & Differentiation* 1:129-134 (1990).

Hudziak et al., "Amplified expression of the HER2/ERBB2 oncogene induces resistance to tumor necrosis factor α in NIH 3T3 cells" *PNAS USA* 85:5102-5106 (Jul. 1988).

Husak et al. "Pseudotumour of the tongue caused by herpes simplexx virus type 2 in a HIV-1 infected immunosuppressed patient" *British J. Dermatol.* 139:118-121 (1998).

Iglesias et al., "Human papillomavirus type 16 E7 protein sensitizes cervical keratinocytes to apoptosis and release of interleukin-1α" *Oncogene* 17:1195-1205 (1998).

Imai et al., "Studies on phosphorylation. IV. Selective phosphorylation of the primary hydroxyl group in nucleosides" *J. Org. Chem.* 34(6):1547-1550 (1969).

Inazuka et al. "Analysis of p53 tumour suppressor gene somatic mutations in rheumatoid arthritis synovium" *Rheumatology (Oxford)* 39(3):262-6 (2000).

Jackman, "Folate-based thymidylate synthase inhibitors as anticancer drugs" *Ann. Oncol.* 6(9):871-881 (1995).

Jackman et al., "Quinazoline-based thymidylate synthase inhibitors: Relationship between structural modifications and polyglutamation" *Anti-Cancer Drug Design* 10:573-589 (1995).

Jin et al., "BRCA1 activation of the *GADD45* promoter" *Oncogene* 19:4050-7 (2000).

Johnston et al., "Production and characterization of monoclonal antibodies that localize human thymidylate synthase in the cytoplasm of human cells and tissue" *Can. Res.* 51:6668-6676 (1991).

Johnston, "The role of thymidylate synthase expression in prognosis and outcome of adjuvant chemotherapy in patients with rectal cancer" *J. Clin. Oncol.* 12(12):2640-2647 (1994).

Johnston et al. "Thymidylate synthase gene and protein expression correlate and are associated with response to 5-fluorouracil in human colorectal and gastric tumors" *Cancer Res.* 55:1407-1412 (1995).

Jones and Mann, "New methods of synthesis of β-aminoethylpyrazoles" *J. Am. Cancer Soc.* 75: 4048-4052 (Aug. 20, 1953).

Kamb et al., "Cyclin-dependent kinase inhibitors and human cancer" *Curr. Top. Microbiol. Immunol.* 227:139-148 (1998).

Kashani-Sabet et al., "Detection of drug resistance in human tumors by in vitro enzymatic amplification" *Can. Res.* 48:5775-5778 (Oct. 15, 1988).

Katki et al. "Prodrugs activated by thymidylate synthase: Treatment of tumors with deoxyuridine analogs" *Proc. Amer. Assoc. Cancer Res.* 39, Abstract No. 1275 (Mar. 1998).

Kitasato et al. "Absence of p53 mutation in Japanese patients with rheumatoid arthritis: comment on the article by Han et al." *Arthritis Rheum.* 43(2):469-70 (2000).

Klecker et al., "Toxicity, metabolism, DNA incorporation with lack of repair, and lactate production for 1-(2'-fluoro-2'-deoxy-J-D-arabinofuranosyl)-5-iodouracil in U-937 and MOLT-4 cells" *Mol. Pharmacol.* 46:1204-1209 (1994).

Knighton et al., "Structure and kinetic channelling in bifunctional dihydrofolate reductase-thymidylate synthase" *Nature Struct. Biol.* 1(3):186-194 (1994).

Knudson, "Antioncogenes and human cancer" *Proc. Natl. Acad. Sci. USA* 90(23):10914-21 (Dec. 1993).

Kobayashi et al., "Effect of hammerhead ribozyme against human thymidylate synthase on the cytotoxicity of thymidylate synthase inhibitors" *Jpn. J. Can. Res.* 86:1014-1018 (Nov. 1995).

Kodama et al. "Evaluation of antiherpetic compounds using a gastric cancer cell line: Pronounced activity of BVDU against herpes simplex virus replication" *Microbiol. Immunol.* 40(5):359-363 (1996).

Komaki et al. "Difference in thymidylate synthetase activity in involved nodes compared with primary tumor in breast cancer patients" *Breast Cancer Res. Treat.* 35(2):157-162 (1995).

Krajewska et al., "Pyrimidine ribonucleoside phosphorylase activity VS 5- and/or 6-substituted uracil and uridine analogues, including conformational aspects" *Biochem. Pharmacol.* 31(6):1097-1102 (1982).

Kullmann et al., "Analysis of the p53 tumor suppressor gene in rheumatoid arthritis synovial fibroblasts" *Arthritis Rheum.* 42(8):1594-600 (Aug. 1999).

Kumar et al., "Synthesis and biological evaluation of some cyclic phosphoramidate nucleoside derivatives" *J. Med. Chem.* 33(9):2368-2735 (1990).

Kundu, "Synthesis and biological activities of [E]-5-(2-acylvinyl) uracils" *Eur. J. Med. Chem.* 28:473-479 (1993).

Kuroboshi et al., "A facile synthesis of difluoromethylene compounds by oxidative fluorodesulfurization of dithioacetals using tetrabutylammonium dihydrogentrifluoride and N-halo compounds" *Synlett* pp. 909-910 (1991).

Kuroboshi et al., "A facile synthesis of I,I-difluoroalkyl ethers and carbonyl fluoride acetals by oxidative desulfurization-fluorination" *Synlett* pp. 251-252 (1994).

Kwong et al. "Hepatitis C virus NS3/4A protease" *Antiviral Res.* 41:67-84 (1999).

Lam, "Application of combinatorial library methods in cancer research and drug discovery" *Anticancer Drug Design* 12:145-167 (1997).

Lang et al. "Molecular screening of patients with long standing extensive ulcerative colitis: detection of p53 and Ki-*ras* mutations by single strand conformation polymorphism analysis and differential hybridisation in colonic lavage fluid" *Gut.* 44:822-825 (1999).

Larsson et al. "Thymidylate synthase in advanced gastrointestinal and breast cancers" *Acta Oncologica* 35(4):469-472 (1996).

Lasic, "Doxorubicin in sterically stabilized liposomes" *Nature* 380:561-562 (Apr. 11, 1996).

Leichman, "Thymidylate synthase as a predictor of response" *Oncol.* 12(8Suppl.6):43-47 (Aug. 1998).

Lenz et al., "Rapid quantitative PCR for determination of relative gene expressions in tissue specimens" *PCT Methods Appl.* 4:305-308 (1995).

Lenz et al., "p53 and thymidylate synthase expression in untreated stage II colon cancer: associations with recurrence, survival, and site" *Clinical Cancer Research* 4:1227-1234 (May 1998).

Leś et al., "Modeling of reaction steps relevant to deoxyuridylate (dUMP) enzymatic methylation and thymidylate synthase mechanism-based inhibition" *Journal of Biomolecular Structure & Dynamics* 15(4):703-715 (1998).

Lewis et al., "A serum-resistant cytofectin for cellular delivery of antisense oligodeoxynucleotides and plasmid DNA" *PNAS USA* 93:3176-3181 (Apr. 1996).

Lewis et al., "Differential responses of human tumor cell lines to anti-p185$^{HER2}$ monoclonal antibodies" *Cancer Immural. Immunother.* 37(4):255-263 (1993).

Li et al., "Lack of functional retinoblastoma protein mediates increased resistance to antimetabolites in human sarcoma cell lines" *PNAS USA* 92:10436-10440 (1995).

Lin et al., "Rhenium 188 hydroxyethylidene diphosphonate: a new generator-produced radiotherapeutic drug of potential value for the treatment of bone metastases" *Eur. J. Nucl. Med.* 24(6):590-595 (Jun. 1997).

Livak et al., "Detection of single base differences using biotinylated nucleotides with very long linker arms" *Nucl. Acids Res.* 20(18):4831-4837 (1992).

Livingstone et al., "Altered cell cycle arrest and gene amplification potential accompany loss of wild-type p53" *Cell* 70:923-935 (1992).

Lönn et al., "Higher frequency of gene amplification in breast cancer patients who received adjuvant chemotherapy" *Cancer* 77(1):107-112 (Jan. 1, 1996).

Lovejoy et al., "Animal models and the molecular pathology of cancer" *J. Pathol.* 181:130-135 (1997).

Mahalingam et al. "Structural and kinetic analysis of drug resistant mutants of HIV-1 protease" *Eur. J. Biochem.* 263:238-245 (1999).

Malfait et al., "The nonpsychoactive cannabis constituent cannabidiol is an oral anti-arthritic therapeutic in murine collagen-induced arthritis" *Proc. Natl. Acad. Sci.* 97(17):9561-9566 (Aug. 15, 2000).

Marinova-Mutafchieva et al., "A comparative study into the mechanisms of action of anti-tumor necrosis factor α, anti-CD4, and combined anti-tumor necrosis factor α/anti-CD4 treatment in early collagen-induced arthritis" *Arthritis and Rheumatism* 43(3):638-644 (Mar. 2000).

Masciullo et al., "The Rb family of cell cycle regulatory factors: clinical Implications (review)" *Int. J. Oncol.* 17(5):897-902 (2000).

Masters et al., "The nucleotide sequence of the cDNA coding for the human dihydrofolic acid reductase" *Gene* 21:59-63 (1983).

McGuigan, "Aryl phosphate derivatives of AZT retain activity HIV1 in cell lines which are resistant to the action of AZT" *Antiviral Res.* 17:311-321 (1992).

McGuigan, "Intracellular delivery of bioactive AZT nucleotides by aryl phosphate derivatives of AZT" *J. Med. Chem.* 36:1048-1052 (1993).

McGuigan, "Aryl phosphoramidate derivatives of d4T have improved anti-HIV efficacy in tissue culture and may act by the generation of a novel intracellular metabolite" *J. Med. Chem.* 39:1748-1753 (1996).

McGuigan et al., "Certain phosphoramidate derivatives of dideoxy uridine (ddU) are active against HIV and successfully by-pass thymidine kinase" *FEBS Lett.* 351:11-14 (1994).

McGuigan et al., "Synthesis and evaluation of some masked phosphate esters of the anti-herpetic drug 882C (nativudine) as potential antiviral agents" *Antiviral Chem. Chemother.* 9:187-197 (1998).

McIntee, "Probing the mechanism of action and decomposition of amino acid phosphomonoester amidates of antiviral nucleoside prodrugs" *J. Med. Chem.* 40:3323-3331 (1997).

McKay et al., "Broad spectrum aminoglycoside phosphotransferase type III from *Enterococcus*: Overexpression, purification, and substrate specificity" *Biochem* 33:6936-6944 (1994).

Mead et al. "Pharmacologic aspects of homofolate derivatives in relation to amethopterin-resistant murine leukemia" *Cancer Res.* 26(1):2374-2379 (Nov. 1966).

Meden et al., "Elevated serum levels of a c-erbB-2 oncogene product in ovarian cancer patients and in pregnancy" *J. Can. Res. Clin. Oncol.* 120:378-381 (1994).

Meier et al., "ADA-bypass by lipophilic *cyclosal*-ddAMP pronucleotides a second example of the efficiency of the *cyclosal*-concept" *Bioorg. Med. Chem. Lett.* 7(12):1577-1582 (1997).

Meier et al., "Cyclic saliganyl phosphotriesters of 2',3'-dideoxy-2',3'-didehydrothymidine (d4T)- a new pro-nucleotide approach" *Bioorg. Med. Chem. Lett.* 7(2):99 (1997).

Meier et al., "*Cyclo*Sal-pro-nucleotides: The design and biological evaluation of a new class of lipophilic nucleotide prodrugs" *Int'l. Antiviral News* 5(10):183-185 (1997).

Melton et al., "Antibody-enzyme conjugates for cancer therapy" *J. Natl. Can. Inst.* 88(3/4):153-165 (1996).

Miller, "Structural studies on cartilage collagen empolying limited cleavage and solubilization with pepsin" *Biochemistry* 11(26):4903-4909 (1972).

Miotla et al., "Treatment with soluble VEGF receptor reduces disease severity in murine collagen-induced arthritis" *Laboratory Investigation* 80(8):1195-1205 (Aug. 2000).

Montfort et al., "Thymidylate synthase: Structure, inhibition, and strained conformations during catalysis" *Pharmacol. Ther.* 76(1-3):29-43 (1997).

Montgomery et al., "Phosphonate analogue of 21-deoxy-5-fluorouridylic acid" *J. Med. Chem.* 22(1):109-111 (1979).

Morgan et al., "Tumor efficacy and bone marrow-sparing properties of TER286, a cytotoxin activated by glutathione *S*-transferase" *Cancer Res.* 58:2568-2575 (Jun. 15, 1998).

Mountz et al., "Autoimmune disease. A problem of defective apoptosis" *Arthritis & Rheumatism* 37(10):1415-1420 (Oct. 1994).

Mulder et al. "Thymidylate synthase levels in tumor biopsies from patients with colorectal cancer" *Anticancer Res.* 14(6B):2677-2680 (1994).

Murakami et al., "Accumulation of genetic alterations and their significance in each primary human cancer and cell line" *Mutat. Res.* 400(1-2):421-437 (1998).

Murray, "Antibiotic resistance" *Adv. Int. Med.* 42:339-367 (1997).

Naesens et al. "Anti-HIV activity and metabolism of phosphoramidate derivatives of D4T-MP with variations in the amino acid moiety" Poster Session 1, *The 10th International Conference on Antiviral Research*, Hotel Nikko, Atlanta, GA, Apr. 6-11, 1997, published in *Antiviral Research*, 34(2), p. A54, (Abstract 40), (Apr. 1997).

Nakano et al., "Critical role of phenylalanine 34 of human dihydrofolate reductase in substrate and inhibitor binding and in catalysis" *Biochem.* 33:9945-9952 (1994).

Negishi et al., "Enhancement of *N*4-aminocytidine-induced mutagenesis of Ni++ ion" *Nucl. Acids Symposium* 35:137-138 (1996).

Nichol and Hakala "Comparative growth-inhibitory activity of homofolic aid against cell lines sensitive and resistant to amethopterin" *Biochem. Pharmacol.* 15(10):1621-1623 (Oct. 1966).

Nooter et al., "Molecular mechanisms of multidrug resistance in cancer chemotherapy" *Pathol. Res. Pract.* 192:768-780 (1996).

Osaki et al., "5-fluorouracil (5-FU) induced apoptosis in gastric cancer cell lines: Role of the p53 gene" *Apoptosis* 2:221-226 (1997).

Oshiro et al. "Genotoxic properties of (*E*)-5-2'-deoxyuridine (BVDU)" *Fund. Appl. Toxicol.* 18:491-498 (1992).

Palmer et al. "Highly drug-resistant HIV-1 clinical isolates are cross-resistant to many antiretroviral compounds in current clinical development" *AIDS* 13(6):661-667 (1999).

Paradiso et al., "Thymidilate synthase and p53 primary tumour expression as predictive factors for advanced colorectal cancer patients" *British J. of Cancer* 82(3):560-567 (2000).

Pardo et al. "The Incorporation of deoxyuridine monophosphate in DNA increases the sister-chromatid exchange yield" *Exp Cell Res.* 168:507-517 (1987).

Park et al. "Chemotherapy efficacy of E-5-(2-bromovinyl)-2'-deoxyuridine for orofacial infection with herpes simplex virus type 1 in mice" *J. Infectious Diseases* 145(6):909-913 (1982).

Patterson et al. "Thymidine phosphorylase moderates thymidine-dependent rescue after exposure to the thymidylate synthase inhibitor ZD1694 (tomudex) in vitro" *Cancer Res.* 58:2737-2740 (1998).

Pedersen-Lane et al., "High-level expression of human thymidylate synthase" *Protein Expression and Purification* 10:256-262 (1997).

Pegram et al., "The effect of HER2/*neu* overexpression on chemotherapeutic drug sensitivity in human breast and ovarian cancer cells" *Oncogene* 15:537-547 (1997).

Pegram et al., "Inhibitory effects of combinations of HER-2/*neu* antibody and chemotherapeutic agents used for treatment of human breast cancers" *Oncogene* 18(13):2241-51 (1999).

Perry et al. "Plastic adaptation toward mutations in proteins: Structural comparison of thymidylate synthases" *Proteins* 8:315-333 (1990).

Pestalozzi et al., "Prognostic importance of thymidylate synthase expression in early breast cancer" *J. Clin. Oncol.* 15(5):1923-1931 (1997).

Peters et al., "Thymidylate synthase and drug resistance" *Eur. J. Can.* 31A(7/8):1299-1305 (1995).

Phelps et al., "Synthesis and biological activity of 5-fluoro-2'-deoxyuridine 5'-phosphorodiamidates" *J. Med. Chem.* 23:1229-1232 (1980).

Plath et al., "A novel function for the tumor suppressor p16$^{INK4a}$: induction of anoikis via upregulation of the $\alpha_5\beta_1$ fibronectin receptor" *J. Cell. Biol.* 150(6):1467-77 (Sep. 18, 2000).

Pluta et al., "Synthesis and biological properties of 4-hydroxy, 4-thio-5-pyrimidine derivatives" *Boll. Chim. Farm.* 138(1):30-33 (Jan. 1, 1999).

Portwine, "p53—The link between inflammation and cancer?" *Pediatr. Res.* 47(5):573 (2000).

Pupa et al., "The extracellular domain of the c-*erb*B-2 oncoprotein is released from tumor cells by proteolytic cleavage" *Oncogene* 8:2917-2923 (1993).

Roberts, "An isotopic assay for thymidylate synthetase" *Biochem.* 5(11):3546-3548 (1966).

Robins et al., "Nucleic acid related compounds. 31. Smooth and efficient palladium-copper catalyzed coupling of terminal alkynes with 5-iodouracil nucleosides" *Tetrahedron Lett.* 22:421-424 (1981).

Robins et al., "Nucleic acid related compounds. 38. Smooth and high-yield iodination and chlorination at C-5 of uracil bases and *p*-toluyl-protected nucleosides" *Can. J. Chem.* 60:554-557 (1982).

Robins et al., "Nucleic acid related compounds. 39. Efficient conversion of 5-iodo to 5-alkynyl and derivated 5-substituted uracil bases and nucleosides" *J. Org. Chem.* 48:1854-1862 (1983).

Rode, "Specificity of thymidylate synthase inactivation by 4,5-bisubstituted dUMP analogues" *M. Nencki Inst. Exp. Biol., Acta Biochimica Polonica* 40(3):363-368 (1993).

Rogulski et al. "Glioma cells transduced with an *Escherichia coli* CD/HSV-1 TK fusion gene exhibit enhanced metabolic suicide and radiosensitivity" *Hum. Gene Ther.* 8:73-85 (1997).

Roninson et al., "Amplification of specific DNA sequences correlates with multi-drug resistance in chinese hamster cells" *Nature* 309:626-628 (1984).

Ruth et al., "C-5 substituted pyrimidine nucleosides. 1. Synthesis of C-5 allyl, propyl, and propenyl uracil and cystosine nucleosides via organopalladium intermediates" *J. Org. Chem.* 43(14):2870-2876 (1978).

Santi, "Perspectives on the design and biochemical pharmacology of inhibitors of thymidylate synthetase" *J. Med. Chem.* 23(2):103-111 (Feb. 1980).

Sastry et al., "Membrane-permeable dideoxyuridine 5'-monophosphate analogue inhibits human immunodeficiency virus infection" *Mol. Pharmacol.* 41:441-445 (1992).

Satyam et al. "Design, synthesis, and evaluation of latent alkylating agents activated by glutathione s-transferase" *J. Med. Chem.* 39:1736-1747 (1996).

Sauter et al., "Heterogeneity of *erb*B-2 gene amplification in bladder cancer" *Can. Res.* 53:2199-2203 (1993).

Schiffer et al., "Crystal structure of human thymidylate synthase: A structural mechanism for guiding substrates into the active site" *Biochem.* 34:16279-16287 (1995).

Schimke, "Gene amplification in cultured cells" *J. Biol. Chem.* 263(13):5989-5992 (1988).

Segovia, "*Leishmania* gene amplification: A mechanism of drug resistance" *Annals Tropical Med. Parasitol.* 88(2):123-130 (1994).

Shafer and Vuitton, "Highly active antiretroviral therapy (HAART) for the treatment of infection with human immunodeficiency virus type 1" *Biomed. & Pharamcother*, 53:73-86 (1999).

Shepard et al., "Resistance of tumor cells to tumor necrosis factor" *J. Clin. Immunol.* 8(5):333-341 (1988).

Shepard et al., "Monoclonal antibody therapy of human cancer: taking the HER2 protooncogene to the clinic" *J. Clin. Immunol.* 11(3):117-127 (1991).

Shim et al., "Rb protein down-regulates the stress-activated signals through inhibiting c-Jun N-terminal kinase/stress-activated protein kinase" *J. Biol. Chem.* 275(19):14107-14111 (May 12, 2000).

Simon, "DMARDS in the treatment of rheumatoid arthritis: current agents and future developments" *Int. J. Clin. Pract.* 54(4):243-249 (May 2000).

Simon, "Cell biological mechanisms of multidrug resistance in tumors" *PNAS USA* 91:3497-3504 (1994).

Singh et al., "Studies on the preparation and isomeric composition of 186Re- and 188Re-pentavalent rhenium dimercaptosuccinic acid complex" *Nucl. Med. Commun.* 14:197-203 (1993).

Slamon et al., "Human breast cancer: Correlation of relapse and survival with amplification of the HER-2/*neu* oncogene" *Science* 235:177-182 (1987).

Slamon et al., "Studies of the HER-2/*neu* proto-oncogene in human breast and ovarian cancer" *Science* 244:707-712 (1989).

Smith et al. "Response to doxorubicin of cultured normal and cancerous human mammary epithelial cells" *J. Natl'l Cancer Inst.* 74(2):341-347 (Feb. 1985).

Smith et al., "Regulation and mechanisms of gene amplification" *Phil. Trans. Royal Soc. Lond. B* 347:49-56 (1995).

Snydman et al., "Analysis of trends in antimicrobial resistance patterns among clinical isolates of *Bacteroides fragilis* group species from 1990 to 1994" *Clin. Infectious Diseases* 23(Suppl. 1):S54-S65 (1996).

Staschke et al. "The in vitro anti-hepatitis B virus activity of FIAU [1-(2'-deoxy-2'-fluro-1-$\beta$-D-arabinofuranosyl-5-iodo)uracil] is selective, reversible, and determined, at least in part, by the host cell" *Antiviral Res.* 23:45-61 (1994).

Stout et al., "Structure-based design of inhibitors specific for bacterial thymidylate synthase" *Biochem.* 38:1607-1617 (1999).

Stühlinger et al., "Clinical therapy and HER-2 oncogene amplification in breast cancer: Chemo- vs radiotherapy" *J. Steriod Biochem. Mol. Biol.* 49(1):39-42 (1994).

Sugarman et al., "Recombinant human tumor necrosis factor-I: Effects on proliferation of normal and transformed cells in vitro" *Science* 230(4728):943-945 (1985).

Sukumar et al., "Specific patterns of oncogene activation in transplacentally induced tumors" *PNAS USA* 87:718-722 (1990).

Sun et al. "Wild type and mutant p53 differentially regulate the gene expression of human collagenase-3 (*hMMP-13*)" *J. Biol. Chem.* 275(15):11327-32 (Apr. 14, 2000).

Tak et al. "Rheumatoid arthritis and p53: how oxidative stress might alter the course of inflammatory diseases" *Immunol. Today* 21(2):78-82 (Feb. 2000).

Takeishi et al., "Nucleotide sequence of a functional cDNA for human thymidylate synthase" *Nucl. Acid Res.* 13(6):2035-2043 (1985).

Tanaka et al. "Effects of human cytomegalovirus immediate-early proteins on p53-mediated apoptosis in coronary artery smooth muscle cells" *Circulation* 99(13):1656-1659 (Apr. 6, 1999).

Tannock, "Treatment of cancer with radiation and drugs" *J. Clin. Oncol.* 14(12):3156-3174 (Dec. 1996).

Tennant et al., "Antiviral activity and toxicity of fialuridine in the woodchuck model of hepatitis B virus infection" *Hepatol.* 28(1):179-191 (1998).

Tolstikov et al., "Synthesis and DNA duplex stabilities of oligonucleotides containing C-5-(3-methoxypropynyl)-2'-deoxyuridine residues" *Nucleosides & Nucleotides* 16(3):215-225 (1997).

Touroutoglou et al. "Thymidylate synthase inhibitors" *Clin. Cancer Res.* 2(2):227-243 (Feb. 1996).

Troutner, "Chemical and physical properties of radionuclides" *Nucl. Med. Biol.* 14(3):171-176 (1987).

Tsavaris et al. "Multimodal biochemical modulation of 5-fluorouracil activity in advanced colorectal cancer with altopurinol, folinic acid and dipyridamol" *J. Chemother.* 2(2):123-126 (1990).

Turner et al. "Structural biology of HIV" *J. Mol. Biol.* 285:1-32 (1999).

Ubeda et al., "The large subunit of the DNA replication complex C (DSEB/RF-C140) cleaved and inactivated by caspace-3 (CPP32/YAMA) during fas-induced apoptosis" *J. Biol. Chem.* 272(31):19562-19568 (1997).

Valette et al., "Decomposition pathways and in vitro HIV inhibitory effects of isoddA pronucleotides: Toward a rational approach for intracellular delivery of nucleoside 5'-monophosphates" *J. Med. Chem.* 39:1981 (1996).

Van de Vijver et al., "Amplification of the *neu* (c-*erbB*-2) oncogene in human mammary tumors is relatively frequent and is often accompanied by amplification of the linked c*erbA* oncogene" *Mol. Cell. Biol.* 7(5):2019-2023 (1987).

van Laar, "Therapeutic efficacy of fluoropyrimidines depends on the duration of thymidylate synthase inhibition in the murine colon 26-B carcinoma tumor model" *Clin. Cancer Res.* 2(8):1327-1333 (Aug. 1996).

van Triest et al. "Thymidylate synthase level as the main predictive parameter for sensitivity to 5-fluorouracil, but not for folate-based thymidylate synthase inhibitors, in 13 nonselected colon cancer lines" *Clin. Cancer Res.* 5(3):643-654 (Mar. 1999).

Volm et al., "Relationship of inherent resistance to doxorubicin, proliferative activity and expression of P-glycoprotein 170, and glutathione S-transferase-X in human lung tumors" *Cancer* 70(4):764-769 (1992).

Wahba et al., "Direct spectrophotometric evidence for the oxidation of tetrahydrofolate during the enzymatic synthesis of thymidylate" *J. Biol. Chem.* 236(3):C11-C12 (1961).

Wallis et al., "Synthesis and anit-HIV activity of C4-modified pyrimidine nucleosides" *Il Farmaco* 54:83-89 (1999).

Wang et al., "Identification and characterization of Ich-3, a member of the interleukin-1J converting enzyme (ICE)/Ced-3 family and an upstream regulator of ICE" *J. Biol. Chem.* 271(34):20580-20587 (1996).

Wang, "Protease Inhibitors as potential anti-viral agents for the treatment of picornaviral infections" *Prog. Drug Res.* 52:197-219 (1999).

Wataya et al., "*trans*-5-(3,3,3-trifluoro-1-propenyl)-2'-deoxyuridylate: A mechanism-based inhibitor of thymidylate synthetase" *J. Med. Chem.* 22(4):339-340 (Apr. 1979).

Wataya et al., "Interaction of thymidylate synthetase with 5-nitro-2'-deoxyuridylate" *J. Biol. Chem.* 255(12):5538-5544 (Jun. 1980).

Weinberg, "The molecular basis of oncogenes and tumor suppressor genes" in *DNA: The Double Helix, Perspective and Prospective at Forty Years, Ann. NY Acad. Sci.* 758:331-8 (1995).

Wettergren et al., "Drug-specific rearrangements of chromosome 12 in hydroxyurea-resistant mouse SEWA cells: Support for chromosomal breakage model of gene amplification" *Somatic Cell. & Mol. Gen.* 20(4):267-285 (1994).

Whalen et al., "Human glutathione S-transferases" *Seminars in Liver Disease* 18(4):345-358 (1998).

Wolff and Naumann, "INK4 cell cycle Inhibitors direct transcriptional inactivation of NF-κB" *Oncogene* 18:2663-2666 (1999).

Wright et al., "Enhancement of retention and cytotoxicity of 2-chlorodeoxyadenosine in cultured human leukemic lymphoblasts by nitrobenzylthioinosine, an inhibitor of equilibrative nucleoside transport" *Leukemia* 14(1):52-60 (2000).

Yen et al., "Characterization of a hydroxyurea-resistant human KB cell line with supersensitivity to 6-thloguanine" *Can. Res.* 54:3686-3691 (1994).

Yin et al., "Wild-type p53 restores cell cycle control and inhibits gene amplification in cells with mutant p53 alleles" *Cell* 70:937-948 (1992).

Zeid et al., "Synthesis of new thiolated acyclonucleosides with potential anti-HBV activity" *Nucleosides & Nucleotides* 18(1):95-111 (1999).

Zhang et al., "Wild-type *p53* suppresses angiogenesis in human leiomyosarcoma and synovial sarcoma by transcriptional suppression of vascular endothelial growth factor expression" *Cancer Research* 60:3655-3611 (Jul. 1, 2000).

Zhou et al., "Target protease specificity of the viral serpin CrmA" *J. of Biol. Chem.* 272(12):7797-7800 (1997).

Aschele et al. "Immunohistochemical quantitation of thymidylate synthase expression in colorectal cancer metastases predicts for clinical outcome to fluorouracil-based chemotherapy" *J. Clin. Oncol.* (Jun. 1999) 17(6):1760-1770.

Bagshawe, K.D. "Antibody-directed enzyme prodrug therapy: A review" *Drug Development Res.* (1995) 34(2):220-230.

Balzarini et al. "Highly Selective Cytostatic Activity of (E)-5-(2-Bromovinyl)-2'-deoxyuridine Derivatives for Murine Mammary Carcinoma (FM3A) Cells Transformed with the Herpes Simplex Virus Type 1 Thymidine Kinase Gene" Molecular Pharmacology (1985) 28:581-587.

Barbato, et al. "Synthesis of bridged pyrimidine nucleosides and triazo [4,3-c] pyrimidine nucleoside analogues" *Nucleos. Nucleot.* (1991) 10(4):853-866.

Blackledge "New developments in cancer treatment with the novel thymidylate synthase inhibitor raltitrexed ('Tomudex')" *British J. Cancer* (1998) 77(2):29-37.

Cruickshank et al. "Oligonucleotide labeling: A concise synthesis of a modified thymidine phoporamidite" *Tetrahedron Lett.* (1988) 29(41):5221-5224.

Curtin et al. "Mechanism of Cell Death following Thymidylate Synthase Inhibition: 2'-Deoxyuridine-5'-triphosphate Accumulation, DNA Damage, and Growth Inhibition following Exposure to CB3717 and Dipyridamole" *Cancer Res.* (May 1, 1991) 51:2346-2352.

Dolnick et al. "rTS Gene Expression is Associated with Altered Cell Sensitivity to Thymidylate Synthase Inhibitors" *Adv. Enzyme Reg.* (1996) 36:165-180.

Farrow et al. "Synthesis and biological properties of novel phosphotriesters: A new approach to the introduction of biologically active nucleotides into cells" *J. Med. Chem.* (1990) 33(5):1400-1406.

Farrugia et al. "Single agent infusional 5-fluorouracil is not effective second-line therapy after raltitrexed (Tomudex® ) in advanced colorectal cancer" *Eur. J. Cancer* (1998) 34(7):987-991.

Freemantle et al. "Molecular characterisation of two cell lines selected for resistance to the folate-based thymidylate synthase inhibitor, ZD1694" *British Journal of Cancer* (1995) 71:925-930.

Goel et al. "Selective Intraperitoneal Biochemical Modulation of Methotrexate by Dipyridamole" *J. Clin. Oncol.* (Feb. 1989) 7(2):262-269.

Gorlick et al. "Drug Resistance in Colon Cancer" *Semin. Olcol.* (Dec. 1999) 26(6):606-611.

Griengl et al. "Phosphonoformate and phosphonoacetate derivatives of 5-substituted 2'deoxyuridines: Synthesis and antiviral activity" *J. Med. Chem.* (1998) 31(9):1831-1839.

Griffith et al. "Differential Inhibition of Nucleoside Transport Systems in Mammalian Cells by a New Series of Compounds Related to Lidoflazine and Mioflazine" *Biochem. Pharmacol.* (1990) 40(10):2297-2303.

Heidelberger et al. "Fluorinated pyrimidines and their nucleosides" Adv. Enzymol. Related Areas Mol. *Biol.* (1983) 54:57-119.

Howell et al. "Comparison of the Synergistic Potentiation of Etoposide, Doxorubicin, and Vinblastine Cytotoxicity by Dipyridamole" *Cancer Res.* (Jun. 15, 1989) 49:3178-3183.

Hu et al. "Determination of absorption characteristics of AG337, a novel thymidylate synthase inhibitor, using a perfused rat intestinal model" *J. Pharmaceutical Sciences* (Jul. 1998) 87(7):886-890.

Husain et al. "Elevation of topoisomerase I messenger RNA, protein, and catalytic activity in human tumors: Demonstration of tumor-type specificity and implications for cancer chemotherapy" *Cancer Research* (Jan. 15, 1994) 54:539-546.

Kraupp et al. "Membrane Transport of Nucleobases: Interaction with Inhibitors" *Gen. Parmacol.* (1995) 26(6):1185-1190.

Lackey et al. "Enzyme-catalyzed therapeutic agent (ECTA) design: activation of the antitumor ECTA compound NB1011 by thymidylate synthase" *Biochem. Pharmacol.* (2001) 61:179-189.

Lee et al. "Inhibition of mouse thymidylate synthase promoter activity by the wild-type p53 tumor suppressor protein" *Exp. Cell Res.* (1997) 234:270-276.

Lehman et al. "Modulation of RTX cytotoxicity by thymidine and dipyridamole in vitro: implications for chemotherapy" *Cancer Chemother. Pharmacol.* (2000) 45:142-148.

Leichman et al. "Quantitation of Intratumoral Thymidylate Synthase Expression Predicts for Disseminated Colorectal Cancer Response and Resistance to Protracted-Infusion Fluorouracil and Weekly Leucovorin" *J. Clin. Oncol.* (Oct. 1997) 15(10):3223-3229.

Lenz et al. "Thymidylate Synthase mRNA Level in Adenocarcinoma of the Stomach: A Predictor for Primary Tumor Response and Overall Survival" *J. Clin. Oncol.* (1995) 14(1):176-182.

Livingston et al. "Studies with tetrahydrohomofolate and thymidylate synthetase from amethopterin-resistant mouse leukemia cells" *Biochem.* (1968) 7(8):2814-2818.

Look et al. "Increased thymidine kinase and thymidylate synthase activities in human epithelial ovarian carcinoma" *Anticancer Res.* (1997) 17:2353-2356.

Madec et al. "Some characteristics of fetal and adult isoenzymes of thymidine kinase in human breast cancers" *Bull. Cancer* (1998) 75:187-194.

Mader et al. "Resistance to 5-fluorouracil" *Gen. Pharma.* (1998) 31(5):661-666.

Mahony et al. "Dipyridamole Kinetics" *Clin. Pharmacol. Ther.* (Mar. 1982) 31(3):330-338.

Melton et al. "Antibody-directed enzyme prodrug therapy (ADEPT). Review article" *Drugs of the Future* (1996) 21(2):167-181.

Midgley and Kerr "Colorectal cancer" *Lancet* (Jan. 30, 1999) 353:391-399.

Nelson et al. "Potentiation of Methotrexate Toxicity by Dipyridamole" *Cancer Res.* (Jun. 1984) 44:2493-2496.

Niculescu-Duvaz et al. "Gene-directed enzyme prodrug therapy: A review of enzyme/prodrug combinations" *Expert Opin. Invest. Drugs* (1997) 6(6):685-703.

Ramu et al. "Circumvention of Adriamycin Resistance by Dipyridamole Analogues: A structure-activity relationship Study" *Int. J. Cancer* (1989) 43:487-491.

Romain et al. "Prognostic value of cytosolic thymidine kinase activity as a marker of proliferation in breast cancer" *Int. J. Cancer* (1995) 61:7-12.

Rooney et al. "Comparative Genomic Hybridization Analysis of Chromosomal Alterations Induced by the Development of Resistance to Thymidylate Synthase Inhibitors" *Cancer Res.* (Nov. 15, 1998) 58:5042-5045.

Roth et al. "p53 tumor suppressor gene therapy for cancer" *Oncology* (1999) 13(10)(5):148-154.

Saboulard et al. "Characterization of the activation pathway of phosphoramidate triester prodrugs of stavudine and zidovudine" *Mol. Pharmacol.* (1999) 56:693-704.

Schultz et al. "Role of thymidylate synthase in the antitumor activity of the multitargeted antifolate, LY231514" *Anticancer Res.* (1999) 19:437-444.

van Laar et al. "Comparision of 5-fluoro-2'-deoxyuridine with 5-fluorouracil and their role in the treatment of colorectal cancer" *European J. Cancer* (1998) 34(3):296-306.

Wolfe et al. "Antibody-directed enzyme prodrug therapy with the T268G mutant of human carboxypeptidase A1: in vitro and in vivo studies with prodrugs of methotrexate and the thymidylate synthase" *Bioconjugate Chemistry* (1999) 10(1):38-48.

Balzarini et al., "Increased sensitivity of thymidine kinase-deficient (TK-) tumor cell lines to the cell growth inhibitory effects of (E)-5-(2-bromovinyl)-2'-deoxyuridine (BVDU) and related compounds", Anticancer Research, vol. 6, 1986, pp. 1077-1084, Belgium, 1986.

Balzarini et al., "Marked inhibitory activity of masked aryloxy aminoacyl phosphoramidate derivatives of dideoxynucleoside analogues against visna virus infection", Journal of Acquired Immune Deficiency Syndromes and Human Retrovirology, vol. 17, pp. 296-302, Belgium, 1998.

Costi, M. Paola "Thymidylate Synthase Inhibition: A Structure-Based Rationale for Drug Design" *Medical Research Review* 18(1):21-42 (1998).

Miao et al. "A Stepwise One Pot Synthesis of Alkyl Thiophosphoramidate Derivatives of Nucleosides" *Synthetic Communications* 32(8):1159-1167 (2002).

* cited by examiner

PHOSPHORAMIDATE COMPOUNDS AND METHODS OF USE

CROSS-REFERENCE TO RELATED APPLICATIONS

This application claims priority under 35 U.S.C. § 120 of U.S. Ser. No. 09/782,721, filed Feb. 12, 2001, which is a continuation of U.S. Ser. No. 09/235,961, filed Jan. 22, 1999, now U.S. Pat. No. 6,339,151B1, which in turn claims priority under 35 U.S.C. § 119(e) of U.S. Provisional Application Nos. 60/072,264; 60/076,950; and 60/108,634, filed Jan. 23, 1998, Mar. 5, 1998, and Nov. 16, 1998, respectively, now all abandoned. This application also claims priority under 35 U.S.C. § 120 of U.S. Ser. No. 09/856,127, filed Jul. 21, 1999, now U.S. Pat. No. 6,683,061, which in turn claims priority under 35 U.S.C. § 119(e) of U.S. Provisional Ser. Nos. 60/145,356; 60/145,437; and 60/191,315, filed Jul. 21, 1999, Jul. 22, 1999 and Mar. 21, 2000, respectively, now all abandoned. It also claims priority under 35 U.S.C. § 120 to U.S. Ser. No. 09/990,799, filed Nov. 16, 2001, which in turn claims priority under 35 U.S.C. § 119(e) to U.S. Provisional Application No. 60/249,722, filed Nov. 16, 2000, now abandoned. This application further claims priority under 35 U.S.C. § 120 to U.S. Ser. No. 10/051,320, filed Jan. 18, 2002, which in turn claims priority under 35 U.S.C. § 119(e) to U.S. Provisional Ser. No. 60/262,849, filed Jan. 19, 2001, now abandoned. The contents of all of the aforementioned applications are hereby incorporated by reference into the present disclosure.

TECHNICAL FIELD

The present invention is in the field of medicinal chemistry and relates to other areas such as pharmacology, oncology and immunology. In particular, it provides compounds and methods to treat hyperproliferative disorders.

BACKGROUND

Throughout and within this disclosure, various publications, patents, published patent applications and references are identified by first author and date, within parentheses, patent number, publication number or by web address. If the complete bibliographic citation is not provided after the publication or reference, it is at the end of the specification, immediately preceding the claims. The disclosures of all publications, references and information provided at the web addresses are hereby incorporated by reference into this disclosure to more fully describe the state of the art to which this invention pertains.

Hyperproliferative cells grow at a rate over that of normal or healthy cells. The presence of these abnormal cells has been linked to many pathologies, e.g., cancer, infectious disease, autoimmune disorders and inflammatory conditions or diseases. In many instances, they are useful diagnostic indicators. In other instances, subcellular changes linked to progression toward the hyperproliferative state are useful prognostic indicators of disease progression or its curative treatment.

Cancer cells are hyperproliferative, i.e., characterized by uncontrolled growth, de-differentiation and genetic instability, that express as aberrant chromosome number, chromosome deletions, rearrangements, loss or duplication beyond the normal diploid number. (Wilson, J. D. et al. (1991)). This genomic instability may be caused by several factors. One of the best characterized is the enhanced genomic plasticity which occurs upon loss of tumor suppressor gene function (e.g., Almasan, A. et al. (1995a) and Almasan, A. et al. (1995b)). The genomic plasticity lends itself to adaptability of tumor cells to their changing environment, and may allow for the more frequent mutation, amplification of genes, and the formation of extrachromosomal elements (Smith, K. A. et al. (1995) and Wilson, J. D. et al. (1991)). These characteristics provide for mechanisms resulting in more aggressive malignancy because they allow tumors to rapidly develop resistance to natural host defense mechanisms, biologic therapies (See Wilson, J. D. et al. (1991) and Shepard, H. M. et al. (1988)), as well as to chemotherapeutics (See Almasan, A. et al. (1995a); and Almasan, A. et al. (1995b)).

The heterogeneity of malignant tumors with respect to their genetics, biology and biochemistry as well as primary or treatment-induced resistance to therapy mitigate against curative treatment. Moreover, many anticancer drugs display only a low degree of selectivity, causing often severe or even life threatening toxic side effects, thus preventing the application of doses high enough to kill all cancer cells. Searching for anti-neoplastic agents with improved selectivity to treatment-resistant pathological, malignant cells remains, therefore, a central task for drug development.

The function of tumor suppressor genes is a major focus of recent attempts to develop innovative therapeutics for the treatment cancer. The products of tumor suppressor gene expression are generally characterized as negative regulators of cell proliferation (Knudson, A. G. (1993) and Weinberg, R. A. (1995)). Thus, therapeutic approaches to date include gene therapies to restore inactive or missing tumor suppressor function in cancer cells to re-establish normal cellular function or induce apoptosis (Clayman, G. L. (2000) and Knudson, A. G. (1993)).

Loss of RB/p16 function can result in similar proinflammatory, proliferative and dedifferentiating effects on cells (Carson, R. A. and Haneji, N. (1999); Shim, J. et al. (2000); Wolff, B. and Naumann, M. (1999); DiCiommo et al. (2000)), and alteration in cell-cell interactions (Plath et al. (2000)). Inactivation of tumor suppressor function by somatic mutation or via interaction with virally-encoded proteins is proposed to contribute to the proliferative/inflammatory aspect of athersclerosis, restenosis or other hyperproliferative diseases (Tanaka, K. et al. (1999); Aoki, M. et al. (1999); Guevara, N. V. et al. (1999); and Iglesias, M. et al. (1998)). Finally, the expression of the proinflammatory cytokine, macrophage inhibitory factor (MIF), may be capable of inactivating p53 function in some cell types (Hudson, J. D. et al. (1999); Cordon-Cardo, C. and Prives, C. (1999); and Portwine, C. (2000)).

Functional loss of tumor suppressor genes also has been linked to inflammatory or autoimmune diseases that have cellular hyperproliferation as one of their characteristics (Cordan-Cardo, C. and Prives, C. (1999)) and/or defective apoptosis (programmed cell death) (Mountz, J. D. et al. (1994)). These include: rheumatoid arthritis, systemic lupus erythmatosus, psoriatic arthritis, reactive arthritis, Crohn's disease, ulcerative colitis and scleroderma. Table 1 lists literature examples which suggest that such a link may exist.

TABLE 1

Literature Examples Suggesting that Biological Expression of p53 Tumor Suppressor Mutation/Inactivation Relates to Noncancer Hyperproliferative Disease, Autoimmune Disease and Inflammation.

| Impact | Disease Effect | Reference |
|---|---|---|
| Increased IL6 | Proliferation Inflammation Rheumatoid Arthritis | Han, et al. (1999) |
| Increased metalloproteinases | Tissue Degradation | Sun, Y. et al. (2000) |
| Increased proliferation of al. synovial cells | Rheumatoid arthritis | Aupperle, K. R. et (1998) |
| Genetic instability | Chronic inflammation | Tak, P. P. et al. (2000) |
| and disease progression | Ulcerative colitis | Lang, S. M. et al. (1999) |
| Increased expression of E2F regulated genes (TS, DHFR) | Proliferation Drug resistance Multiple autoimmune and inflammatory diseases | Banerjee, D. et al. (1998) |
| Viral proteins expression leading to p53 inactivation | Athersclerosis | Tanaka, K. et al. (1999) |
| Increased angiogensis | Supports hyper-proliferative States, ex. enabling atheromaorpannus formation. | Zhang, L. et al. (2000) |

The hyperproliferative phenotype has also been linked to resistance to chemotherapy in cancer, infectious disease, autoimmune disease and inflammatory conditions. Some hyperproliferative cells overexpress an intracellular enzyme that is related to any of a loss of tumor suppressor gene product function, drug resistance or genetic instability. A number of cellular mechanisms are involved in drug resistance, e.g., altered metabolism of the drug, impermeability of the cell with regard to the active compound or accelerated drug elimination from the cell, altered specificity of an inhibited enzyme, increased production of a target molecule, increased repair of cytotoxic lesions, or the bypassing of an inhibited reaction by alternative biochemical pathways. Enzymes activated or overexpressed and related to drug resistance include, but are not limited to thymidylate synthase (TS) (Lönn, U. et al. (1996); Kobayashi, H. et al. (1995); Jackman, A. L. et al. (1995)), dihydrofolate reductase (Banerjee, D. et al. (1995) and Bertino, J. R. et al. (1996)), tyrosine kinases (TNF-α, Hudziak, R. M. et al. (1988)) and multidrug resistance (Stühlinger, M. et al. (1994)); Akdas, A. et al. (1996); and (Tannock, I. F. (1996)); and ATP-dependent multidrug resistance associated proteins (Simon, S. M. and Schnindler, M. (1994)). Alternatively, resistance to one drug may confer resistance to other, biochemically distinct drugs. Amplication of certain genes is involved in resistance to chemotherapy. Amplification of dihydrofolate reductase (DHFR) is related to resistance to methotrexate while amplification of the gene encoding thymidylate synthase is related to resistance to tumor treatment with 5-fluoropyrimidine.

Overexpression of enzymes encoded by human and animal pathogens, and in which the inhibitors have failed due to development of resistance, also has been linked to disease. Indeed, resistance to antibiotics is a major health care problem. In infectious disease, most drug resistance is enzyme mediated. Typically, an enzyme expressed by the infectious agent rapidly modifies the chemotherapeutic or antibiotic, thereby abolishing its therapeutic activitiy. Amplified expression of beta-lactamases accounts for more than one-third of all beta-lactam antibiotic resistant isolates (Felmingham and Washington (1999)), including the majority of resistant *Haemophilis influenza* (upper respiratory infections) and *Moraxella catarrhalis* (otitis media). In addition, genes conferring resistance to various alternative types of antibiotics occur in nature and have become increasing common in populations of infectious organisms. Recently, infectious agents carrying sets of genes simultaneously conferring resistance to multiple antibiotic agents have arisen making treatment by traditional antibiotic therapy difficult.

Thus, novel compounds and therapies are necessary overcome the limitations of current therapies. This invention satisfies this need and provides related advantages as well.

DISCLOSURE OF THE INVENTION

Novel phosphoramidatyl, 1,5-substituted pyrimidine compounds, derivatives, analogs, and pharmaceutically acceptable salts thereof and compositions containing the compounds are provided by this invention. The compounds can be combined with an additional therapeutic drug or therapy. The compounds and compositions are useful diagnostically and therapeutically.

This invention provides methods for treating cells or tissue involved in a pathology characterized by hyperproliferative cells. Examples of pathologies include, but are not limited to cancer, infectious disease, autoimmune disease and an inflammatory condition. The cells and/or tissue are contacted with an effective amount of one or more of a compound of this invention. Applicants have previously noted that some compounds of this class are effective in treating hyperproliferative disorders. See U.S. Pat. No. 6,339,151B1 and 6,245,750, issued Jan. 15, 2002 and Jun. 12, 2001, respectively and published international patent applications PCT/US00/19844; PCT/US00/20007; and PCT/US00/20008.

The methods can be practiced in vitro, ex vivo and in vivo. In one aspect, the cells or tissue are characterized by loss of tumor suppressor function. In another aspect, the pathological mcells overexpress an endogenous intracellular enzyme such as thymidylate synthase or a target enzyme. In yet a further aspect, the cells have become resistant to a chemotherapeutic drug, e.g., 5-fluorouracil (5FU). In another aspect, an infectious agent overexpresses a target enzyme which in turn confers resistance.

When practiced in vivo, the invention provides a method for treating a subject having a pathology characterized by hyperproliferative cells, e.g., cancer, an infectious disease, autoimmune disorder or an inflammatory condition, by delivering to the subject an effective amount of at least one or more of the 5'-phosphoramidatyl, 1,5-substituted pyrimidine, derivative, analog or pharmaceutically acceptable salt thereof. Methods for synthesizing the compounds are described herein and in Applicants' prior patent literature, e.g., PCT/US98/16607 and PCT/US99/01332, which describe the compounds as "ECTA" compounds or prodrugs.

The methods are further useful to treat or ameliorate the symptoms of a hyperproliferative disorder, e.g., cancer, infectious disease, autoimmune disease or an inflammatory condition, in a subject by administering to the subject an effective amount of a compound or composition of this invention.

Further provided are compositions and methods for reversing resistance to a chemotherapeutic by contacting the resistant cells or tissue with a compound of this invention. Yet further provided are methods and compositions for enhancing the efficacy of drugs that treat or ameliorate symptons associated with cancer, infectious disease, autoimmune disease or an inflammatory condition.

Assays for identifying agents, therapies and combinations thereof that inhibit the growth of pathological cells or tissue are also provided herein.

MODES FOR CARRYING OUT THE INVENTION

General Techniques

Figure 1:
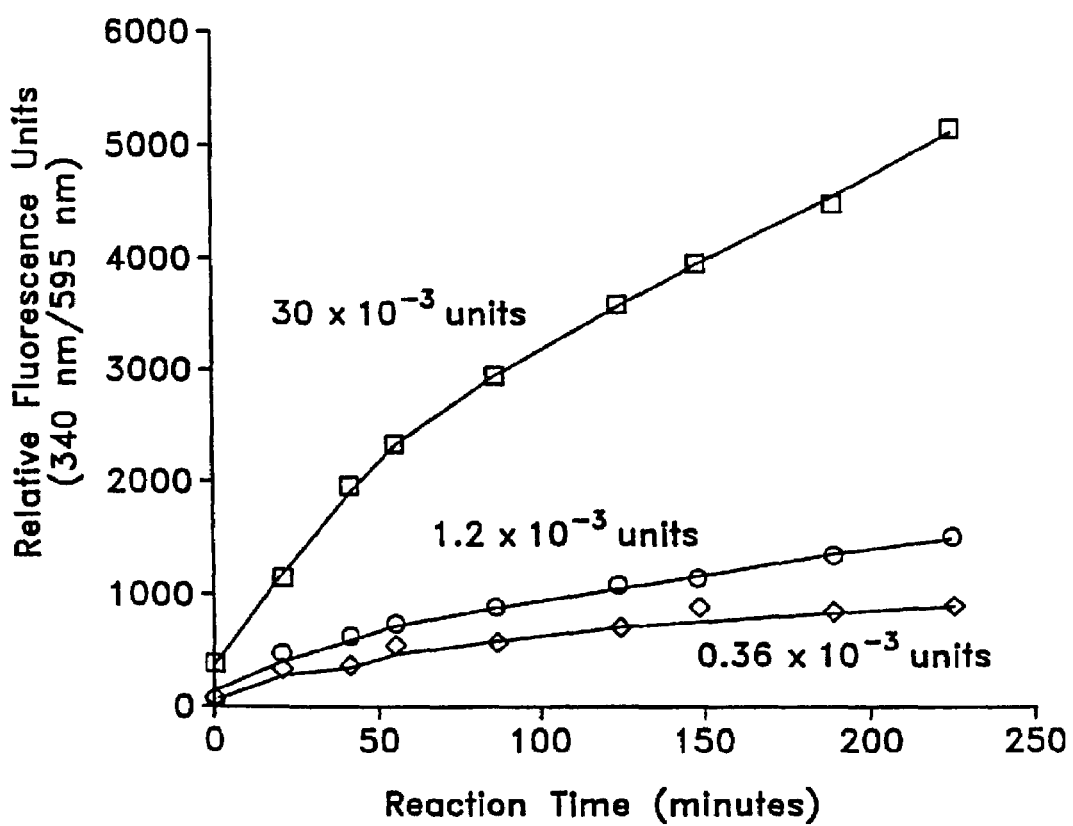
FIG. 1 is a graph showing fluorescent products from incubation of Bromovinyl, 2'-Deoxyuridine Monophosphate ("BVdUMP") with Recombinant Human Thymidylate Synthase ("rHuTS"). Incubation of BVdUMP with thymidylate synthase ("TS") results in a time and enzyme dependent generation of fluorescent product(s). BVdUMP was incubated with the indicated amounts of rHuTS in the standard reaction mixture at 30° C. (Materials and Methods), except that N5, N10-methylenetetrahydrofolate was omitted from the reaction. The numbers adjacent to each data curve refer to TS enzyme units.

The practice of the present invention will employ, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "MOLECULAR CLONING: A LABORATORY MANUAL" Second Edition (Sambrook et al., 1989); "OLIGONUCLEOTIDE SYNTHESIS" (M. J. Gait, ed., 1984); "ANIMAL CELL CULTURE" (R. I. Freshney, ed., 1987); the series "METHODS IN ENZYMOLOGY" (Academic Press, Inc.); "HANDBOOK OF EXPERIMENTAL IMMUNOLOGY" (D.M. Weir & C. C. Blackwell, eds.); "GENE TRANSFER VECTORS FOR MAMMALIAN CELLS" (J. M. Miller & M. P. Calos, eds., 1987); "CURRENT PROTOCOLS IN MOLECULAR BIOLOGY" (F. M. Ausubel et al., eds., 1987, and periodic updates); "PCR: THE POLYMERASE CHAIN REACTION" (Mullis et al., eds., 1994); "CURRENT PROTOCOLS IN IMMUNOLOGY" (J. E. Coligan et al., eds., 1991); and J. March, ADVANCED ORGANIC CHEMISTRY: REACTIONS, MECHANISMS AND STRUCTURE, $4^{th}$ edition (John Wiley & Sons, NY (1992)).

DEFINITIONS

As used herein, certain terms may have the following defined meanings.

As used in the specification and claims, the singular form "a," "an" and "the" include plural references unless the context clearly dictates otherwise. For example, the term "a cell" includes a plurality of cells, including mixtures thereof. Similarly, use of "a compound" for treatment or preparation of medicaments as described herein contemplates using one or more compounds of this invention for such treatment or preparation unless the context clearly dictates otherwise.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "analog" is intended to mean a structural derivative of a compound that differs from it by at least one element. The term "derivative" is intended to mean a compound derived or obtained by another and containing the essential elements of the parent substance.

The term "alkyl" refers to and covers any and all groups which are known as normal alkyl, branched-chain alkyl and cycloalkyl. As used herein, "alkyl" is intended to include both branched, straight-chain, substituted or unsubstituted saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl.

Lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower allynyl groups, and 4 to 6 carbons for branch chained lower alkynyl groups.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl.

"Carbocyclic" is intended to include saturated or unsaturated ring groups, such as cyclopropyl, cyclobutyl, or cyclopentyl. They may be substituted or unsubstituted.

The term "alkenyl" refers to and covers normal alkenyl, branch chain alkenyl and cycloalkenyl groups having one or more sites of unsaturation. Similarly, the term alkynyl refers to and covers substituted or unsubstituted normal alkynyl, and branch chain alkynyl groups having one or more triple bonds. "Alkynyl" is intended to include hydrocarbon chains of either a substituted or unsubstituted straight or branched configuration and one or more triple carbon-carbon bonds which may occur in any stable point along the chain, such as ethynyl and propynyl.

Some of the compounds of the present invention may have trans and cis (E and Z isomers. In addition, the compounds of the present invention may contain one or more chiral centers and therefore may exist in enantiomeric and diasteromeric forms. Still further oxi and related compounds of the present invention may exist in syn and anti isomeric forms. The scope of the present invention is intended to cover all such isomers per se, as well as mixtures of cis and trans isomers, mixtures of syn and anti isomers, mixtures of diastereomers and racemic mixtures of enantiomers (optical isomers) as well. In the present application, when no specific mention is made of the configuration (cis, trans, syn, anti, R or S) of a compound (or of an asymmetric carbon) then a mixture of such isomers, or either one of the isomers is intended. In a similar vein, when in the chemical structural formulas of this application a straight line representing a valence bond is drawn to an asetric carbon, then both isomers of both R and S configuration, as well as their mixtures are intended. Defined stereochemistry about an asymmetric carbon is indicated in the formulas (where applicable) by a solid triangle showing beta configuration, or by a hashed line showing alpha configuration.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

A "subject" is a vertebrate, preferably a mammal, more preferably a human. Mammals include, but are not limited to, murines, simians, humans, farm animals, sport animals, and pets.

An "effective amount" is an amount sufficient to effect beneficial or desired results. For example, a therapeutic amount is one that achieves the desired therapeutic effect. This amount may be the same or different from a prophylatically effective amount, which is an amount necessary to prevent onset of disease or disease symptoms. An effective amount can be administered in one or more administrations, applications or dosages.

A "pathological cell" is one that is pertaining to or arising from disease. In one aspect, a pathological cell is identified from normal or healthy cells by presence of an endogenous intracellular enzyme such as TS or an activating enzyme. In another aspect, the cell overexpresses the enzyme (such as TS). In yet another aspect, the cell has become resistant to prior drugs or therapy. In a further aspect, the cell has defective tumor suppressor function. In yet a further aspect, the expression of the activating enzyme occurs as a consequence of infection by a pathogenic organism.

Pathological cells can be hyperproliferative. A "hyperproliferative cell" means cells or tissue are dividing and growing at a rate greater than that when the cell or tissue is in a normal or healthy state. Examples of such include, but are not limited to cancer cells, cells associated with autoimmune or inflammatory conditions and cells associated with infectious disease, e.g., bacteria, parasites, virus, yeast, fungi, or plant or animal cells infected with an agent. Examples of viruses include but are not limited to Herpes, Varicella zoster, Hepatitis C and Epstein Barr virus. Examples of parasites include but are not limited to *T. brucei, T. cruzi*, and *Plasmodium falciparum*. Examples of bacteria include, but are not limited to, all gram positive and gram negative bacteria, especially, *Staphylococcus*, sp., *Enterococcus* sp., *Myoplasma* sp., *E. coli* sp., *Psudomonas* sp., *Nisseria* sp. In one embodiment, the infectious agents have become resistant to common antibiotics (see review by Murray, B. E. (1997)). In other embodiments, the infectious agent expresses a "target enzyme" not expressed by the host cell.

Hyperproliferative cells also include de-differentiated, immortalized, neoplastic, malignant, metastatic, and cancer cells such as sarcoma cells, leukemia cells, carcinoma cells, or adenocarcinoma cells. Specified cancers include, but are not limited to breast cancer cells, hepatoma cells, liver cancer cells, pancreatic carcinoma cells, esophageal carcinoma cells, bladder cancer cells, gastrointestinal cancer cells, ovarian cancer cells, skin cancer cells, prostate cancer cells, and gastric cancer cells.

In one aspect, hyperproliferative cells overexpress an intracellular enzyme that is related to any of a loss of tumor suppressor gene product function, e.g. loss or inactivation of retinoblastoma (RB) or p53, known to enhance expression of TS (Li, W. et al. (1995) or DHFR (Bertino, et al. (1996) and Li, W. et al. (1995)), drug resistance (e.g., amplification of the gene encoding TS is related to resistance to tumor treatment with 5-fluoropyrimidines), or genetic instability or associated with a pathological phenotype. Alternatively, resistance to one drug may confer resistance to other, biochemically distinct drugs.

The enzyme glutathione-S-transferase was shown to be occasionally elevated in some human tumors (Morgan, A. S. et al. (1998)), but nevertheless is excluded from an enzyme that is overexpressed as used herein because it is a member of a gene family encoding enzymes with overlapping specificities.

A "pathology characterized by hyperproliferative cells" includes but is not limited to cancer, infectious disease, neoplasia, autoimmune disorders and inflammatory conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions of about 6×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15M NaCl and 15 mM citrate buffer. It is understood that equivalents of SSC using other buffer systems can be employed.

A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+SwissProtein+SPupdate+PIR. Details of these programs can be found at the following Internet address: http://www.ncbi.nlm.nih.gov/cgi-bin/BLAST.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced to a cell of such organism in vivo.

The term "isolated" means separated from constituents, cellular and otherwise, in which the polynucleotide, peptide, polypeptide, protein, antibody, or fragments thereof, are normally associated with in nature. For example, with respect to a polynucleotide, an isolated polynucleotide is one that is separated from the 5' and 3' sequences with which it is normally associated in the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

"Host cell," "target cell" or "recipient cell" are intended to include any individual cell or cell culture which can be or have been recipients for compounds or compositions of this invention, test agents, vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

A "subject" is a vertebrate, preferably an animal or a mammal, more preferably a human. Mammals include, but are not limited to, murines, simians, humans, farm animals, sport animals, and pets.

A "control" is an alternative subject or sample used in an experiment for comparison purpose. A control can be "positive" or "negative". For example, where the purpose of the experiment is to determine a correlation of the efficacy of a novel compound for the treatment for a particular type of cancer, it is generally preferable to use a positive control (a compound known to exhibit the desired therapeutic effect) and a negative control (a subject or a sample that does not receive the therapy or receives a placebo).

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue. Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modem usage generally denotes a neoplasm. The suffix "-oma" means tumor and usually denotes a benign neoplasm, as in fibroma, lipoma, and so forth, but sometimes implies a malignant neoplasm, as with so-called melanoma, hepatoma, and seminoma, or even a non-neoplastic lesion, such as a hematoma, granuloma, or hamartoma. The suffix "-blastoma" denotes a neoplasm of embryonic cells, such as neuroblastoma of the adrenal or retinoblastoma of the eye.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues.

One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

"Suppressing" tumor growth indicates a growth state that is curtailed compared to growth without any therapy. Tumor cell growth can be assessed by any means known in the art, including, but not limited to, measuring tumor size, determining whether tumor cells are proliferating using a $^3$H-thymidine incorporation assay, or counting tumor cells. "Suppressing" tumor cell growth means any or all of the following states: slowing, delaying, and "suppressing" tumor growth indicates a growth state that is curtailed when stopping tumor growth, as well as tumor shrinkage.

The term "culturing" refers to the in vitro propagation of cells or organisms on or in media of various kinds. It is understood that the descendants of a cell grown in culture may not be completely identical (morphologically, genetically, or phenotypically) to the parent cell. By "expanded" is meant any proliferation or division of cells.

An "autoimmune disorder" is any condition in which an organism produces antibodies or immune cells which recognize the organism's own molecules, cells or tissues. Non-limiting examples of autoimmune disorders include rheumatoid arthritis, Sjogren's syndrome, graft versus host disease, myasthenia gravis, and systemic lupus erythematosus.

An "inflammatory condition" shall mean those conditions that are characterized by a persistent inflammatory response with pathologic sequelae. This state is characterized by infiltration of mononuclear cells, proliferation of fibroblasts and small blood vessels, increased connective tissue, and tissue destruction. Chronic inflammatory diseases include Crohn's disease, psoriasis, and asthma, are also included within the term "inflammatory condition." Autoimmune diseases such as rheumatoid arthritis and systemic lupus erythematosus can also result in a chronic inflammatory state.

For the purpose of illustration only, treatment can be noted by reduction in the expression of an endogenous intracellular enzyme, e.g., TS, reduction in the numbers of infectious agents, the reduction in inflammation, reduction of self-recognizing immune factors. In a further aspect, treatment is noted by the amelioration or reduction of symptoms of the disease, e.g., reduction in pathological cell growth or turnover, cachexia, tumor burden or elevated levels of immunological factors associated with a pathological or unhealthy state.

Treatment of arthritic conditions can result in decreased blood vessel formation in cartilage, specifically joints, resulting in increased mobility and flexibility in these regions. Treatment of psoriasis, administrationwill reduce dermatological symptoms such as scabbing, flaking and visible blood vessels under the surface of the skin.

In vitro treatment includes induction of apoptosis, as well as clinical (histological) and sub-clinical (e.g., biochemical and genetic changes associated with a reversal or dimunition of the pathological state.) Clinical and sub-clinical evidence of "treatment" will vary with pathology, the individual or subject, the cell or tissue type and the treatment.

"An endogenous intracellular enzyme" is one that is expressed by the cell whose regulation or expression can vary. In one aspect, the enzyme selectively activates a compound of this invention to produce products that confers treatment. In one aspect, the enzyme is overexpressed in a diseased cell as compared to a normal healthy cell. An example of such is thymidylate synthase (TS).

The term "activating enzyme" as used herein means an enzyme that is expressed by a pathogen in its native or natural environment. It is intended to distinguish enzymes or other agents that are administered to activate a prodrug.

A "composition" is intended to mean a combination of active agent and another compound or composition, inert (for example, a solid support, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARMACEUTICAL SCIENCES, 15th Ed., Mack Publ. Co., Easton, Pa. (1975).

The Compounds

Therapeutic compounds for use in the methods of this invention are one or more 5'-phosphoramidatyl 1,5-substituted pyrimidines, derivatives, analogs or pharmaceutically acceptable salts thereof. The compounds of this invention are nucleoside analogs comprising a substituted or unsubstituted uracil base covalently joined to a sugar modified by at least the addition of a 5'-phosphoramidate containing an amino acid residue. In one aspect, one or more of the compounds are substituted at the 5-position with a group that is extractable from pyrimidine by an endogenous, intracellular enzyme. The substituent at the 1-position of uridine is selected from the group consisting of substituted sugar, substituted thio-sugar, substituted carbocyclic, substituted cycloalkyl, and substituted acyclic substituents. Examples of sugar groups include, but are not limted to, monosaccharide cyclic sugar groups such as those derived from oxetanes (4-membered ring sugars), furanoses (5-membered ring sugars), and pyranoses (6-membered ring sugars). Examples of furanoses include threo-furanosyl (from threose, a four-carbon sugar); erythro-furanosyl (from erythrose, a four-carbon sugar); ribo-furanosyl (from ribose, a five-carbon sugar); ara-furanosyl (also often referred to as arabino-furanosyl; from arabinose, a five-carbon sugar); xylo-furanosyl (from xylose, a five-carbon sugar); and lyxo-furanosyl (from lyxose, a five-carbon sugar), and nucleoside analogs thereof.

Examples of thio sugar groups include the sulfur analogs of the above sugar groups, in which the ring oxygen has been replaced with a sulfur atom. Examples of carbocyclic groups include $C_4$ carbocyclic groups, $C_5$ carbocyclic groups, and $C_6$ carbocyclic groups which may further have one or more substituents, such as —OH groups.

Derivatives of the compounds of this invention include, for example, "deoxy", "keto", and "dehydro" derivatives as well as substituted derivatives. Derivatives also include salts, esters, and ethers of the above compounds. Salts of the compounds of the present invention may be derived from inorganic or organic acids and bases. Examples of acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, can be employed in the preparation of salts useful as intermediates in obtaining the compounds of the invention and their pharmaceutically acceptable acid addition salts. Examples of bases include alkali metal (e.g., sodium) hydroxides, alkaline earth metal (e.g., magnesium) hydroxides, ammonia, and compounds of formula $NW_4^+$, wherein W is $C_{1-4}$ alkyl.

Examples of salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylproprionate, picrate, pivalate, propionate, succinate, tartrate, thiocyanate, tosylate and undecanoate. Other examples of salts include anions of the compounds of the present invention compounded with a suitable cation such as $Na^+$, $NH_4^+$, and $NW_4^+$ (wherein W is a $C_{1-4}$ alkyl group).

For therapeutic use, salts of the compounds of the present invention will be pharmaceutically acceptable. However, salts of acids and bases which are non-pharmaceutically acceptable may also find use, for example, in the preparation or purification of a pharmaceutically acceptable compound.

Esters of the compounds identified by the method of this invention include carboxylic acid esters (i.e., —O—C(=O)R) obtained by esterification of the 2'-, 3'- and/or 5'-hydroxy groups, in which R is selected from (1) straight or branched chain alkyl (for example, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy or amino); (2) sulfonate esters, such as alkylsulfonyl (for example, methanesulfonyl) or aralkylsulfonyl; (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di-($C_{6-24}$)acyl glycerol. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group. Examples of lyxo-furanosyl compound derivatives of the present invention include, for example, those with chemically protected hydroxyl groups (e.g., with O-acetyl groups), such as 2'-O-acetyl-lyxo-furanosyl; 3'-O-acetyl-lyxo-furanosyl; 5'-O-acetyl-lyxo-furanosyl; 2',3'-di-O-acetyl-lyxo-furanosyl and 2',3',5'-tri-O-acetyl-lyxo-furanosyl.

Ethers of the compounds of the present invention include methyl, ethyl, propyl, butyl, isobutyl, and sec-butyl ethers.

Compounds useful in the methods of this invention can be described as the L and D isomers of compounds having one of the following structures:

Formula A

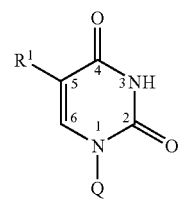

Formulae B

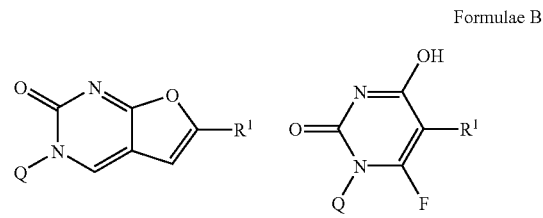

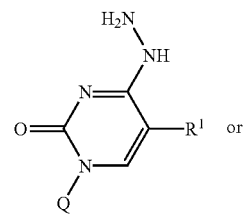 or

-continued

Formula C

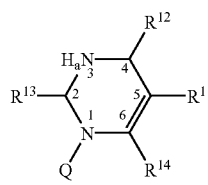

or tautomers thereof, wherein in Formula C, $R^{12}$ or $R^{13}$ may be the same or different and are selected from the group consisting of oxo, OH or $NHNH_2$, wherein a is 0 or 1, providing that if a is 0 and $R^{13}$ is oxo, then a double bond exits between position 3 and 4 and $R^{12}$ is $NHNH_2$; further providing that if a is 0 and $R^{12}$ is oxo, then a double bond exists between position 2 and 3 and $R^{13}$ is $NHNH_2$; further providing that if a is 1, then $R^{12}$ and $R^{13}$ are both oxo.

While not wishing to be bound by any theory, in one aspect of the above formulae (A, B and C), $R^1$ (at the 5-position) is or contains a leaving group which is a chemical entity that has a molecular dimension and electrophilicity compatible with extraction from the pyrimidine ring by an endogenous, intracellular enzyme (e.g., thymidylate synthase). An embodiment for the substituent in the $R^1$ position is one that could undergo an allylic interchange.

Another example is an alkenyl group of the formula, i.e., $(-CH=CH)_n-R^4$, wherein n is 0 or an integer from 1 to 10, and $R^4$ is a halogen such as I or Br, CN or mercury, or alternatively, $R^1$ is or contains a group selected from hydrogen, alkyl, alkene, alkyne, hydroxy, —O-alkyl,—O-aryl, O-heteroaryl, —S-alkyl, —S-aryl, a cyanide, cyanate, thiocyanate halovinyl group, halomercuric group, —S-heteroaryl, —$NH_2$, —NH-alkyl, —N(alkyl)$_2$, —NHCHO, —NHOH, —NHO-alkyl, $NH_2CONHO$—, and $NHNH_2$. For example, when n is 0 or an integer from 1 to 10, $R^4$ is $CH_2$-O—A, wherein A is a

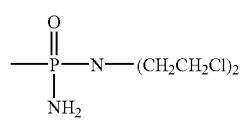

phosphoramide derivative, or a compound of the formula:

Alternatively, in the above formulae (A, B or C), $R^1$ can be a moiety of the formula:

Formula D

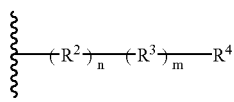

wherein, $R^4$ is a toxophore.

In one aspect of Formula D, $R^2$ is or contains a divalent electron conduit moiety. In one embodiment, $R^2$ is or contains a mono- or polyunsaturated electron conduit acting to conduct electrons away from the pyrimidine ring and toward $R^4$. In another embodiment, $R^2$ is selected from the group consisting of an unsaturated hydrocarbyl group, an aromatic hydrocarbyl group comprising one or more unsaturated hydrocarbyl groups, and a heteroaromatic group comprising one or more unsaturated hydrocarbyl groups.

In a yet further aspect, m is 0 and $R^2$ is selected from the group consisting of:

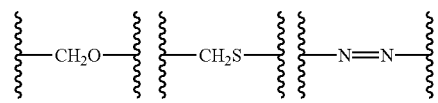

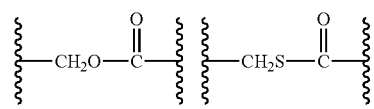

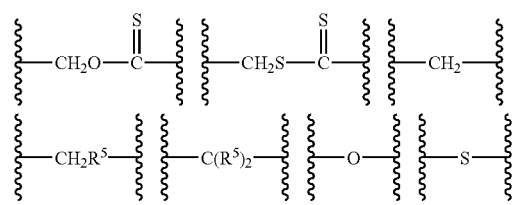

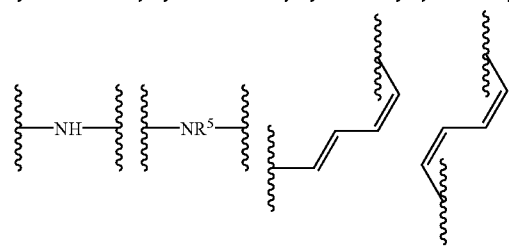

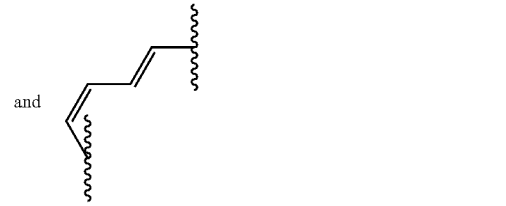

and wherein $R^5$ is independently the same or different and is selected from the group consisting of a linear or branched alkyl group having from 1 to 10 carbon atoms, a cycloalkyl group having from 3 to 10 carbon atoms, CN and a halogen.

In one embodiment of Formula D, $R^2$ is an unsaturated hydrocarbyl group having a structure selected from the group consisting of:

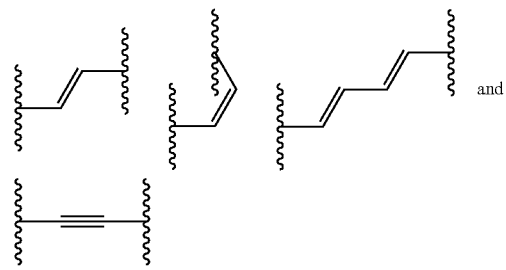

In another embodiment of Formula D, $R^2$ is an aromatic hydrocarbyl group having a structure selected from the group consisting of:

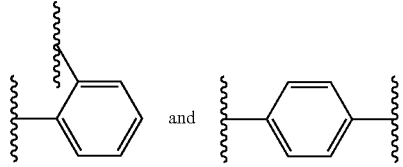

In yet another embodiment of Formula D, $R^2$ is a heteroaromatic group having a structure selected from the group consisting of:

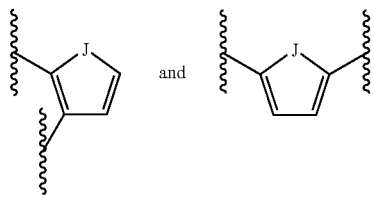

wherein J is a heteroatom, such as —O—, —S—, or —Se—, or a heteroatom group, such as —NH— or —NR$^{ALK}$—, where R$^{ALK}$ is a linear or branched alkyl having 1 to 10 carbon atoms or a cycloalkyl group having 3 to 10 carbon atoms.

In an alternative embodiment of Formula D, $R^3$ is a divalent spacer moiety, also referred to as a spacer unit. Divalent spacers include, but are not limited to, a moiety having a structure:

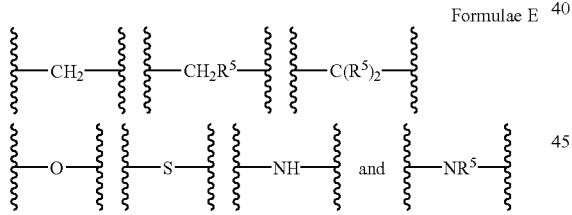

Formulae E wherein $R^5$ is the same or different and is independently a linear or branched alkyl group having from 1 to 10 carbon atoms, or a cycloalkyl group having from 3 to 10 carbon atoms.

In an alternative aspect of Formula D, $R^3$ is a divalent spacer moiety having a structure selected from the group consisting of:

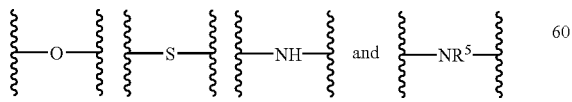

In yet another aspect of Formula D, $R^2$ and $R^3$, taken together form a structure selected from the group consisting of:

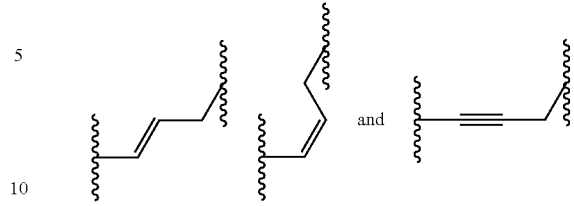

In one embodiment, $R^4$ ($R^4$ in Formula D or $R^1$ in Formulae A, B or C) is or contains a leaving group that is activated or released by an intracellular enzyme. In one embodiment, $R^4$ is or contains a group having a structure selected from the group consisting of F, Cl, Br, I, CN, $SO_3H$, $CO_2H$, $CO_2CH_2CH_3$, $CO_2CH_3$, $SI(CH_3)_3$, CHO, $NO_2$, $CF_3$, $CCl_3$, $CH=C(R^{15})_2$ and a derivative of cisplatin, such as:

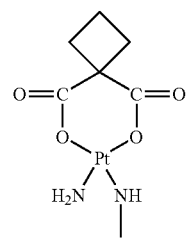

or a substituent selected from the structures:

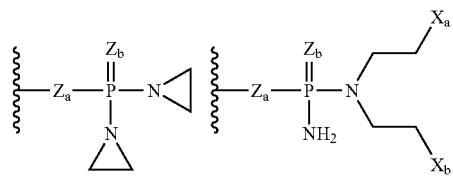

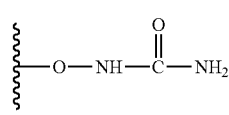

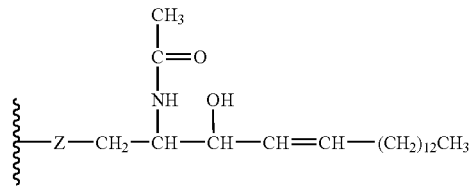

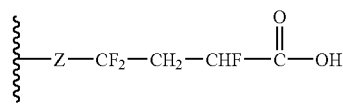

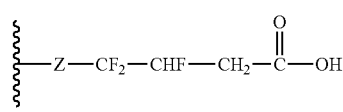

-continued

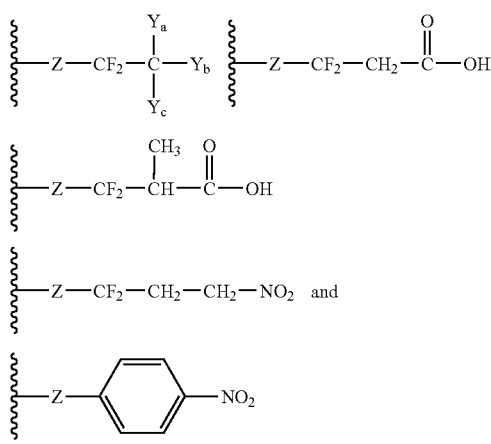

wherein $X_a$ and $X_b$ are independently the same or different and are selected from the group consisting of Cl, Br, I, and a potent leaving group and wherein $Y_a$, $Y_b$ or $Y_c$ are independently the same or different and are hydrogen or F and wherein Z, $Z_a$ and $Z_b$ are independently the same or different and are selected from the group consisting of O and S; and with respect to Formula C, $R^{14}$ is hydrogen or F, providing if $R^{14}$ is F, then a is 1 and $R^{12}$ and $R^{13}$ are both oxo.

Q is a 5' phosphoramidate derivative, analog or pharmaceutically acceptable salt of a sugar as defined above, e.g., Q is selected from the group consisting of:

Formulae F

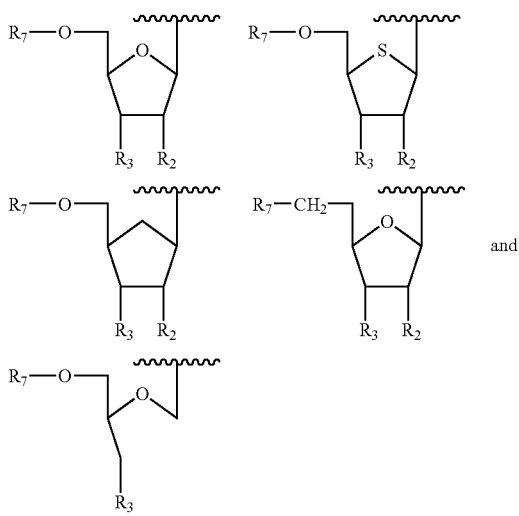

and

In the above Formula F, $R_2$ and $R_3$ are independently the same or different and are selected from the group consisting of Br, Cl, F, I, H, OH, OC(=O)CH$_3$, —O- and —O—Rg, wherein Rg is a hydroxyl protecting group other than acetyl. $R_7$ is attached to Q at the 5' position of Q and is an amino acid containing phosphoramidate group. Any of the members of Formulae F may be in any enantiomeric, diasteriomeric, or stereoisomeric form, including D-form, L-form, α-anomeric form, and β-anomeric form.

In a specific embodiment, Q has the formula:

Formula G

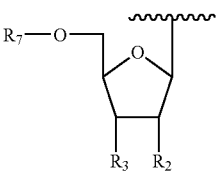

wherein $R_2$ and $R_3$ are independently the same or different and are independently H, —OH, —OC(=O)CH$_3$, or —O-Rg, wherein Rg is a hydroxyl protecting group other than acetyl. $R_7$ is as defined above.

In a further specific embodiment, Q has the following structure:

Formula H

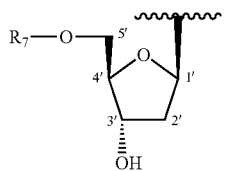

In each of Formulae F, G, or H, $R_7$ is a phosphoramidate group derived from an amino acid, including, for example, the twenty naturally occurring amino acids, e.g., alanine and tryptophan. In one embodiment, $R_7$ is a phosphoramidate group derived from tryptophan, for example a group having the structure:

Formula I

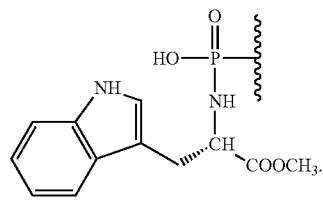

The above group, and methods for its preparation, are described in Abraham et al., (1996).

In another embodiment, $R_7$ is or contains a group having the structure:

Formula J

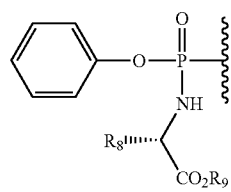

wherein $R_8$ is a side chain of any amino acid, its derivative, its analogue or its isomer and wherein $R_9$ is selected from the group consisting of hydrogen, an unbranched or branched acyclic alkyl group containing from 1 to 5 carbons, a cyclic saturated alkyl group containing from 3 to 8 carbons, an aryl group and an adamantyl group. In one aspect, $R_8$ is a side chain of any amino acid, its derivative, its analogue or its isomer with the proviso that when $R_8$ is alanine, $R_9$ is not selected from the group consisting of methyl, ethyl, methyl-tert-butyl, iso-propyl, methyl-cyclopropyl, cyclohexyl and benzyl. In a further aspect, $R_8$ is a side chain of any amino acid, its derivative, its analogue or its isomer with the proviso that when $R_9$ is methyl, $R_8$ is not selected from the group consisting of tryptophan, valine, glycine, leucine, phenylalanine and aspartic acid. In a further aspect, $R_8$ is a side chain of alanine and $R_9$ is selected from the group consisting of benzyl, methyl-cyclopropyl, cyclohexyl, iso-propyl, methyl-tert-butyl, cycloheptyl, cyclooctyl and methyl-adamantyl. In a further aspect, $R_8$ is a side chain of alanine and $R_9$ is selected from the group consisting of cycloheptyl, cyclooctyl and methyl-adamantyl. In a further aspect, $R_8$ is a side chain of tryptophan and $R_9$ is methyl.

In another aspect, $R_8$ and $R_9$ are defined as above, wherein the nucleoside or its analog thereof is 2'-deoxy. In one aspect, when $R_8$ is alanine and $R_9$ is methyl, then $R_1$ is not bromovinyl. In another aspect, when $R_8$ is alanine, $R_9$ is methyl and $R_1$ is not bromovinyl, then the nucleoside or analog is not 2'-deoxy.

In one embodiment, $R_7$ is a phosphoramidate group derived from alanine, e.g., a group having the structure:

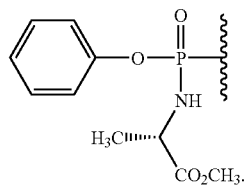

The above group, and methods for its preparation, are described in McGuigan et al. (1993) and McGuigan et al. (1996).

In further embodiments, $R_7$ is or contains a substituent selected from the group consisting of:

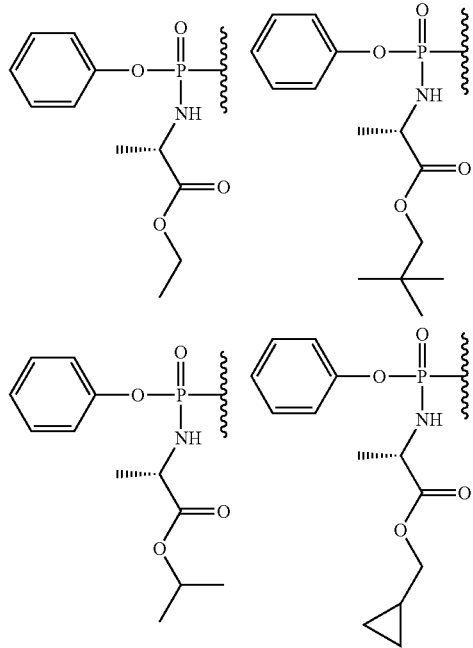

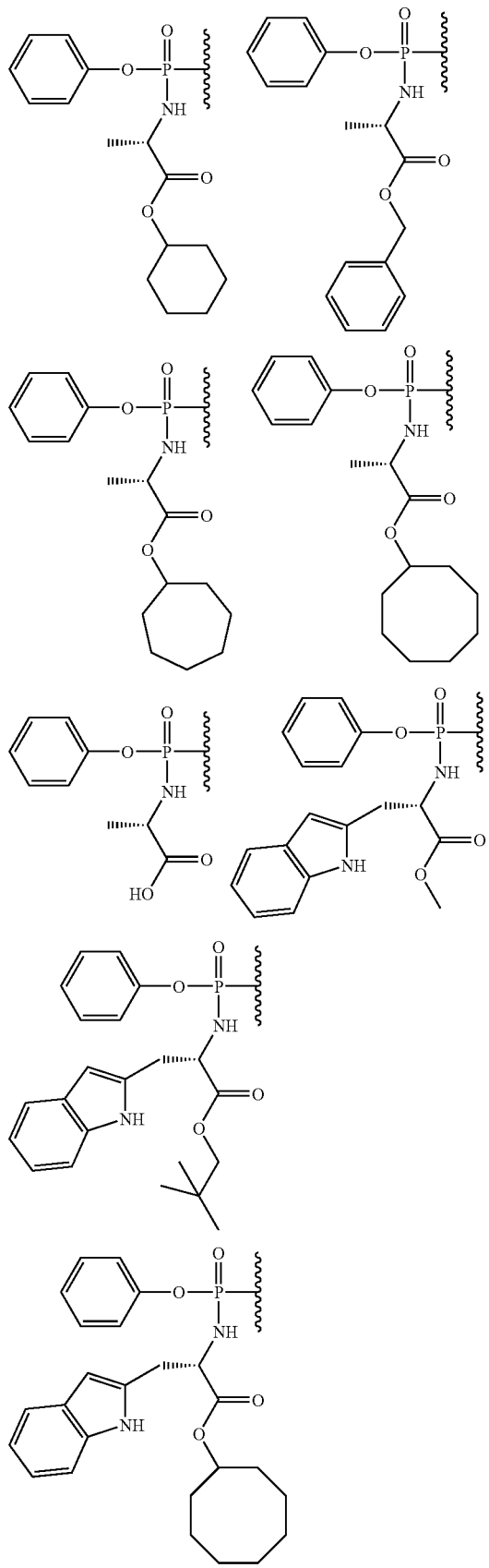

-continued

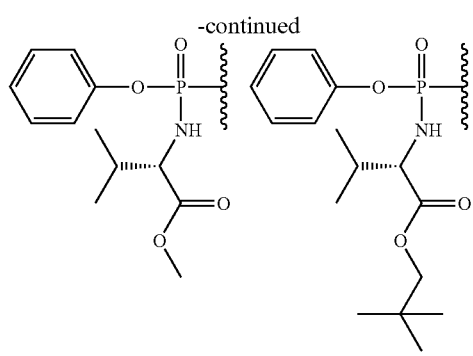

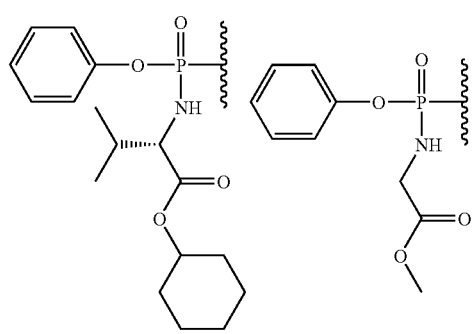

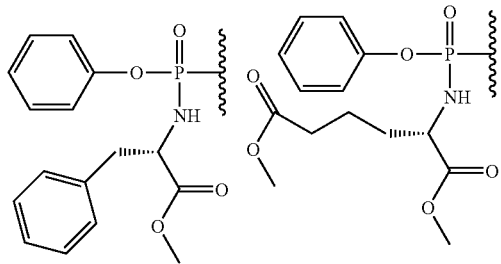

It is intended, although not always stated that the compounds of this invention may be in any enantiomeric, diastereomeric, or stereoisomeric form, including, D-form, L-form, α-anomeric form, and β-anomeric forms. The compounds may be in a salt form, or in a protected or prodrug form, or a combination thereof, for example, as a salt, an ether, or an ester.

In a further aspect, $R^7$ is as defined above and $R_1$ is a bromovinyl group or a group shown in Table 2, below.

Specific compounds having the L or D structures are shown in Table 2, below. Compounds are identified by structure and a numerical designation.

TABLE 2

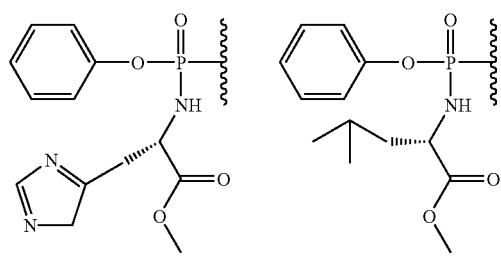

| $R_1$ | |
|---|---|
| Br (propenyl) | NB 1011 |
| Br,Br (dibromo diene) | NB 1012 |
| Cl (propenyl) | NB 1013 |
| —CF₃ | NB 1014 |
| CO₂CH₂CH₃ (dienyl ester) | NB 1016 |
| Br (bromodienyl) | NB 1017 |
| —≡—SiMe₃ | NB 1018 |
| —≡—H | NB 1019 |
| —≡—C₈H₁₇ | — |
| —C₈H₁₇ | — |

Further embodiments of compounds of this invention are provided below.

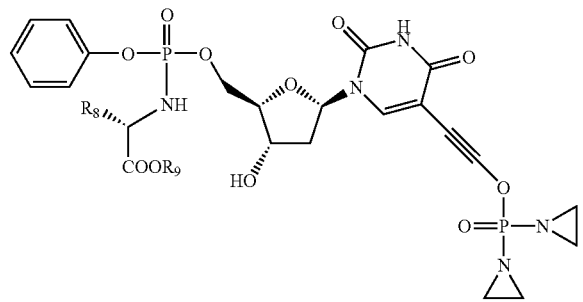

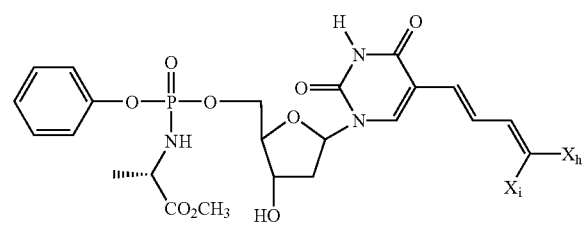

wherein $X_f$ and $X_g$ are independently the same or different and are selected from the group consisting of Cl, Br, I, and CN. In a preferred embodiment, $X_f$ and $X_g$ are the same and are each is Cl or Br.

A compound having the structure of the formula:

wherein $X_h$ and $X_i$ are independently the same or different and are selected from the group consisting of Cl, Br, I, and CN. In a preferred embodiment, $X_h$ and $X_i$ are independently the same or different and are Cl or Br and in a more preferred embodiment, $X_h$ and $X_i$ are both Br.

A compound having the structure:

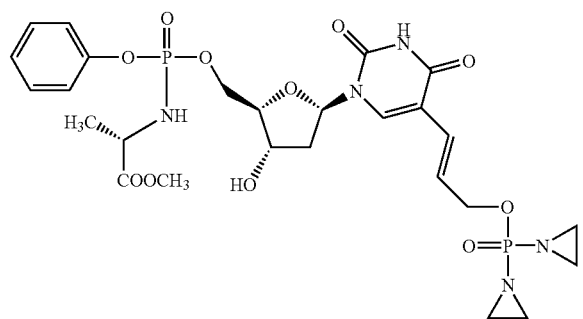

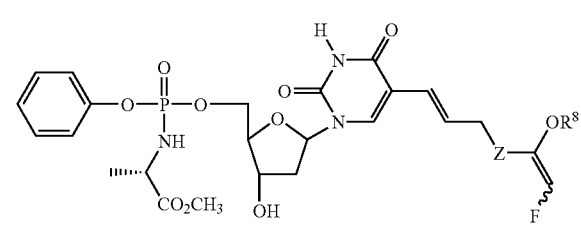

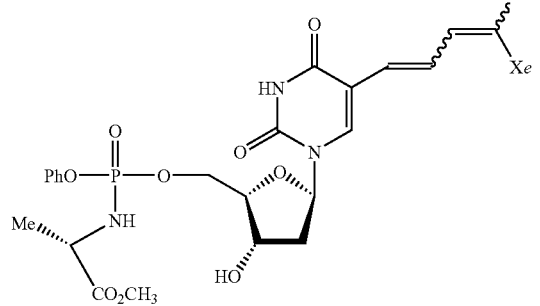

wherein $X_d$ and $X_e$ are independently the same or different and are selected from the group consisting of Cl, Br, I, and CN. In a more preferred aspect, $X_d$ is Cl or Br and $X_e$ is hydrogen.

A compound having the structure:

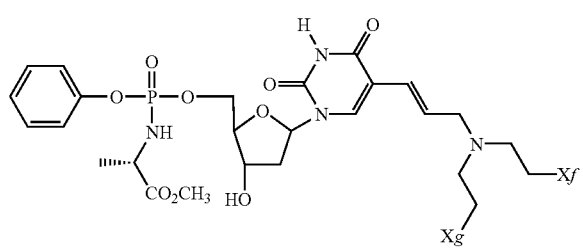

wherein $R^8$ is a lower straight or branched chain alkyl.

A compound having the structure:

wherein $R^8$ and $R^9$ are lower straight or branched chain alkyls and $R^{10}$ is hydrogen or $CH_3$.

A compound having the structure:

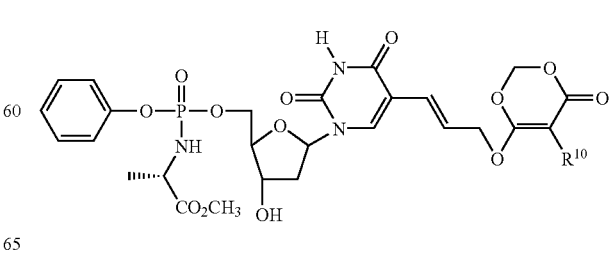

wherein $R^{10}$ is hydrogen or $CH_3$.

A compound having the structure:

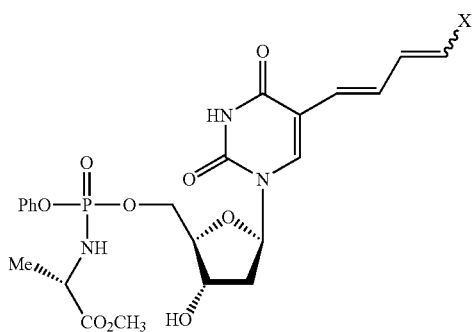

wherein X is selected from the group consisting of CO$_2$Et, Cl, and Br.

A compound having the structure:

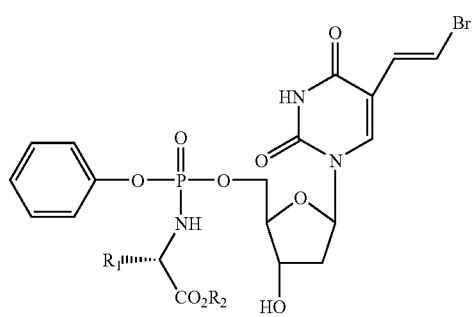

wherein R$_1$ is a side chain of any naturally occurring amino acid, its analogue or its isomer; and wherein R$_2$ is selected from the group consisting of hydrogen, an unbranched or branched acyclic alkyl group containing from 1 to 5 carbons, a cyclic saturated alkyl group containing from 3 to 8 carbons and a benzyl group and its pharmaceutically acceptable salts.

A compound having the structure:

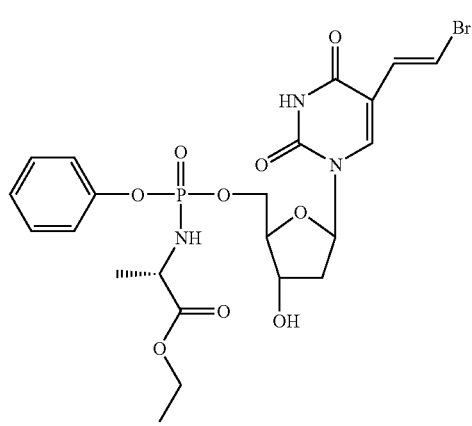

-continued

A compound having the structure:

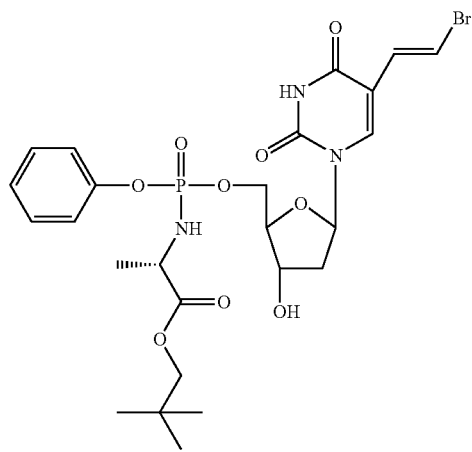

A compound having the structure:

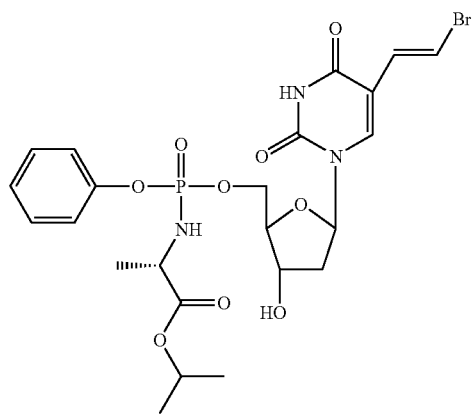

A compound having the structure:

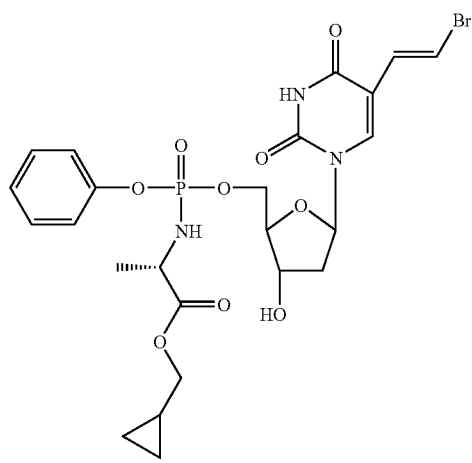

A compound having the structure:
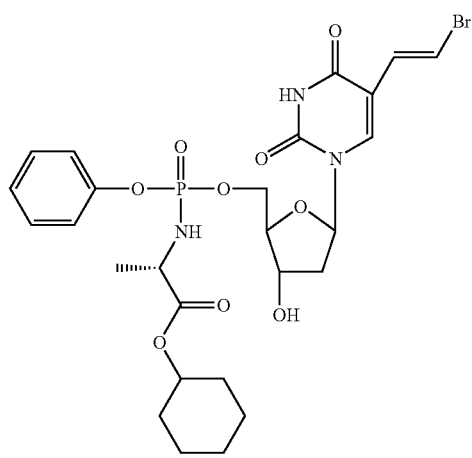
A compound having the structure:
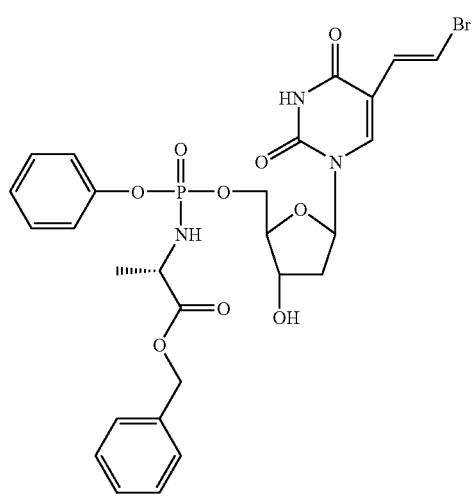
A compound having the structure:
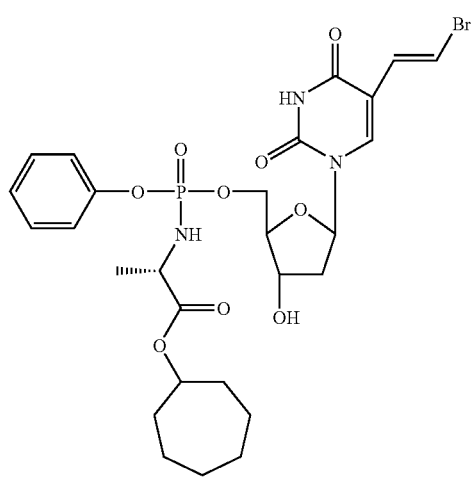
A compound having the structure:
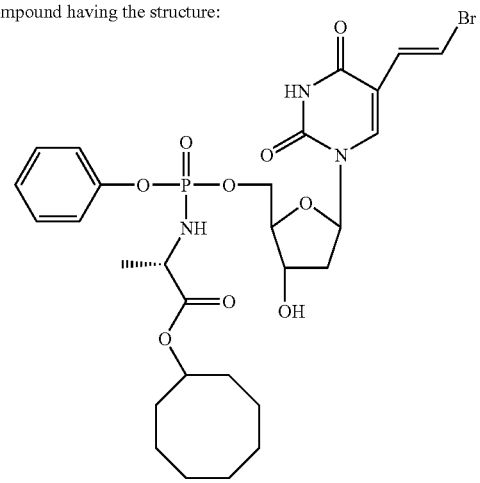
A compound having the structure:
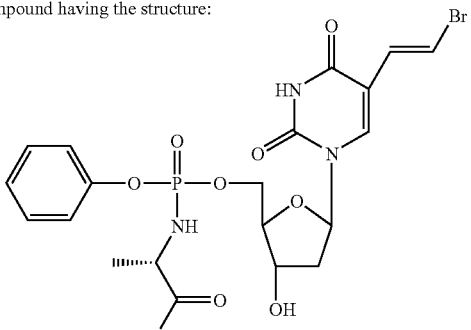
A compound having the structure:
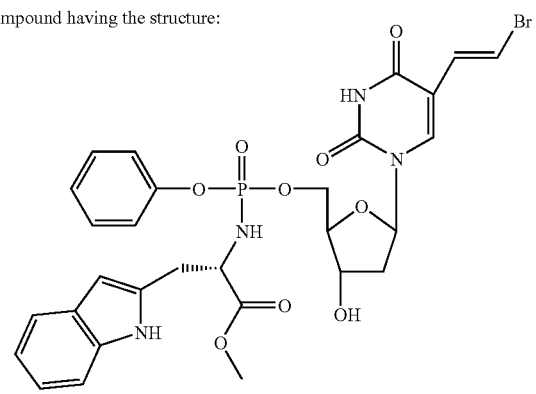
A compound having the structure:
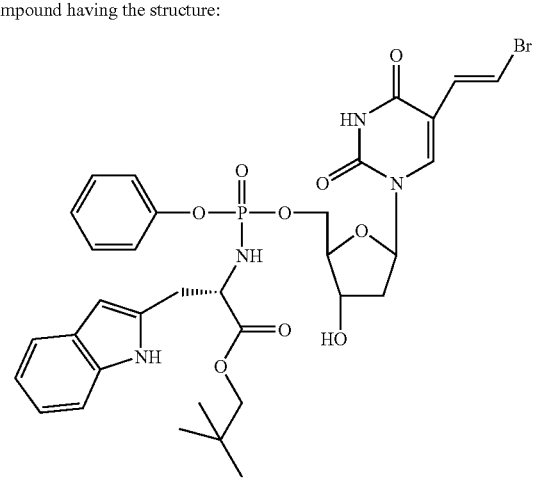

A compound having the structure:
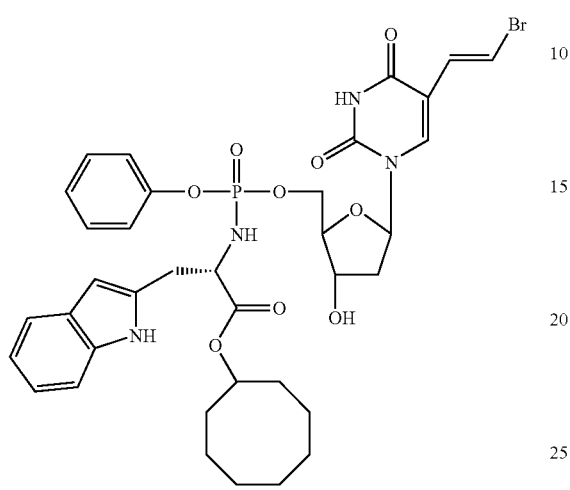
A compound having the structure:
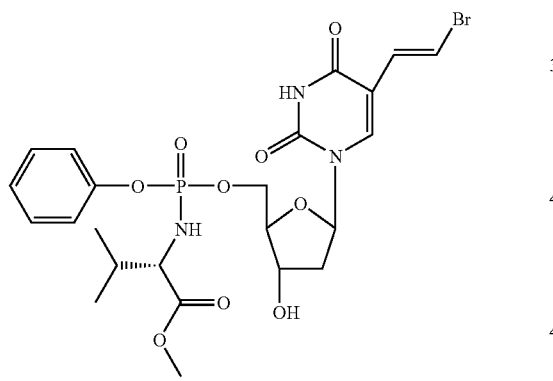
A compound having the structure:
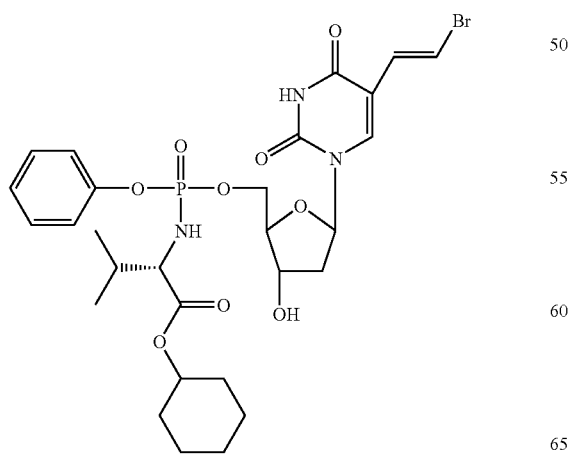
A compound having the structure:
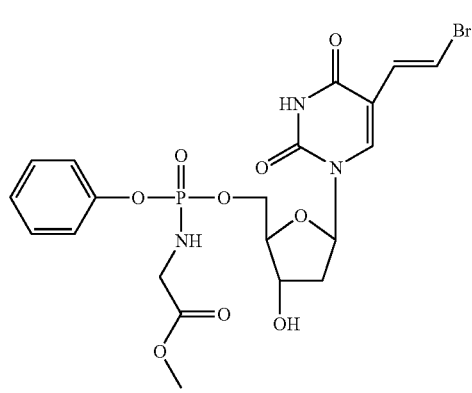
A compound having the structure:
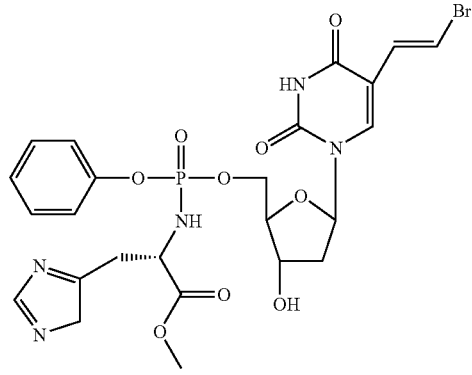
A compound having the structure:
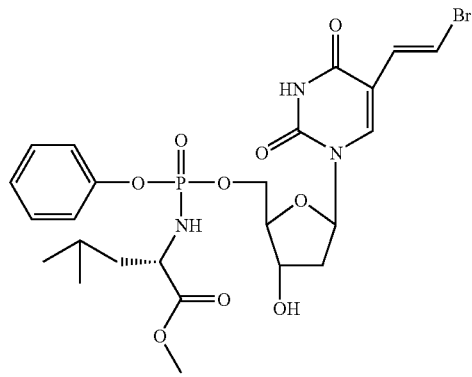

-continued

A compound having the structure:

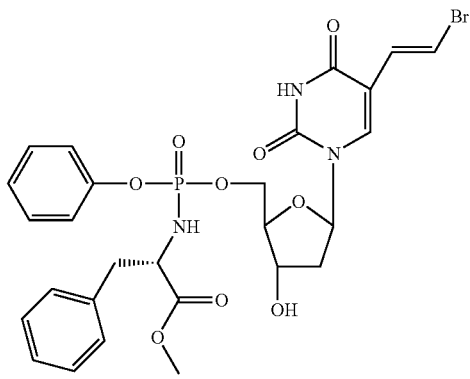

A compound having the structure:

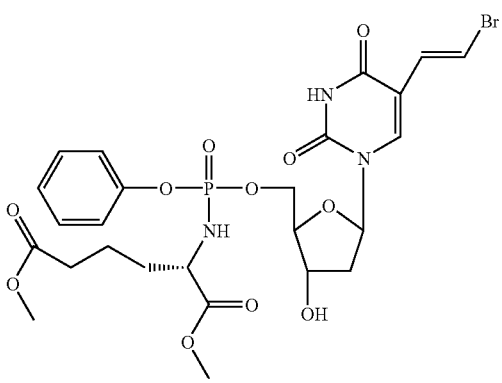

The compounds can be combined with a carrier, such as a pharmaceutically acceptable carrier, for use in vitro and in vivo.

Formulations for In Vivo Administration

While it is possible for the composition ingredient to be administered alone, it is preferable to present it as a pharmaceutical formulation comprising at least one active ingredient, as defined above, together with one or more pharmaceutically acceptable carriers therefore and optionally other therapeutic agents. Each carrier must be "acceptable" in the sense of being compatible with the other ingredients of the formulation and not injurious to the patient.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin or sucrose and acacia; and mouthwashes comprising the active ingredient in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with active ingredients and optionally one or more excipients or diluents.

For diseases of the eye or other external tissues, e.g., mouth and skin, the formulations are preferably applied as a topical ointment or cream containing the active ingredient in an amount of, for example, about 0.075 to about 20% w/w, preferably about 0.2 to about 25% w/w and most preferably about 0.5 to about 10% w/w. When formulated in an ointment, the composition may be employed with either a paraffinic or a water-miscible ointment base. Alternatively, the ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound that enhances absorption or penetration of the ingredients through the skin or other affected areas. Examples of such dermal penetration enhancers include dimethylsulfoxide and related analogs.

The oily phase of the emulsions of this invention may be constituted from known ingredients in a known manner. While this phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier that acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the ingredients. The ingredients are preferably present in such formulation in a concentration of about 0.5 to about 20%, advantageously about 0.5 to about 10%, particularly about 1.5% w/w.

Formulations for rectal administration may be presented as a suppository with a suitable base comprising, for example, cocoa butter or a salicylate.

Formulations suitable for vaginal administration may be presented as suppositories, tampons, creams, gels, pastes, foams or spray formulations containing in addition to the ingredients, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the ingredients.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents.

Compositions of the formula of the present invention may also be presented for the use in the form of veterinary formulations, which may be prepared by methods that are conventional in the art.

Methods of Treatment

Pathological cells, tissues and pathologies characterized by hyperproliferative cells are treated by contacting the cells or tissue associated with these pathologies with an effective amount of a compound of this invention. The contacting can be any one or more of in vitro, ex vivo and in vivo.

When practiced in vivo in a subject other than a human patient such as a mouse, the method provides an animal model for use in discovering alternative agents and therapies.

In a human patient, the method treats pathologies characterized by hyperproliferative cells, e.g., cancer, infectious disease, an autoimmune disorder or inflammatory condition. Methods for detecting clinical and sub-clinical evidence of effective therapy are known in the art and described herein. In each of these methods, an effective amount of a compound of this invention is delivered or administered to the subject, e.g., mouse or human patient.

In one aspect, this invention is directed to methods for inhibiting the proliferation or growth of an infectious agent or a cell infected with the agent by contacting the agent or infected cell with a compound of this invention. The methods and compositions of this invention are useful to preferentially inhibit the growth or proliferation of cells that express or contain activating enzyme, for example microbial cells, virally infected cells or cells infected with other pathogens. Overexpression of the enzyme is not required, as specificity is related to the species-specificity of the compound to the activating enzyme expressed by the pathogen. The activating enzyme may or may not be expressed by the host cell. However, even if the cell expresses its own version of the enzyme, the compound is selective on the basis that it is preferentially activated by the version of the enzyme expressed by the infectious agent as compared to the version of the enzyme expressed by the host cell. The activating enzyme can be the wild-type or a mutated version which has developed resistance to prior art therapeutics (Hooker, et al. (1996)).

Examples of activating enzymes that are selective targets for the compounds and methods of this invention include, but are not limited to, thymidylate synthase (TS), dihydrofolate reductase (DHFR) and β-lactamase activating enzymes.

The concepts of this invention are illustrated using the activating enzyme thymidylate synthase and its expression in human tumor cells. However, the use of TS is merely illustrative and the claims are not to be construed as limited to systems which target TS. Thymidylate synthase was used herein as the target,. activating enzyme because of the high degree of characterization of its structure and function (Carreras and Santi (1995)), the fact that it is encoded by a single gene, not a gene family (compare for example the family of enzymes noted as glutathione-S-transferase (GST)). In addition, TS overexpression is the result of acquired resistance to chemotherapeutics. Similarly, in one embodiment, the activating enzyme can be expressed as a result of resistance to prior therapy.

Other target activating enzymes include, but are not limited to viral reverse transcriptases and proteases. Examples of viruses that encode these enzymes include the retroviruses (eg. HIV-1, both enzymes, see Turner B. G. and Summers M. F. (1999)), the picornaviruses (eg., Hepatitis A virus, Wang Q. M. (1999)), and Hepatitis C virus (Kwong A. D. et al. (1999)). Early clinical success observed with anti-HIV1 reverse transciptase and protease inhibitors (reviewed by Shafer R. W. and Vuitton D. A. (1999)) has been tempered by the development of resistance, largely due to mutations in the virally-enoded enzymes (Catucci, M. et al. (1999); Mahalingam, B. et al. (1999); and Palmer, S. et al. (1999)). Highly drug-resistant HIV-1 clinical isolates are cross-resistant to many anti-retroviral compounds in current clinical development. Hooker et al. (1996). In these cases of resistance, the viral enzymes retain their catalytic activity because the mutated version of the enzyme retains the structure of the wild-type active site of the enzyme. The compounds of this invention are specifically designed to interact with the active site and be converted by this interaction into a toxin. Accordingly, the drug resistant viral infections are sensitive to the compounds of this invention that require the activating enzyme to generate toxin in the infected cell. NB1011 1 is an example of such a compound, directed against TS expressed by mammalian and human cells as well as pathogens.

Co-Administration

Co-administration of these compounds with other agents may provide unexpected synergistic therapeutic benefit. In the co-administration methods, the compounds are also useful in reducing deleterious side-effects of known therapies and therapeutic agents, as well as yet to be discovered therapies and therapeutic agents. In one aspect, the compounds are combined with a nucleoside transport inhibitor. Suitable nucleoside transport inhibitors include one or more selected from the group consisting of dipyridamole (DP), p-nitrobenzylthioinosine (NBMPR), 6-benzylaminopurine, 2',3'-dideoxyguanosine, 8-bromoadenine, 9-[(2-hydroxyethoxy) methyl]guanine (Acyclovir), 9-[(1,3-dihydroxy-2-propoxy) methyl]guanine (Ganciclovir), adenine, hypoxanthine, allopurinol, dilazep, cytochalasin B, lidoflaxine, mioflazine, phloretin, phloridzine, and benzylisoquinoline alkaloids.

Suitable benzylisoquinoline alkaloids are selected from the group consisting of papaverine, ethaverine, laudanosine, noscarpine, and berberine. Additional operative combinations include, but are not limited to agents or drugs that neutralize or prevent the production of tumor necrosis factor-α (TNF-α) such as an anti-TNF-α antibody or soluble TNF-α receptor that treat or ameliorate the symptoms associated with autoimmune diseases.

Other examples include, but are not limited to corticosteriods, non-steroidal anti-inflammatory drugs (N-SAIDS), and anti-rheumatic drugs.

The use of operative combinations is contemplated to provide therapeutic combinations that may lower total dosage of each component than may be required when each individual therapeutic method, compound or drug is used alone. A reduction in adverse effects may also be noted. Thus, the present invention also includes methods involving co-administration of the compounds described herein with one or more additional active agents or methods. Indeed, it is a further aspect of this invention to provide methods for enhancing other therapies and/or pharmaceutical compositions by co-administering a compound of this invention. In co-administration procedures, the agents may be administered concurrently or sequentially. In one embodiment, the compounds described herein are administered prior to the other active agent(s), therapy or therapies. The pharmaceutical formulations and modes of administration may be any of those described herein or known to those of skill in the art.

In another aspect, the invention provides a method to enhance the cytotoxicity of a compound of this invention against a pathological tissue or cell, containing contacting the cell or tissue with an effective amount of a nucleoside inhibitor compound. It further provides a methods to inhibit the growth of a pathological tissue or, e.g., a cell hyperproliferative cell by contacting the cell with an effective amount of a composition comprising an one or more compounds of this invention.

Reversing Resistance

Resistance to chemotherapeutics can be reversed by contacting the resistant cell with an effective amount of a compound of this invention, in vitro or in vivo. Subsequent to successful treatment, the prior (or original chemotherapeutic) can be re-utilized.

Use of Compounds for Preparing Medicaments

The compounds of the present invention are also useful in the preparation of medicaments to treat a variety of pathologies, e.g., infectious diseases, cancers, autoimmune diseases or inflammatory conditions. The methods and techniques for preparing medicaments of a compound are known in the art. For the purpose of illustration only, pharmaceutical formulations and routes of delivery are detailed below.

Thus, one of skill in the art would readily appreciate that any one or more of the compounds described more fully below, including the many specific embodiments, can be used by applying standard pharmaceutical manufacturing procedures to prepare medicaments to treat the many disorders described herein. Such medicaments can be delivered to the subject by using delivery methods known in the pharmaceutical arts.

Pharmaceutical Delivery

Various delivery systems are known and can be used to administer a compound or an agent of the invention, e.g., encapsulation in liposomes, microparticles, microcapsules, receptor-mediated endocytosis and the like. Methods of delivery include but are not limited to, intra-arterial, intramuscular, intravenous, intranasal, and oral routes. In a specific embodiment, it may be desirable to administer the pharmaceutical compositions locally to the area in need of treatment; this may be achieved by, for example and not by way of limitation, local infusion during surgery, by injection, or by means of a catheter. To determine patients that can be beneficially treated, a tissue sample can be removed from the patient and the cells are assayed for sensitivity to the agent.

Therapeutic amounts can be empirically determined and will vary with the pathology being treated, the subject being treated and the efficacy and toxicity of the compound as well as whether the compound is used alone or in combination with other agents of therapeutic methods. When delivered to an animal, the method is useful to further confirm efficacy of the agent. One example of an animal model is MLR/MpJ-lpr/lpr ("MLR-lpr") (available from Jackson Laboratories, Bal Harbor, Me.). MLR-lpr mice develop systemic autoimmune disease.

Administration in vivo can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician.

Suitable dosage formulations and methods of administering the agents can be readily determined by those of skill in the art. For example, the compounds are administered at about 0.01 mg/kg to about 200 mg/kg, alternatively at about 0.1 mg/kg to about 100 mg/kg, or alternatively at about 0.5 mg/kg to about 50 mg/kg. When the compounds described herein are co-administered with another agent (e.g., as sensitizing agents) or therapy, the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parenteral (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue.

Screening Assays

This invention also provides screening assays to identify therapeutic potentisl of known and new compounds and combinations.

In one aspect, the assay requires contacting a first sample comprising suitable cells or tissue ("control sample") with an effective amount of a compound of this invention and contacting a second sample of the suitable cells or tissue ("test sample") with the agent to be assayed. In a further aspect, the test agent is contacted with a third sample of cells or tissue comprising normal counterpart cells or tissue to the control and test samples and selecting agents that treat the second sample of cells or tissue but does not adversely effect the third sample. For the purpose of the assays described herein, a suitable cell or tissue is one involved in hyperproliferative disorders such as cancer, infectious disease, autoimmune disease or a chronic inflammatory condition. Examples of such include, but are not limited to cell or tissue infected with an infectious agent, cells or tissue obtained by biopsy, blood, breast cells, colon cells, liver cells, synovial fluid, a chondrocyte or an immune cell, such as a T cell, a macrophage, and an NK cell.

In a further aspect, the cells are tissue are characterized by the loss of a native tumor suppressor function. In a yet further aspect, the cells or tissue express a target enzyme or overexpress an endogenous intracellular enzyme. In a still further aspect, the cells or tissue have developed resistance to a drug such as 5-FU.

For example, the compound or agent to be tested can be activated by an endogenous intracellular enzyme that is overexpressed or differentially expressed in a pathological cell as compared to its normal counterpart. An example of such an enzyme includes, but is not limited to thymidylate synthase. Alternatively, a cell genetically modified to differentially express the enzyme or enzymes (containing the appropriate species of enzyme) can be used. Transfection of host cells with polynucleotides encoding the enzyme can be either transient or permanent using procedures well known in the art and described by Chen, L. et al. (1996), Hudziak, R. M. et al. (1988), or Carter, P. et al. (1992), and in the experimental section below. The cells can be prokaryotic (bacterial such as *E. coli*) or eukaryotic. The cells can be mammalian or non-mammalian cells, e.g., mouse cells, rat cells, human cells, fungi (e.g., yeast) or parasites (e.g., Pneumocystis or Leishmania) which cause disease.

Suitable vectors for insertion of the CDNA are commercially available from Stratagene, La Jolla, Calif. and other vendors. The amount of expression can be regulated by the number of copies of the expression cassette introduced into the cell or by varying promoter usage. The level of expression of enzyme in each transfected cell line can be monitored by immunoblot and enzyme assay in cell lysates, using monoclonal or polyclonal antibody previously raised against the enzyme for immunodetection. (Chen, L. et al. (1996)). Enzymatic assays to detect the amount of expressed enzyme also can be performed as reviewed by Carreras, C. W. and Santi, D. V. (1995) or the method described in the experimental section below.

In a further aspect, more than one species of enzyme is used to separately transduce separate host cells, so that the effect of the candidate drug with an enzyme can be simultaneously compared to its effect on another enzyme or a corresponding enzyme from another species.

The compounds and/or compositions can be directly added to the cell culture media and the target cell or the culture media is then assayed for the amount of label released from the candidate compound if the compound contains a detectable label. Alternatively, cellular uptake may be enhanced by packaging the compound into liposomes using the method described in Lasic, D. D. (1996) or combined with cytofectins as described in Lewis, J. G. et al. (1996).

In yet a further aspect, the assay requires at least two cell types, the first being a suitable control cell. The second cell type is of the same type or tissue as the control cell but differs in that pathogenesis toward disease has begun. In one aspect, pathogenesis is determined enzymatically by noting enhanced or over expression of an endogenous intracellular enzyme that activates the compound into a toxic entity. Amplification of genes associated with drug resistance can be detected and monitored by a modified polymerase chain reaction (PCR) as described in Kashini-Sabet, et al. (1988), Houze, T. A. et al. (1997), U.S. Pat. No. 5,085,983, or the method described herein. Acquired drug resistance can be monitored by the detection of cytogenetic abnormalities, such as homogeneous chromosome staining regions and double minute chromosomes both of which are associated with gene amplification. Alternative assays include direct or indirect enzyme activity assays, each of which are associated with gene amplification (e.g., Carreras, C. W. and Santi, D. V. (1995)) and other methodologies (e.g. polymerase chain reaction or immunohistochemistry Pestalozzi, B. C. et al. (1997)). These methods also provides the means to detect subclinical evidence of therapy or a therapeutic effect.

The assays are useful to predict whether a subject will be suitably treated by this invention by delivering a compound or composition to a sample containing the cell to be treated and assaying for treatment which will vary with the pathology. In one aspect, the cell or tissue is obtained from the subject or patient by biopsy. Applicants provide kits for determining whether a pathological cell or a patient will be suitably treated by this therapy by providing at least one composition of this invention and instructions for use.

This invention further provides a method for screening for compounds that are selectively converted to a toxin by an activating enzyme by providing cells that express an activating enzyme and contacting the cells with a candidate compound. At least one test cell expresses the pathogen's version of the enzyme (wild-type or mutated) and another test cell is a cell sample from the host organism which may, or may not express its own version of the enzyme. One then assays for conversion of the compound into toxic agents by the activating enzyme produced by the pathogen. As used herein, the test cells can be prokaryotic or eukaryotic cells infected with the pathogen or alternatively, transformed to express the activating enzyme. For example, a prokaryotic *E. coli* which does not endogenously express the activating enzyme TS is a suitable host cell or target cell. Alternatively, the test cell can be an infected cell isolated from the subject, or a cultured cell infected with the pathogen. The cell can have a control counterpart (lacking the target enzyme), or in a separate embodiment, a counterpart genetically modified to differentially express the target enzyme, or enzymes (containing the appropriate species of target enzyme). More than one species of enzyme can be used to separately transduce separate host cells, so that the effect of the candidate drug on a target enzyme can be simultaneously compared to its effect on another enzyme or a corresponding enzyme from another species.

In another embodiment, a third target cell is used as a positive control because it receives an effective amount of a compound, such as, for example, the compounds shown below, which have been shown to be potent compounds.

In another embodiment, transformed cell lines, such as ras-transformed NIH 3T3 cells (ATCC, 10801 University Blvd., Manassas, Va., 20110-2209, U.S.A.) are engineered to express variable and increasing quantities of the target enzyme of interest from cloned cDNA coding for the enzyme. Transfection is either transient or permanent using procedures well known in the art and described in Sambrook, et al., supra. Suitable vectors for insertion of the cDNA are commercially available from Stratagene, La Jolla, Calif. and other vendors. The level of expression of enzyme in each transfected cell line can be monitored by immunoblot and enzyme assay in cell lysates, using monoclonal or polyclonal antibody previously raised against the enzyme for immuno-detection. The amount of expression can be regulated by the number of copies of the expression cassette introduced into the cell or by varying promoter usage. Enzymatic assays to detect the amount of expressed enzyme also can be performed as reviewed by Carreras and Santi (1995), supra, or the methods described below.

The test cells can be grown in small multi-well plates and is used to detect the biological activity of test compounds. For the purposes of this invention, the successful candidate drug will block the growth or kill the pathogen but leave the control cell type unharmed.

The candidate compound can be directly added to the cell culture media or previously conjugated to a ligand specific to a cell surface receptor and then added to the media. Methods of conjugation for cell specific delivery are well known in the art, see e.g., U.S. Pat. Nos. 5,459,127; 5,264,618; and published patent specification WO 91/17424 (published Nov. 14, 1991). The leaving group of the candidate compound can be detectably labeled, e.g., with tritium. The target cell or the culture media is then assayed for the amount of label released from the candidate compound. Alternatively, cellular uptake may be enhanced by packaging the compound into liposomes using the method described in Lasic, D. D. (1996) or combined with cytofectins as described in Lewis, J. G. et al. (1996).

Compounds, agents and combinations thereof, identified by this method are further provided herein.

In one embodiment, the assay of the effect of the compound is provided by analysis of intracellular metabolites of the compound. In this embodiment, the compound contains a detectable label that is monitored during conversion of the compound to toxic agent by the activating enzyme. In an alternative embodiment, the candidate compound is detectably labeled, e.g., e.g., fluorescent marker, or a radioisotope. In a further aspect, the detectable label comprises at least two or more variable isotopes of the same atom, e.g., bromine. In this embodiment, one can assay for the modification of the compound into toxic byproducts by mass spectrometry of the reaction products. One means to accomplish this assay is by use of mass spectrometry as described in more detail below.

Using the above screen, one also can pre-screen several compounds against samples taken from a subject such as a human patient. One can use the screen to determine the most effective compound and therapy for each pathology or pathogen and subject.

Kits

Applicants also provide kits for determining whether a pathological cell, tissue or patient will be suitably treated by this therapy. Additionally, kits for performance of the assays are provided. These kits contain at least one compound or composition of this invention and instructions for use.

The following examples are intended to illustrate, but not limit, the invention.

MATERIALS AND METHODS

General Synthesis Procedures

Synthesis of Nueleoside Compounds

Synthesis of 5-substituted pyrimidine derivatives can be accomplished by methods known in the art, for example as described in Applicant's patent literature, PCT/US98/16607 and PCT/US99/01332.

One method requires treatment of 5-chloromercuri-2'-deoxyuridine with haloalkyl compounds, haloacetates or haloalkenes in the presence of $Li_2PdCl_4$ to form, through an organopalladium intermediate, the 5-alkyl, 5-acetyl or 5-alkene derivative, respectively (Wataya, Y. et al. (1979) and Bergstrom, D. E. et al. (1984)). Another example of C5-modification of pyrimidine nucleosides and nucleotides is the formation of C5-trans-styryl derivatives by treatment of unprotected nucleotide with mercuric acetate followed by addition of styrene or ring-substituted styrenes in the presence of $Li_2PdCl_4$ (Bigge, et al. (1980)).

Pyrimidine deoxyribonucleoside triphosphates can be derivatized with mercury at the 5 position of the pyrimidine ring by treatment with mercuric acetate in acetate buffer at 50° for 3 hours (Dale, et al. (1973)). Such treatment also would be expected to be effective for modification of monophosphates. Alternatively, a modified triphosphate can be converted enzymatically to a modified monophosphate, for example, by controlled treatment with alkaline phosphatase followed by purification of monophosphate. Other moieties, organic or nonorganic, with molecular properties similar to mercury but with preferred pharmacological properties could be substituted. For general methods for synthesis of substituted pyrimidines see, for example, U.S. Pat. Nos. 4,247,544, 4,267,171, and 4,948,882 and Bergstrom, D. E. et al. (1981). The above methods would also be applicable to the synthesis of derivatives of 5-substituted pyrimidine nucleosides and nucleotides containing sugars other than ribose or 2'-deoxyribose, for example 2'-3'-dideoxyribose, arabinose, furanose, lyxose, pentose, hexose, heptose, and pyranose. An example of a 5-position substituent is the halovinyl group, e.g. (E)-5-(2-bromovinyl)-2'-deoxyuridylate (Barr, P. J. et al. (1983)).

Alternatively, 5-bromodeoxyuridine, 5-iododeoxyuridine, and their monophosphate derivatives are available commercially from Glen Research, Sterling, Va. (USA), Sigma-Aldrich Corporation, St. Louis, Mo. (USA), Moravek Biochemicals, Inc., Brea, Calif. (USA), ICN, Costa Mesa, Calif. (USA) and New England Nuclear, Boston, Mass. (USA). Commercially-available 5-bromodeoxyuridine and 5-iododeoxyuridine can be converted to their monophosphates either chemically or enzymatically, through the action of a kinase enzyme using commercial available reagents from Glen Research, Sterling, Va. (USA) and ICN, Costa Mesa, Calif. (USA). These halogen derivatives could be combined with other substituents to create novel and more potent antimetabolites.

In one aspect, the structures at the 5-position of the compound, analogs and derivatives thereof are referred to as the tethers because they connect a proposed leaving group (toxophore) to the heterocycle.

In another aspect, the tether also contains a spacer between the toxin and the pyrimidine ring can be unsaturated, e.g., vinyl, allyl, and propargyl units are simple, small, and readily accessible synthetically. The vinyl and allyl units have the advantage that they can be prepared in either of two non-interconvertible geometric isomeric forms. Alternatively, synthesis based on the structure of BVdU monophosphate and features a proposed leaving group/toxin directly attached to the terminus of a (poly)vinyl substituent at C5 of the pyrimidine ring. This is the vinyl tether approach. A yet further approach is based on the structure of TFPe-dUMP and is similar to the vinyl tether approach but has a methylene unit separating the proposed leaving group/toxin and the unsaturated unit and thus contains an allyl or propargyl unit. This is the allyl tether approach.

5-Alkylidenated 5,6-dihydrouracils similar in structure to the intermediate common to both the vinyl and allyl tether approach mechanisms have been synthesized recently (Anglada, J. M. et al. 1996). A C5 methylene intermediate produced by the enzyme thymidylate synthase TS was demonstrated by trapping studies (Barrett, J. E. et al. (1998)).

The compounds of Formula B are defined by the structure of the uracil base, or modified uracil base present. These classes are compounds where: 1) the base is a furano-pyrimidinone derivative of uracil; 2) the base is 6-fluoro uracil; 3) the base is 4-hydrazone substituted uracil derivative; and 4) the base is uracil. In one aspect, the uracil or modified uracil derived base is used to synthesize compounds substituted with toxic leaving groups at the 5 position, attached by an electron conduit tether at this 5 position, and including an appropriate spacer moiety between the electron conduit and the toxic leaving group. The compounds can be unphosphorylated, 5' monophosphate, 5' phosphodiester, or 5' protected ("masked") deoxyuridines or comparable derivatives of alternative carbohydrate moieties, as described below. Protected 5-substituted deoxyuridine monophosphate derivatives are those in which the phosphate moiety has been blocked through the attachment of suitable chemical protecting groups. In another embodiment, 5-substituted uracil or uridine derivatives are administered to cells containing nucleoside kinase activity, wherein the 5-substituted uracil/uridine derivative is converted to a 5-substituted uridine monophosphate derivative. Uridine derivatives may also be modified to increase their solubility, cell penetration, and/or ability to cross the blood-brain barrier.

Synthesis of Compounds with Propargyl Tethers

The synthesis of propargylic and allylic alcohol-equipped 2'-deoxyuridines are reported in the literature. For example, Barr, P. J. and Robins, M. J. (1981) and Balzarini, J. et al. (1985).

Both 5-mercuri- (Ruth, J. L. et al. (1978)) and 5-iodouridines (Robins, M. J. et al. (1981)) readily condense with alkenes and alkynes in the presence of a palladium catalyst to afford C5 tether-equipped uridines. The latter route is the more often employed (Robins, M. J. et al. (1982) and Asakura, S. et al. (1988) and (1990)). High-yielding condensations of protected 5-iodo-2'-deoxyuridines with t-butyldimethylsilyl propargyl ether (Graham, D. et al. (1998); De Clercq, E. et al. (1983), methyl propargyl ether (Tolstikov, V. V. et al. (1997)) and even propargyl alcohol itself (Chaudhuri, N. C. et al. (1995) and Goodwin, J. T. et al. (1993)) have been achieved. The 3-hydroxy-1-propynyl substituent introduced by the latter reaction can also be accessed by DIBAL-H reduction of a methacrylate group (Cho, Y. M. et al. (1994)), itself arising from the same Heck reaction used in the synthesis of BVdU. These palladium-catalyzed reactions can be used to condense very long and elaborately-functionalized propargyl-based tethers to 5-iodo-2'-deoxyuridines. (Livak, K. J. et al. (1992) and Hobbs, F. W. Jr. (1989)). (Z)-Allyl-based tethers are generated by the partial hydrogenation of a propargylic precursor over Undiar catalyst (Robins, M. J. et al. (1983)) whereas the (E)-allyl-based ones are best prepared by Heck coupling of an (E)-tributylstannylated ethylene (Crisp, G. T. (1989)).

Closely following the literature procedures, a t-butyldimethylsilyl propargyl ether-equipped 3', 5'-di-O-protected 2'-deoxyuridine (Graham, D. et al. (1998), and De Clercq, E. et al. (1983)) can be prepared and a portion of it, converted to the corresponding (Z)-allyl ether, (Robins, M. J. et al. (1983)) is reduced. Because the TBAF-mediated removal of a TBDMS group generates an oxyanion that can be functionalized in situ, these TBDMS-protected propargyl- and (Z)-allytic-tethered nucleosides can serve as convenient precursors to some of the toxophore-equipped targets. For the (E)-allyl alcohol equipped nucleoside, the known O-tetrahydropyranyl ether derivative is prepared by the literature Heck coupling of an (E)-tributylstannylated ethylene (Crisp, G. T. (1989)).

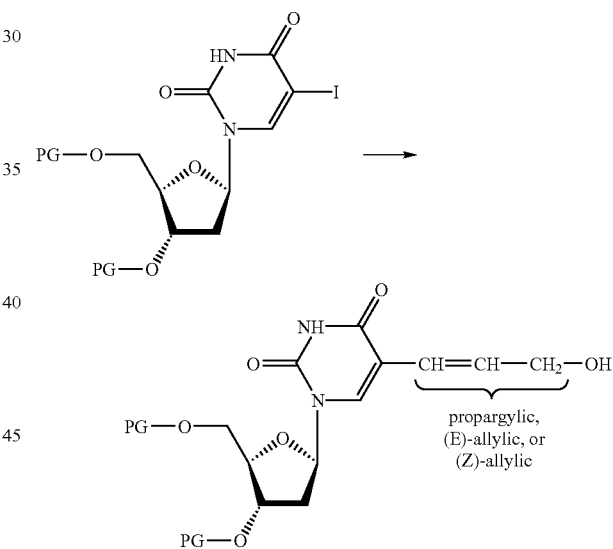

Using a two step literature protocol (Phelps, M. E. et al. (1980) and Hsiao, L. Y. et al. (1981)), the propargylic and (E) and (Z)-allylic alcohols are converted to their corresponding bis-aziridinyl phosphoramidates or thiophosphoramidates.

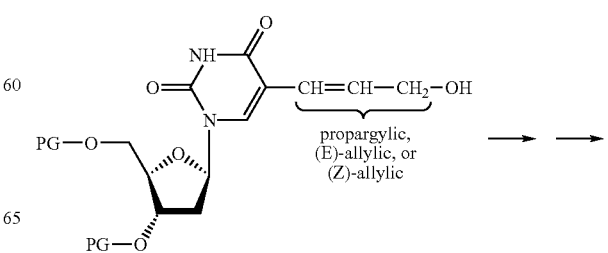

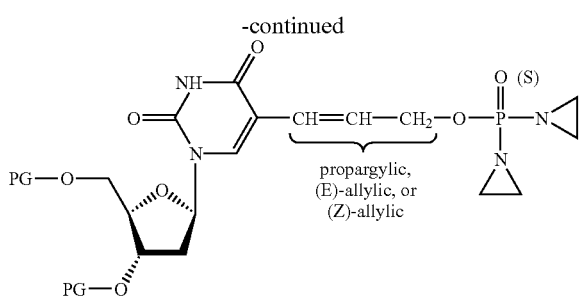

Synthesis of Furano-Pyrimidinones

Synthesis of furano-pyrimidinones begins with synthesis of a C5 propargylic-alcohol-equipped 2'-deoxyuridine. Furano-pyrimidinone compounds are then be formed from the O-tetrahydropyranyl ether derivative described above. Synthesis proceeds by reaction of the second carbon of the propargyl bond with the oxygen attached to the C4 position of the pyrimidine ring to yield a fluorescent furano-pyrimidinone which can be readily separated from the reaction mix. Such compounds provide an additional basis for synthesis of compounds through various combinations of specific electron conduits, spacers and toxic leaving groups.

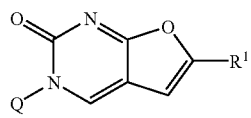

Furo[2,3-d]pyrimidinone nucleosides (represented by the above generic structure) were prepared by condensing 2',3'-di-O-p-toluoyl or 2',3'-di-O-acetyl-5-iodo-2'-deoxyuridine with 1-(tetrahydropyranyloxy)-2-propyne (Jones, R. G. and Mann, M. J. (1953)) under conditions known to promote the formation of these fluorescent compounds (Robins, M. J. et al.(1983)). Base-catalyzed removal of the carbohydrate protecting groups gave the 6-(tetrahydropyran-2-yloxymethyl)-substituted bicyclic nucleoside which was either subjected to standard acidic THP group hydrolysis (TFA in $CH_2Cl_2$) or was regioselectively 5'-phosphoramidated by the same procedure used to prepare BVdU-PA and 5FUdR-PA. After the phosphoramidation, the THP group can be removed by acidic hydrolysis.

Compounds Based on Furano-Pyrimidinones

Examples of synthesis of compounds having a structure of the class shown are as follows.

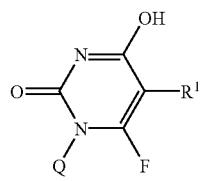

Proposed toxic $R^4$ leaving groups can be attached to the furan-2 methyl alcohol using methods similar to those employed to attach toxic leaving groups to the hydroxyl on the C5 propargyl uridine compound, as explained above. A variety of alternative toxic leaving groups are envisioned. In addition, modifications to the length and composition of the $R^2$ electron conduit component and of the composition of the $R^3$ spacer element are also envisioned.

Compounds based on furano-pyrimidinones can also consist of variously modified phosphoramidates. A method for synthesis of such phosphoramidate compounds is accomplished by reacting a 2-deoxy 3'-hydroxy, 5'-hydroxy unprotected nucleotide with a phosphochloridate in the presence of an HCl scavenger. In one aspect, the phosphochloridate comprises a phosphorus substituent which is derived from an amino acid such as alanine. For example, the phosphochloridate can be phenyl-L-methoxyalanine phosphorochloridate.

C6 Fluoro Uridine and C4 Hydrazone Based Compounds

The introduction of fluorine at the C6 position can be synthesized by following the synthetic descriptions of Krajewskas and Shugar (1982), who describe the synthesis of a number of 6 substituted uracil and uridine analogs.

Chemistry facilitating substitutions at the C4 position of the pyrimidine base are known by those skilled in the art. Examples of literature descriptions include Wallis, et al. (1999); Negishi, et al. (1996), Barbato, et al. (1989) and Holy et al. (1999). These synthetic techniques also enable combinations of substitutions, for instance at the C4 and C5 positions of the pyrimidine ring (Pluta, et al. (1999)) or the C2 and C4 positions of the pyrimidine ring (Zeid, et al. (1999)).

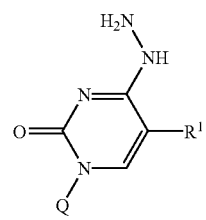

In another embodiment of the invention, compounds are synthesized by addition of alternative electron conduits, spacer moieties and toxic leaving groups to either the C6 fluoro-uridine base or the C4 hydrazone modified pyrimidine. Methods described above for synthesis of 2-deoxyuridine based compounds can again be employed for the synthesis of such molecules.

Synthesis of Nucleoside Phenyl Methoxyalaninyl Phosphoramidates

The use of phosphoramidates as phosphate prodrugs for nucleotides was reported by McGuigan, C. et al. (1993) and McGuigan, C. et al. (1994). The phospharamidates were synthesized by reacting 2',3'-dideoxynucleosides with phenyl methoxyalaninyl phosphorochloridate (PMPC).

Since only one hydroxyl group is present, these reactions usually proceed smoothly. In compounds where more than one hydroxyl group is present, the appropriately protected nucleoside may be required. Since the 5'-OH group of 2'-deoxynucleosides is much less hindered than the 3'-OH group, selective phosphoramidation with PMPC is possible under carefully controlled conditions. Both BVdU and 5FUdR condensed with PMPC in the presence of N-methylimidazole in anhydrous $CH_2Cl_2$ to give the corresponding phosphoramidates. In both cases, the desired product was readily separable from the starting material using column chromatography on silica gel. The synthetic scheme is summarized below.

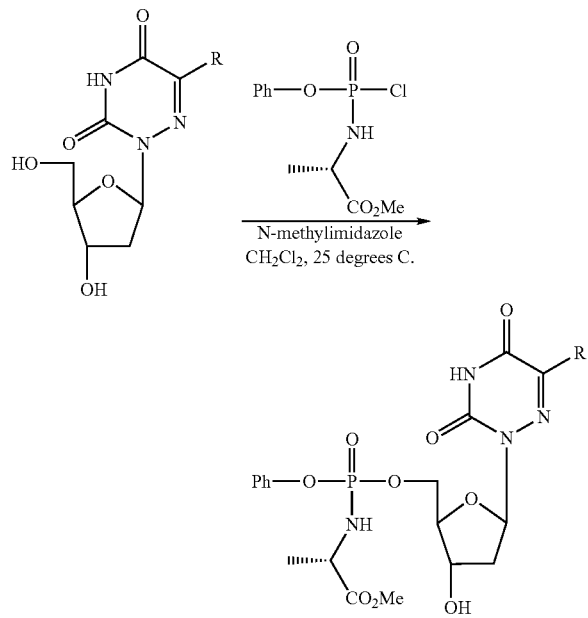

EXAMPLES 1 AND 2

Synthesis of Compounds with Propargyl Tethers

Using the general synthetic procedure described supra, bis-aziridin-1-yl-phosphinic acid 3-[2-deoxyuridin-5-yl]-prop-2-ynyl ester was synthesized and analyzed by $^1$H NMR to yield the following result: $^1$H NMR ((CD$_3$)$_2$SO). Salient features: δ8.28 (d, 1, H6), 6.10 (pseudo-t, 1, H1'), 5.26 (m, exchanges with D$_2$O, 1, 3'-OH), 5.13 (m, exchanges with D$_2$O, 1, 5'-OH), 4.81 (q or dd, 2, propargyl-CH$_2$), 4.24 (m, 1, H3'), 3.57 (m, 2, 5'-CH$_2$), 2.15-2.0 (m, 8, aziridine-CH$_2$).

Bis-aziridin-1-yl-phosphinothioic acid 3-[2-deoxyuridin-5-yl]-prop-2-ynyl ester was also synthesized and analyzed by $^1$H NMR to yield the following result: $^1$H NMR ((CD$_3$)$_2$SO). Salient features: δ8.29 (d, 1, H6), 6.10 (pseudo-t, 1, H1'), 5.22 (m, exchanges with D$_2$O, 1, 3'-OH), 5.10 (m, exchanges with D$_2$O, 1, 5'-OH), 4.88 (q or dd, 2, propargyl-CH$_2$), 4.31 (m, 1, H3'), 3.52 (m, 2, 5'-CH$_2$), 2.15-2.0 (m, 8, aziridine-CH$_2$).

EXAMPLES 3 TO 8

Synthesis of Furano-pyrimidinones

Using the general synthetic procedure described supra, the following compounds were prepared.

Example 3

3-(2-Deoxy-β-D-ribofuranosyl)-6-(tetrahydropyran-2-yloxymethyl)furo[2,3-d]pyrimidin-2(3H)-one. $^1$H NMR ((CD$_3$)$_2$SO) δ8.80 (s, 1, H4), 6.74 (s, 1, H5), 6.16 (pseudo-t, 1, H1'), 5.27 (d, exchanges with D$_2$O, 1, 3'-OH), 5.12 (t, exchanges with D$_2$O, 1, 5'-OH), 4.72 (m, 1, THP-H2), 4.56 (q, 2, CH$_2$OTHP), 3.92 (m, 1, H4'), 3.64 (m, 2, 5'-CH$_2$), 2.40 (m, 1, H2'a), 2.03 (m, 1, H2'b), 1.68 and 1.50 (m, 8, THP). Low-resolution mass spectrum (DCI—NH$_3$) on bis-TMS derivative, m/z 323 (B+TMS+H$^+$), 511 (MH$^+$), 583 (M+TMS$^+$).

Example 4

3-(2-Deoxy-β-D-ribofuranosyl)-6-(hydroxymethyl)furo[2,3-d]pyrimidin-2(3H)-one. $^1$H NMR ((CD$_3$)$_2$SO) δ12.0 (bs, 1, OH), 8.24 (s, 1, H4), 6.53 (s, 1, H5), 5.51 (pseudo-t, 1, H1'), 4.42 (m, 2, CH$_2$OH). Low-resolution mass spectrum (DCI—NH$_3$), m/z 167 (B+2H$^+$), 184 (B+NH$_4^+$).

Example 5

1-[6-(Tetrahydropyran-2-yloxymethyl)furo[2,3-d]pyrimidin-2(3H)-on-3-yl]-2-deoxy-β-D-ribofuranos-5-yl phenyl methoxy-L-alaninylphosphoramidate. $^1$HNMR ((CD3)2SO) complicated due to presence of diastereomers. Salient features: δ8.62 and 8.59 (each s, each 1, H4), 7.4-7.1 (m, 5, PhO), 6.61 and 6.60 (each s, each 1, H5), 6.25 (m, 1, H1'), 4.56 (q, 2, propargyl-CH$_2$), 3.56 and 3.54 (each s, each 3, CO$_2$Me), 2.0 (m, 1, H2'b), 1.22 (m, 3, alaninyl-α-Me). Low-resolution mass spectrum (DCI—NH3), m/z 167 (B+2H$^+$), 184 (B+H$^+$+NH$_4^+$-THP).

Example 6

1-[6-(Hydroxymethyl)furo[2,3-d]pyrimidin-2(3H)-on-3-yl]-2-deoxy-β-D-ribofuranos-5-yl phenyl methoxy-L-alaninylphosphoramidate. $^1$H NMR (CDCl$_3$) complicated due to presence of diastereomers. Salient features: δ8.5 (s, 1, H4), 7.4-7.1 (m, 5, PhO), 6.36 and 6.30 (each s, each 1, H5), 6.23 (m, 1, H1'), 3.67 and 3.65 (each s, each 3, CO$_2$Me), 2.69 (m, 1, H2'a), 2.10 (m, 1, H2'b), 1.35 (m, 3, alaninyl-α-Me). Low-resolution mass spectrum (DCI—NH$_3$), m/z 525 (MH$^+$), 595 (MNH$_4^+$).

Example 7

The 4-nitrophenyl ether derivative of 5-(3-hydroxy-1-propynyl)-2'-deoxyuridine was prepared according to standard ether synthesis as shown below.

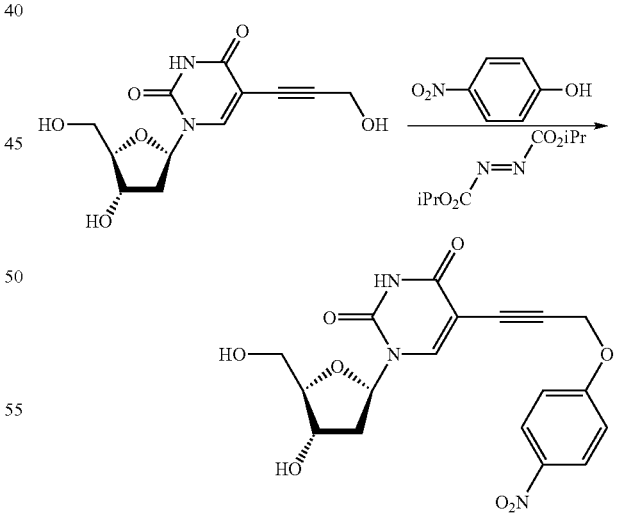

Example 8

5-[3-(4-Nitrophenoxy)-1-propynyl]-2'-deoxyuridine

A solution of pre-dried 5-(3-hydroxy-1-propynyl)-2'-deoxyuridine (Robins, M. J. et al. (1983)) (565 mg, 2 mmol)

in 40 mL of anhydrous THF under argon was treated with 4-nitrophenol (696 mg, 5 mmol), triphenylphosphine (787 mg, 3 mmol), and diisopropyl azodicarboxylate (590 liters, 3 mmol), and the reaction mixture heated at 60° C. until the solution was clear, and then 1 hour longer. The mixture was allowed to cool to 23° C. and then it was evaporated onto $SiO_2$ and purified by chromatography using $MeOH/CH_2Cl_2$ as eluent to afford 107 mg (13%) of the desired ether product: melting point 112-118° C. H NMR ($(CD_3)_2SO$) δ11.65 (s, exchanges with $D_2O$, 1, NH), 8.29 (s, 1, H6), 8.24 (d, J=9.3 Hz, 2, m-ArH), 7.23 (d, J=9.3 Hz, 2, o-ArH), 6.09 (pseudo-t, 1, H1'), 5.17 (s, 2, propargyl-$CH_2$), 4.22 (m, 1, H3'), 3.80 (m, 1, H4'), 3.59 (m, 2, 5'-$CH_2$), 2.13 (pseudo-t, 2, 2'-$CH_2$). Low-resolution mass spectrum ($DCI-NH_3$) onper-trimethylsilyated material, m/z 547 [$M(TMS)_2H^+$], 565 [$M(TMS)_2NH_4^+$], 620 [$M(TMS)_3H^+$].

EXAMPLE 9

5-(4-Carbethoxy-1,3-butadienyl)-2'-dexoyuridine (a) 5-(Carbomethoxyvinyl)-2'-deoxyuridine-3',5'-bis(tetrahydro-2H-pyran-2-yl)ether (I)

A slurry of 5-(carbomethoxyvinyl)-2'-deoxyuridine (3.0 g, 9.6 mmol), 3,4-dihydro-2H-pyran (22 mL, 21.3 mmol) and pyridinium p-toluenesulfonate (PPTS, 0.242 g, 0.96 mmol) in dimethylformamide (DMF, 5 mL) was stirred at 50° C. for 18 hours. The resulting solution was concentrated in vacuo (bath temperature 45° C.) to give a thick, pale yellow oil. The oil was dissolved in EtOAc and the solid was filtered. The solution was again concentrated. The oil obtained was purified by column chromatography on silica gel using 50-75% EtOAc/hexane as eluent to give 3.81 g (85%) of pure product as a colorless oil.

(b) 5-(3-Hydroxyprop-1-enyl)-2'-deoxyuridine-3 ',5'-bis (tetrahydro-2H-pyran-2-yl)ether (II)

A solution of (I) (3.5 g, 7.27 mmol) in $CH_2Cl_2$ (14 mL) was cooled to −78° C. in a dry ice/acetone bath. Diisobutylaluminum hydride (DIBAL-H) in toluene (1.0M, 24 mL, 24.0 mmol) was added dropwise over 2 hours while the temperature was maintained at −78° C. The solution was stirred at −78° C. for an additional 2 hours and MeOH (2.5 mL) was added dropwise to destroy any excess DIBAL-H. The reaction mixture was cannulated into a mixture of 30% citric acid solution (50 mL), ice (25 g) and EtOAc (30 mL) over ca. 20 minutes. The phases were separated and the aqueous phase was extracted with EtOAc (2×25 mL). The combined organic phase was washed with saturated $NaHCO_3$ (20 mL) and brine (20 mL), dried over $MgSO_4$ and concentrated to give 3.288 g (100%) of colorless oil (c) 5-(3-Oxoprop-1-enyl)-2'-deoxyuridine-3',5'-bis(tetrahydro-2H-pyran-2-yl)ether (III)

To a solution of crude (II) obtained from above (1.988 g, 4.4 mmol) in $CH_2Cl_2$ (9 mL) was added solid pyridinium dichromate (PDC; 1.82 g, 4.8 mmol) with water cooling. The suspension was stirred while acetic acid (0.4 mL) was added dropwise. The water bath was removed and the reaction was stirred at room temperature for 1 hour. The crude product was filtered through a pad of florisil (2×2.5 cm) and the florisil washed with 35 mL EtOAc. The brown solution obtained was filtered through another column of florisil (3.5 cm diam×2.5 cm height). The filtrate was concentrated to give 1.273 g (64% yield) of very light brown oil.

(d) 5-(4-Carbethoxy-1,3-butadienyl)-2'-dexoyuridine-3',5'-bis(tetrahydro-2H-pyran-2-yl)ether (IV)

(Carbethoxymethylene)triphenylphosphorane (0.32 mg, 0.92 mmol) was added to a solution of the crude aldehyde (III) (0.344 g, 0.77 mmol). The solution darkened and turned rust color. After 1 hour, (III) was completely consumed as judged by thin layer chromatography. The solvent was evaporated and the crude product was purified by column chromatography on silica gel using 35-45% EtOAc/hexane as eluent. The pure product (0.310 g, 78% yield) was obtained as colorless oil.

(e) 5-(4-Carbethoxy-1,3-butadienyl)-2'-dexoyuridine (V)

5-(4-Carbethoxy-1,3-butadienyl)-2' -dexoyuridine-3',5'-bis(tetrahydro-2H-pyran-2-yl)ether (IV) (0.637 g, 1.22 mmol) was dissolved in MeOH (1.5 mL) and PPTS (0.049 g, 0.16 mmol) was added. The solution was stirred at 50° C. for 7.5 hours and left at room temperature overnight. A white precipitate was formed. The reaction mixture was cooled to 0° C. and filtered to give pure (V) as a white solid (0.188 g). The filtrate was concentrated and chromatographed on silica gel using 50-100% EtOAc/hexane as eluent to give a further 0.180 g product. The total yield of the product was 0.368 g (86%).

$^1$H NMR (DMSO-$d_6$): 1.22 (3H, t, J=7 Hz), 2.17 (2H, br t, J=5.5 Hz), 3.55-3.75 (2H, m), 3.81 (1H, m), 4.12 (2H, q, J=7 Hz), 4.25-4.28 (1H, m), 5.19 (1H, t, J=4.8 Hz), 5.27 (1H, d, J=4.1 Hz), 5.98 (1H, d, J=14.5 Hz), 6.14 (1H, t, J=6.3 Hz), 6.75 (1H, d, J=14.5 Hz), 7.18-7.30 (2H, m), 8.30 (1H, s), 11.56 (1H, s).

EXAMPLE 10

5-(4-Carbomethoxy-1,3-butadienyl)-2'-dexoyuridine (Va)

A solution of triethylamine (3.9 mL, 28.2 mmol) in dioxane (12 mL) was deareated by bubbling nitrogen through for 15 minutes. Palladium acetate (0.60 g, 0.26 mmol) and triphenylphosphine (0.183 g, 0.70 mmol) were added and the solution was heated at 70° C. for 20 minutes to give a dark brown solution. 5-Iodo-3'-deoxyuridine (5.0 g, 14.1 mmol) and methyl 2,4-pentadienoate (2.5 g, 22.3 mmol) were added and the mixture was heated under reflux for 15 hours. The solvent and volatile components were evaporated in vacuo and the residue was partitioned between water (15 mL) and EtOAc (15 mL). The phases were separated and the aqueous phase was extracted twice with EtOAc (10 mL each). The combined organic phase was washed with brine and concentrated. The residue was dissolved in MeOH (15 mL) and allowed to cool to room temperature. The solid formed was collected by filtration, washed with a small quantity of MeOH and dried in vacuo to give 0.38 g brown powder.

$^1$H NMR (DMSO-$d_6$): 2.17 (2H, t, J=6.4 Hz), 3.55-3.70 (2H, m), 3.66 (3H, s), 3.82 (1H, q, J=3.6 Hz), 4.27 (1H, m), 5.18 (1H, t, J=4.9 Hz), 5.26 (1H, d, J=4.5 Hz), 5.99 (1H, d, J=14.4 Hz), 6.14 (1H, d, J=6.4 Hz), 6.74 (1H, d, J=14.8 Hz), 7.20-7.35 (2H, m), 8.30 (1H, s), 11.56 (1H, s).

The filtrate from above was concentrated and chromatographed on silica gel using 60-100% EtOAc/hexanes as eluent to give another 0.70 g of product as a brown foam. The combined yield was 1.08 g (22.6%).

EXAMPLE 11

5-(4-Carboxy-1,3-butadienyl)-2'-dexoyuridine (VI)

Method I 5-(4-Carbethoxy-1,3-butadienyl)-2'-dexoyuridine (V, from Example 9) (0.449 g, 1.28 mmol) was dissolved in 2N NaOH (3 mL) and stirred at 25° C. After 20 minutes, a precipitate was formed and TLC showed that the starting material was completely consumed. The mixture was cooled to 0° C. and acidified to pH 1 with 2N HCl. The resulting off-white solid was filtered off, washed with water and dried in vacuo to give 0.225 g (54%) product.

$^1$H NMR (DMSO-d$_6$): 2.12-2.19 (2H, m), 3.50-3.70 (2H, m), 3.75-3.85 (1H, m), 4.24-4.29 (1H, m), 5.19 (1H, t, J=4.8 Hz), 5.27 (1H, d, J=4.2 Hz), 5.80-5.95 (1H, m), 6.14 (1H, t, J=6.4 Hz), 6.60-6.75 (1H, m), 7.15-7.25 (2H, m), 8.26 (1H, s), 11.56 (1H, s), 12.16 (1H, br s).

The filtrate and washings were combined and evaporated to dryness. The resulting sticky yellow solid was dissolved in MeOH from which a white precipitate was formed. The solid was filtered off to give an additional 0.200 g of product.

Method II

The title compound can also be prepared from 5-(4-carbomethoxy-1,3-butadienyl)-2'-dexoyuridine (Va, from Example 10) in comparable yield as mentioned above.

EXAMPLE 12

5-(4-Bromo-1E,3E-butadienyl)-2'-dexoyuridine (VIIa) and 5-(4-Bromo-1E,3Z-butadienyl)-2'-dexoyuridine (VIIb)

To a solution of 5-(4-carboxy-1,3-butadienyl)-2'-dexoyuridine (VI) (0.200 g, 0.62 mmol) in DMF (1 mL) was added KHCO$_3$ (0.185 g, 1.84 mmol) and the mixture was stirred for 20 minutes at 25° C. A solution of N-bromosuccinimide (0.117 g, 0.65 mmol) in DMF (0.3 mL) was added dropwise. Smooth gas evolution (CO$_2$) occurred throughout the addition. The resulting brown suspension was stirred for 2 hours at 25° C. at which time TLC showed that (VI) was completely consumed. Water (10 mL) was added to the suspension and the resulting solution was extracted with EtOAc (2×15 mL). The extract was dried over MgSO$_4$ and the solvent was evaporated in vacuo to give a yellow solid (178 mg, 80% yield) consisting of a mixture of two isomers as shown by $^1$H NMR. The crude product was separated by semi-preparative HPLC (reversed phase C18 column) using 20% acetonitrile in water as the mobile phase to give the following isomers:

5-(4-Bromo-1E,3Z-butadienyl)-2'-dexoyuridine: retention time 10.5 minutes; $^1$H NMR: (DMSO-d$_6$): 2.11-2.18 (2H, m), 3.50-3.70 (2H, m), 3.80 (1H, distorted q, J=3.5 Hz), 4.25 (1H, br s), 5.08 (1H, br s), 5.25 (1H, br s), 6.15 (1H, t, J=6.5 Hz), 6.40 (1H, d, J=7 Hz), 6.53 (1H, d, J=15.6 Hz), 6.83 (1H, dd, J=7, 10 Hz), 7.39 (1H, dd, J =10, 15.6 Hz).

5-(4-Bromo-1E,3E-butadienyl)-2'-dexoyuridine: retention time 15.1 minutes; $^1$H NMR (DMSO-d$_6$): 2.12-2.16 (2H, m), 3.50-3.70 (2H, m), 3.80 (1H, q, J=3.2 Hz), 4.26 (1H, m), 5.13 (1H, br s), 5.25 (1H, br s), 6.14 (1H, t, J=6.5 Hz), 6.36 (1H, d, J=15.6 Hz), 6.67 (1H, d, J=13.1 Hz), 6.84(1H, dd, J=11, 13.1 Hz), 7.04 (1H, dd, J=11, 15.6 Hz).

EXAMPLE 13

Using the procedures mentioned in Example 11, Method II, the following compounds can be obtained in a similar fashion: 5-(4-chloro-1,3-butadienyl)-2'-dexoyuridine (using N-chlorosuccinimide in place of N-bromosuccinimide in Step B); 5-(4-iodo-1,3-butadienyl)-2'-dexoyuridine (using iodine in sodium idodide in place of N-bromosuccinimide).

EXAMPLE 14

Phenyl N-methoxy-L-alaninyl Phosphorochloridate

L-alanine methyl ester hydrochloride (245.8 g; 1.76 mol) was placed in a 12 liter three-neck round bottom flask (equipped with a mechanical stirrer and thermometer) followed by 4.0 liters of dichloromethane. The mixture was stirred for 15 minutes at room temperature. Phenyl phosphodichloridate (370.0 g; 1.76 mol) was added to the mixture and stirring was continued for 15 minutes at room temperature. The flask was placed in the bath with dry ice and the stirring was continued for 20 minutes until a uniform suspension was formed.

Freshly distilled tri-n-butylamine (626.5 g; 3.38 mol) was added dropwise (~90 minutes) with vigorous stirring to the reaction mixture so that the temperature inside the flask was held at ~0° C. The bath was removed and the stirring was continued for 6 hours at room temperature. The solution was concentrated to ~2.84 liters by evaporating several portions of the mixture on a rotary evaporator and the mixture was sealed under argon and stored at −20° C. The product was 85% pure by phosphorus NMR to give an estimated concentration of phenylmethoxyalaninyl phosphochloridate of ~0.5M.

EXAMPLE 15

5-(2-Bromovinyl)-2'-deoxyuridine phenyl N-methoxy-L-alaninyl phosphoramidate (NB1011)

The reaction was performed under argon atmosphere. 5-(2-bromovinyl)-2'-deoxyuridine (BVdU) (204 g; 612 mmol) was placed in three-neck 3 liter round bottom flask equipped with mechanical stirrer. The flask was placed in ice-water bath and 1600 mL (~800 mmol) of phenylmethoxyalaninyl phosphochloridate reagent were added using an addition funnel over 15 minutes with vigorous stirring of the reaction mixture, followed by the addition of 100 mL of N-methylimidazole over 5 minutes using syringe. After 5 minutes the mixture became clear and after 10 minutes the ice-water bath was removed to allow the mixture to warm up to room temperature while stirring was continued. The reaction was monitored by reversed phase HPLC and was complete in 3 hours. The reaction was quenched by the addition of 100 mL of methanol and the mixture was evaporated to an oil, re-dissolved in 6 liters of dichloromethane and passed through 800 g of silica gel. The major portion of BVdU-PA, referred to herein as NB1011, was passed through the column during the loading and finally the elution of NB1011 was completed by passing 5 liters of 5% methanol in dichloromethane. All fractions containing NB1011 were combined and evaporated to an oil, the residue was dissolved in 4 liters of ethyl acetate and the mixture was extracted with water (2×2 liters). The organic layer was dried with sodium sulfate, filtered, and washed with ethyl acetate (3×300 mL). The combined filtrate and washings were evaporated to produce a lightly colored white foam; total weight ~540 g.

The crude product was purified by two silica gel chromatography using 0-5% MeOH in CH$_2$Cl$_2$ and 10% MeOH in CH$_2$Cl$_2$, respectively, as eluent. The yield of product (>98% pure) was 64 g.

EXAMPLE 16

Using the methods described in Example 15, the phenyl N-methoxy-L-alanyl phosphoramidates of the following nucleosides were prepared:

5-(4,4-dibromo-1,3-butadienyl)-2'-deoxyuridine;
5-(2-chlorovinyl)-2'-deoxyuridine;
5-trifluoromethyl-2'-deoxyuridine;
5-(4-carbethoxy-1,3-butadienyl)-2'-deoxyuridine;
5-(4-carbomethoxy-1,3-butadienyl)-2'-dexoyuridine;
5-(4-bromo-1E,3E-butadienyl)-2'-deoxyuridine;
5-(4-bromo-1E,3Z-butadienyl)-2'-deoxyuridine;
5-(trimethylsilylethynyl)-2'-deoxyuridine;
5-(ethynyl)-2'-deoxyuridine;
5-(1-decynyl)-2'-deoxyuridine;
3-(2'-deoxy-β-D-ribofuranosyl)-2,3-dihydrofuro[2,3-d]pyrimidin-2-one; and
3-(2'-deoxy-β-D-ribofuranosyl)-6-octyl-2,3-dihydrofuro[2,3-d]pyrimidin-2-one.

EXAMPLE 17

Using the methods described in Examples 14 and 15, the following amino acid phosphoramidate derivatives of 5-(2-bromovinyl)-2'-deoxyuridine were prepared:
Phenyl (benzoxy-L-alaninyl) phosphoramidate;
Phenyl (methylene cyclopropoxy-L-alaninyl) phosphoramidate;
Phenyl (cyclohexoxy-L-alaninyl) phosphoramidate;
Phenyl (iso-propoxy-L-alaninyl) phosphoramidate;
Phenyl (methylene tert-butoxy-L-alaninyl) phosphoramidate;
Phenyl (cycloheptoxy-L-alaninyl) phosphoramidate;
Phenyl (cyclooctoxy-L-alaninyl) phosphoramidate;
Phenyl (methylene adamantoxy-L-alaninyl) phosphoramidate; and
Phenyl (methoxy-L-tryptophanyl) phosphoramidate.

Chemical assays for products, for example, where a reaction product is an anti-metabolite of the bromovinyl-derivatives of dUMP, are described in the Examples provided below or by Barr, P. J. et al. (1983).

EXAMPLE 18

Cell and Enzyme Based Assays

Expression of thymidylate synthase in human normal tissues. The TS expression level in normal human tissues was examined in order to estimate the systemic toxicity of the compound(s) activated by thymidylate synthase. The relative TS mRNA levels in brain, heart, kidney, spleen, liver, colon lung, small intestine, stomach muscle, testis, ovary, uterus, prostate, thyroid gland, salivary gland, adrenal gland, skin, PBL and bone marrow tissues were determined by using RT-PCR. It has been shown that TS mRNA levels in most of these tissues were equal to or less than that in colon tissue, except that in bone marrow (1.25 fold), ovary (1.38 fold) and testis tissues (2.13 fold). However, the average TS mRNA level in colon cancer samples was 4.6 fold more than that in their matched normal colon tissue samples. This result suggests that compounds which are activated by overexpressed TS in colon cancer would have no or little toxicity to normal human tissues.

Transcript levels of human thymidylate synthase in multiple normal tissues were investigated by PCR amplification. Panel of cDNAs of human tissues were obtained from Ori-Gene Technologics, Inc. (Rockville, Md.). PCR reactions were perfromed in a volume of 25 μl, containing cDNA (100×), 3 mM $MgCl_2$, 50 mM KCl 20 mM Tris-Cl, pH 8.4, 0.2 mM of each dNTP, 0.2 μM of thymidylate synthase sense and antisense primers and 1.25 units of Taq DNA polymerase (obtained from Promega, Madison, Wis.). The reaction mixtures were incubated at 94° C. for 2 min, followed by 12 cycles of 40 sec incubations at 94° C., 1 min incubation at 58° C., and then 1 min incubation at 72° C.25 μl reaction buffer contained 0.2 μM β-actin primers, 0.2 μM of thymidylate synthase primers, 3 mM $MgCl_2$, 50 mM KCl, 20 mM Tris-cl, pH 8.4, 0.2 mM of each dNTP and 1.25 units of Taq DNA polymerase were added to achieve a final concentration of 0.2 μM of thymidylate synthase primers and 0.1 μM β-actin primers, bringing the reaction volume to 50 μl. PCR reaction was continued to a total of 36 cycles, followed by a 7 min incubation at 72° C.

10 μL of PCR products were resolved by electrophoresis in a 2% agarose gel, followed by staining with SYBR Gold nucleic acid gel stain (obtained from Molecular probes, Eugene, Oreg.). The DNA bands corresponding to thymidylate synthase were quantified and normalized to that of β-actin by Molecular Dynamics Storm. The quantified expression levels were expressed as values relative to that of colon.

RT-PCR analysis of matched normal and tumor tissues. Transcript levels of human thymidylate synthase in colon cancer tissues and matched normal colon tissues were quantified by using Reverse RT-PCR amplification. Oligonucleotide primers for amplification of the human thymidylate synthase and β-actin were designed as following: thymidylate synthase sense primer 5'-GGGCAGATCCAACA-CATCC-3' (SEQ ID NO. 1) (corresponding to bases 208-226 of thymidylate synthase cDNA sequence, Genbank Accession No. X02308), antisense primer 5'-GGTCAACTCCCT-GTCCTGAA-3' (SEQ ID NO. 2) (corresponding to bases 564-583), β-actin sense primer 5'-GCCAACACAGTGCT-GTCTG-3' (SEQ ID NO. 3) (corresponding to bases 2643-2661 of β-actin gene sequence, Genbank Accession No. M10277) and antisense primer 5'-CTCCTGCTTGCTGATC-CAC-3' (SEQ ID NO. 4) (corresponding to bases 2937-2955).

Human colon tumor tissues and matched normal tissues were obtained from Cooperative Human Tissue Network (CHTN, Western Division, Cleveland, Ohio). Total RNAs were isolated using Tri pure isolation reagent (obtained from Boehringer Mannheim Corp., Indianapolis, Ind.), followed manufactureis protocol. To monitor for possible DNA contamination, the primers for amplification of β-actin were designed to span the exon4/intron5/exon5 junction. Genomic DNA template leads to a 313 bp β-actin fragment, and cDNA template generates a 210 bp product.

Reverse transcriptions were performed, using SuperScript preamplification system (Gibco/BRL, Gaithersburg, Md.). 3 μg total RNA was applied in a volume of 20 μl buffer to conduct reverse transcription reaction, followed manufacture's protocol.

PCR reactions were performed in a volume of 96 μl, containing 5 μl of cDNA mixture from reverse transcription reaction, 3 mM $MgCl_2$, 50 mM KCl, 20 mM Tris-Cl, pH 8.4, 0.2 mM of each dNTP, 0.3 μM of thymidylate synthase sense and antisense primers and 5 units of Taq DNA polymerase (obtained from Promega, Madison, Wis.). The reaction mixtures were incubated at 94° C. for 3 min, followed by 9 cycles of 1 min incubation at 94° C., 1 min incubation at 58° C., and then 1 min incubation at 72° C. After 9 cycles, human β-actin primers in 4 μl were added to achieve a final concentration of 0.2 μM, bringing the final reaction volume to 100 μl. PCR reaction was continued to a total of 30, 32 or 34 cycles, followed by a 7 min incubation at 72° C.

10 μL of PCR products were resolved by electrophoresis in 2% agarose gel, followed by staining with SYBR Gold nucleic acid gel stain (obtained from Molecular probes, Eugene, Oreg.). Result of quantification indicated that amplification of thymidylate synthase and β-actin was linear between cycles 30 and 34. The DNA bands corresponding to thymidylate synthase were quantified and normalized to that of actin by Molecular Dynamics Storm. The quantified expression levels were expressed as values of ratio between TS and β-actin.

Cell lines and transfection. HT1080 cells were grown in PRM11640 medium supplemented with 10% fetal calf serum, and transfected with GFP-TS expression vector. 48 hours after, transfection cells were tripsinized and replated in culture medium containing 750 μg/ml G418. After selection with G418 for two weeks, surviving cells were sorted based upon fluorescence expression. One clone with higher fluorescence expression (named as TSH/HT1080) and one clone with lower fluorescence expression (named as TSL/HT1080) were selected and expanded into cells lines. The stable HT1080 cells transfected with pEGFP-C3 were used as control.

Construction of GFP-TS expression vector. A cDNA fragment encoding conserved region of human thymidylate synthase (amino acids 23 to 313) was obtained by PCR amplification using following primers: Sense primer, 5'-CGGAAGCTTGAGCCGCGTCCGCCGCA-3' (SEQ ID NO. 5) and antisense primer, 5'-GAAGGTACCCTAAA-CAGCCATTTCCA-3' (SEQ ID NO. 6). The cDNA was cloned into HindIII and KpnI sites of mammalian expression vector pEGFP-C3 (Clontech Laboratories. Inc., Palo Alto, Calif.), in-frame with GFP sequence. The cDNA insert was confirmed by DNA sequencing.

Western blot analysis. Human normal and cancer cells were grown in RPMI 1640 medium supplemented with 10% fetal bovine serum. Cells were grown till confluent in 100 mm culture dish and lysed in 0.5 ml of RIPA buffer (50 mM Tris-HCl, pH 7.5, 150 mM NaCl, 0.5% Triton X-100, 0.1% SDS, 0.5% Deoxycholic acid, sodium salt and protease inhibitors ). Protein concentrations were determined by using BCA-200 protein assay kit (obtained from Pierce, Rockford, Ill.). 15 μg of total protein from each cell strain/line was resolved by 12% SDS-PAGE. The separated proteins were transferred onto PVDF membrane, followed by immunoblot with human thymidylate synthase monoclonal primary antibody (manufactured by NeoMarkers, Fremont, Calif.) and horseradish peroxidase linked sheep anti-mouse Ig secondary antibody (obtained from Amersham, England). The ECL plus kit (Amersham) was used for detection of immunoreactivity. The bands corresponding to thymidylate synthase were quantified and normalized to that of tubulin by Molecular Dynamics Storm. The quantified expression levels were expressed as values relative to that of cell strain CCD 18co.

TS Activity Assay by Tritium Release from dUMP-$^3$H. Cells were plated in 24 well plates to a density of 30,000 cells/plate and incubated for 16 hours to allow adhesion to the plastic surface of the plate.

Immediately prior to the thymidylate synthase assay, the media was replaced with RPMI+10% dialyzed fetal calf serum. 0.5 μCi of 5-[$^3$H]deoxyuridine was added to each well, and plates were incubated for 60 minutes at 37° C. without additional $CO_2$. [$^3$H] release was measured by adsorbing 5-[$^3$H]deoxyuridine to activated charcoal (10% in 1×PBS) for 5 minutes at room temperature. After centrifugation for 5 minutes at 13,000 RPM, the amount of [$^3$H] in the supernatant was determined by liquid scintillation counting.

Growth Inhibition Studies. Cells growing exponentially were transferred to 384-well flat bottom tissue culture plates. All cell types were plated at a density of 500 cells per well in 25 μL of complete medium (RPMI 1640+10% fetal bovine serum+antibiotics/antimycotics). After 24 hours (day 0), 25 μL of complete medium containing the experimental compounds over the dose range of $10^{-3}$ to $10^{-10}$ M were added in triplicate. Drug exposure time was 120 hours (day 5), after which growth inhibition was assayed. 5 μL of the redox indicator, alamarBlue, was added to each well (10% v/v). After 4 hours incubation at 37° C., fluorescence was monitored at 535 nm excitation and 595 nm emission.

Concentration vs. relative fluorescence units (RFU) were plotted, and sigmoid curves were fit using the Hill equation. $IC_{50}$, indicated by the inflection point of the curve, is the concentration at which growth is inhibited by 50%.

Enzyme Preparation. Cloned human thymidylate synthase plasmid pBCHTS was subcloned into E. coli. BL21 (DE3)/pET-28a(+) (Novagen) using the NdeI ñSacI insertion site, in order to add an amino terminal His tag. Enzyme was expressed in E. coli. by induction with IPTG, and purified by affinity chromatography on a $Ni^{2+}$ His Bind metal chelation resin (Novagen). The column $Ni^{2+}$ His Bind metal chelation column was washed with 20 mM Tris pH 7.9, 5 mM imidazole, 0.5M NaCl; thymidylate synthase activity was eluted with 20 mM Tris pH 7.9, 60 mM imidazole, 0.5M NaCl.

Enzyme Assays and Kinetic Measurements. Thymidylate synthase assays were done in 96 well Costar UV transparent plates in a reaction volume of 200 μL, consisting of 40 mM Tris pH 7.5, 25 mM $MgCl_2$, 1 mM EDTA, 25 mM-mercaptoethanol, 125M dUMP, and 65 μM N5, N10-methylene tetrahydrofolate indicated. Tetrahydrofolate stock solutions were prepared by dissolving tetrahydrofolic acid (Sigma) directly into 0.2M Tris pH 7.5, 0.5 M-mercaptoethanol; stock solutions were stored at −80° C. N5, N10-methylene tetrahydrofolate was prepared by adding 12 μl of 3.8% formaldehyde to 1 ml of a 0.65 mM solution of tetrahydrofolate and incubating for 5 minutes at 37° C. N5, N10-methylene tetrahydrofolate was kept on ice and used within 2 hours of preparation.

Conversion of BVdUMP to fluorescent product(s) by thymidylate synthase was measured in 200 μl thymidylate synthase reactions containing 125M BVdUMP in 96 well Dynex Microfluor Black "U" bottom microtiter plates using an excitation wavelength of 340 nm and emission wavelength of 595 nm. Fluorescence was measured with a Tecan Spectrafluor Plus fluorimeter.

Enzyme kinetic constants ($K_m$ and $V_{max}$) were determined for the human thymidylate synthase substrates dUMP and BVdUMP using the enzyme assay conditions described above. Results are shown in Table 3. The initial rates of the enzyme reactions was determined by measuring the increase in $A_{340}$ for the reaction with dUMP, and decrease in $A_{294}$ for the reaction with BVdUMP. The catalytic efficiency of the enzyme ($K_{cat}/K_m$) was calculated from the kinetic constants $K_m$ and $V_{max}$.

Liquid Chromatography/Mass Spectroscopy. Cells were washed three times with PBS at room temperature, then subjected to freeze/thaw lysis in 5 ml PBS. Cell extracts were centrifuged for 10 minutes at 10KRPM, then adsorbed to Sep-Pak $C_{18}$ and washed with 10 ml PBS. BVdUMP was eluted with 1 ml distilled water. LC/MS samples were analyzed by reverse phase chromatography on a $C_{18}$ column using a linear gradient of 0.1% formic acid-0.1% formic acid/95% acetonitrile. Mass spectroscopy was done with a Micromass Quattro II triple quadropole spectrometer.

Tomudex Inhibition of NB1011 Cytotoxicity. MCF7-TDX were transferred to a 384 well assay plate at 500 cells in 25 μL complete medium per well. After 24 hours (day 0), 25 μL complete medium containing a combination of NB1011 in doubling serial dilutions from 1 mM and tomudex at discrete concentrations (0,1,10,100,1000 nM) were added in duplicate. Drug exposure time was 120 hours (day 5) after which growth inhibition was measured with alamarBlue as described above in Growth Inhibition Studies (above).

Reversal of Resistance. The origin and characteristics of the human breast cancer MCF7 TDX cell line have been previously described (Drake, et al. (1996)). Briefly, MCF-7 breast cancer cells were selected in vitro for resistance to Tomudex by continuous exposure to stepwise increases in TDX concentrations up to 2.0 µM. A resistant subline was selected for resistance to NB1011 by continuous exposure of the parental MCF7 TDX cell line to medium supplemented without TDX but with 50 µM NB1011, a concentration approximately 16 times higher than the $IC_{50}$ for NB1011 in the parental MCF7 TDX cell line. After a dramatic initial cell killing effect, resistant colonies emerged, and vigorously growing monolayers were formed. TS protein level and $IC_{50}$ for 5-FU, TDX, and NB1011 were determined for the resultant MCF7 TDX/1011 cell line as described in above by western blot and the alamarBlue cytotoxicity assay, respectively.

Analysis of NB1011 in TS-expressing, 5-FU resistant, H630-10 colon carcinoma xenografts in vivo. H630-10 colon cancer cells, selected for resistance to 5-FU in vitro, express high levels of thymidylate synthase, and form xenografts in athymic mice. Following cell expansion ex-vivo H630-10 were injected subcutaneously (S.Q.) at $1.5 \times 10^7$ cells/tumor in the mid-back region of 4-6 week old, female, CD-1 (nu/nu), athymic mice (Charles River Laboratories, Wilmington, Mass.). Tumor volumes, calculated as the product of length, width, and depth, were monitored twice weekly by serial micrometer measurements by a single observer. Six animals were randomly assigned to each treatment group and statistical tests were performed (single-factor ANOVA) to assure uniformity in starting tumor volumes between treatment and control groups at the beginning of the experiment. NB1011 was administered by intraperitoneal (I.P.) or intratumoral (IT) injection. The dosage of experimental agents tested were as follows: Group 1: DMSO vehicle control solution (IP), Group 2: 5-FU (15 mg/kg×5 days IP=the MTD for 5-FU in this model), Group 3: NB1011=1.25 mg×5 days (IP), Group 4: NB1011=2.5 mg×5 days (IP), Group 5: NB1011=3.5 mg×5 days (IP), Group 6: DMSO control (IT), Group 7: NB1011=1.25 mg×5 days (IT), and Group 8: NB1011=2.5 mg×5 days (IT). These doses were based on independent dose-finding experiments conducted in our laboratory and were near the maximum-tolerated dose of NB1011 for this specific age and strain of female athymic mice. To assure accurate dosing, drug doses were individualized based upon animal weights determined immediately prior to each injection. Treatment with control solution or NB1011 was initiated 10 days status post xenograft inoculation at which time xenograft volumes measured 45-68 mm$^3$. Differences in day 25 xenograft volumes between groups were analyzed by single-factor ANOVA of the log transformed tumor volume data. Experimental athymic mice were maintained under aseptic conditions in a dedicated room in the UCLA Animal Care Facility. The University of California, Los Angeles has an Animal Welfare Assurance document on file with the Office of Protection from Research Risks, Laboratory Animal Safety Assurance Number A-3196-01. All experiments were closely supervised by the UCLA veterinarian. Euthanasia techniques employed by UCLA are supported by the Panel of the American Veterinary Medical Association. The University of California, Los Angeles experimental animal program and facilities are accredited by the American Association for the Accreditation of Laboratory Animal Care. The personnel performing the animal procedures/manipulations described in this protocol are technically competent in those procedures and have received their training on the use of animals in research, as required by the Animal Welfare Act of 1985.

In vitro Reaction of BVdUMP with Human Thymidylate Synthase

1. The Cell-free Processing of BVdUMP by rHuTS Generates Fluorescent Product(s).

The cell-free processing of BVdUMP by *L. casei* TS has been shown to create potentially reactive intermediates (Barr, et al. (1983)). For this reason it has been thought that processing of BVdUMP by TS leads to irreversible inactivation of human TS (Balzarini (1987)). The cell-based experiments by DeClercq, Balzarini and colleagues (Balzarini (1987); Balzarini (1993); and Balzarini (1995)) support the concept that, once BVDU is converted to the monophosphate in cells (via herpes virus thymidine kinase), then it binds to and inactivates the Hu TS enzyme during processing. However, the actual reaction of human TS with BVdUMP has never been adequately characterized. Santi and colleagues (Barr, P. J. et al. (1983)) utilized a bacterial TS for their work to show generation of product from the BVdUMP+TS reaction, and DeClercq and colleagues utilized cells and cell lysates, not purified human TS (Balzarini (1987)); Balzarini, (1993); and Balzarini (1995)).

The interaction of BVdUMP with purified recombinant human TS (rHuTS) was revisited. When BVdUMP was incubated with rHuTS in the standard reaction mixture, the reaction results in the formation of fluorescent product(s) (FIG. 1). The time dependent increase in fluorescence is accompanied by a decrease in the initial BVdUMP concentration. The product(s) produced have been partially characterized, and appear to be exocyclic pyrimidine nucleotide derivatives.

This result is surprising because previous results supported the idea that TS reaction with BVdUMP should inactivate the human TS enzyme (Balzarini, et al. (1987), (1993), and (1995)). Because the reactions described above were done in a cell-free system with purified components, it remained possible that the intracellular milieu could provide components that would result in TS inactivation following conversion of NB1011 to the free nucleotide monophosphate inside the cell. This issue is addressed in more detail below.

2. Comparative Reaction Kinetics of dUMP and BVdUMP with rHuTS.

Previously reported work by Barr, et al.(1983), utilizing the *L. casei* TS (Balzarini (1987), (1993), and (1995)) using cells and cell lysates, leaves unclear whether the reaction of BVdUMP with human TS will result in irreversible inactivation of the enzyme. To address this question, the kinetics of interaction of BVdUMP with rHuTS, in the presence or absence of dUMP, were determined.

Figure 2:
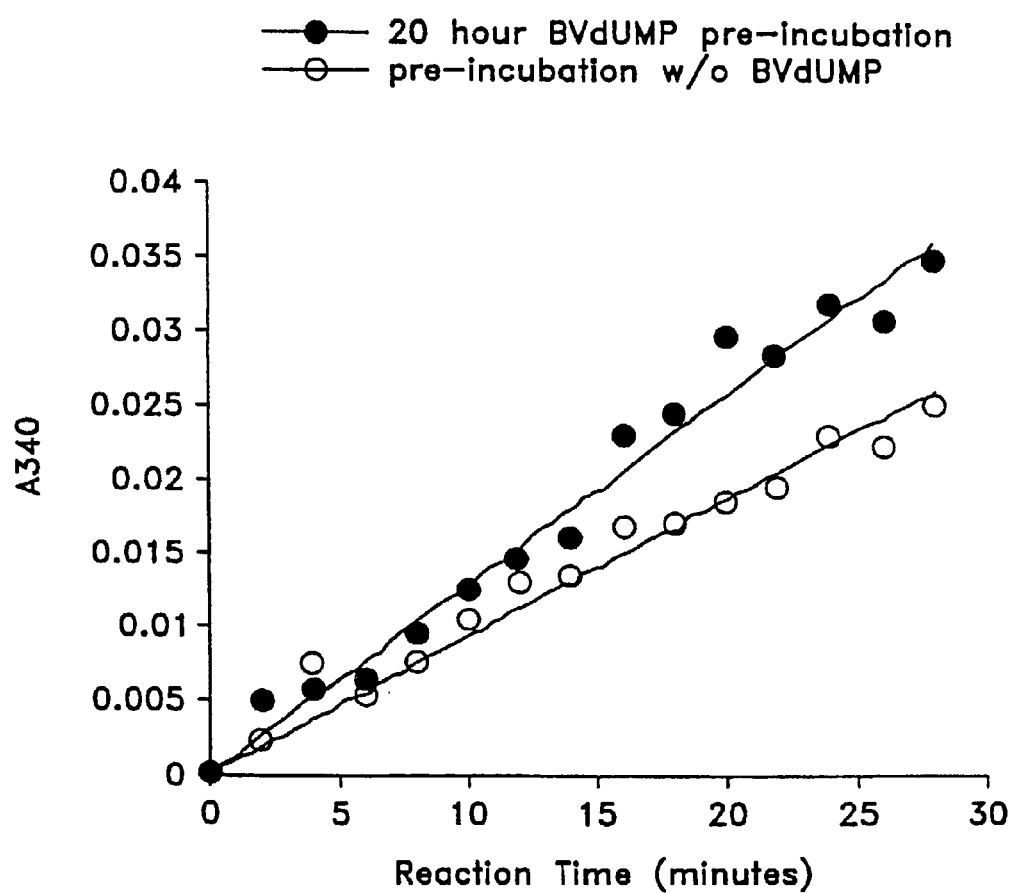
FIG. 2 shows the results of an experiment that demonstrates that preincubation with BVdUMP does not inactivate rHuTS. Human thymidylate synthase was pre-incubated in reaction mixtures with and without 125 µM BVdUMP. After 20 hours, BVdUMP was added to a concentration of 125 µM, dUMP to a final concentration of 125 µM, and N5, N10-methylene tetrahydrofolate was added to 70 µM. Thymidylate synthase activity was determined by measuring the increase in $A_{340}$. Solid circles (preincubated reaction), Open circles (no preincubation).

Competitive inhibition is most consistent with a reaction in which BVdUMP does not inactivate the TS enzyme. To help further clarify this situation, an extended incubation of rHuTS with BVdUMP was done in order to measure any inactivation that may occur over a period of time longer than that in which the kinetics were performed (FIG. 2).

These data show that even after a 20 hour incubation of rHuTS with BVdUMP, little or no enzymatic inactivation is apparent as measured by rate of conversion of THF DHP dUMP as substrate. This result is consistent with the hope for ability of overexpressed TS to convert BVdUMP into cytotoxic metabolites in cells, preferentially in cells which overexpress TS, and finally, without inactivating the enzyme.

3. Characterization of BVdUMP reaction with TS: Cofactors and Inhibitors

The best characterized reaction of TS is the conversion of dUMP to dTMP. This reaction involves the transfer of a methylene group from N5,N10-methylene tetrahydrofolate (THF) to the C-5 position of dUMP (Carreras, C. W. and Santi, D. V. (1995)). This reaction is dependent upon the cofactor (THF), and is inhibited by the uridylate mimic, 5F-dUMP, which, upon reaction with the enzyme, results in the formation of a stable complex and loss of enzymatic activity. A second well characterized inhibitor of TS activity is Tomudex, which occupies the folate binding site of the TS homodimer, prevents the binding of THF, and blocks TS activity in the cell (Drake (1996) and Touroutoglou and Pazdur (1996)). As part of a preliminary effort to characterize the reaction of rHuTS with BVdUMP, the effects of 5F-dUMP, Tomudex and cofactor were compared on the reaction of the enzyme with dUMP and BVdUMP. These experiments (Table 3) show that, similarly to the case of dUMP, 5F-dUMP can prevent conversion of BVdUMP to fluorescent product(s). In addition, Tomudex can also prevent product formation from both dUMP and BVdUMP. However, consistent with earlier reported results with *L. casei* TS (Barr, et al. (1983)), THF is not required for the conversion of BVdUMP to fluorescent product(s). In addition, the data shown in Table 3 also demonstrate that THF stimulates the production of fluorescent product(s) in the BVdUMP reaction with rHuTS. This result is not expected from the earlier data reporting that THF has no effect on this reaction (Barr, P. J. et al. (1983)), and illustrates a potentially important possibility that cofactors, or cofactor agonists, like leucovorin, could modulate the reaction of BVdUMP with human TS.

Analysis of the Michaelis-Menton kinetics of this reaction showed that inhibition of BVdUMP by dUMP fits the expected form for competitive inhibition, consistent with both nucleotides behaving as substrates for rHuTS.

Previously reported data with the *L. casei* TS indicated that BVdUMP is 385 times less efficient a substrate as dUMP (Barr, P. J. et al. (1983); Santi, D. V. (1980)). The experiments reported herein have shown that this situation is quite different with the human enzyme. For rHuTS the relative catalytic efficiency of dUMP compared with BVdUMP is 60×. This represents a >6.4 fold increase in catalytic efficiency as compared to endogenous substrate. The previous result with *L. casei* TS leads to the prediction that the efficiency of enzymatic reaction within the cell would be too low for NB1011 to be an effective therapeutic substrate, since it would have to compete with large amounts of endogenous dUMP. The discovery reported herein, ie. that the human enzyme has a >6.4-fold improved efficiency of conversion of BVdUMP, is an important factor enabling utility of NB1011. The increased efficiency of BVdUMP utilization by the human enzyme as compared to the *L. casei* enzyme also establishes that species specific substrates are possible and can be designed. The ability to specifically inhibit heterologous enzymes via binding to species specific regions on the surface of *L. casei* vs. human TS has recently been reported (Stout (1999) and Costi, et al. (1999)). Differences in specificity relating to the active site of TS, which is composed of the most highly conserved regions of the protein (Carreras, C. W. and Santi, D. V. (1995)) is surprising and has not been reported previously.

Products of the cell-free enzymatic reaction of rHuTS with BVdUMP were analyzed by mass spectroscopy. The two molecular structures of the products have masses that are consistent with the mass of molecular ions detected in TS reaction mixtures following incubation of BVdUMP with purified rHuTS. Knowledge of the products of this reaction may be used to understand the final mechanism of action of NB1011. In addition, this information could be used to design novel chemotherapeutics, since the products of the TS-BVdUMP reaction could, themselves, be potentially used as chemotherapeutics.

4. NB1011 is Converted to the Monophosphate in Tumor Cells.

Figure 3A:
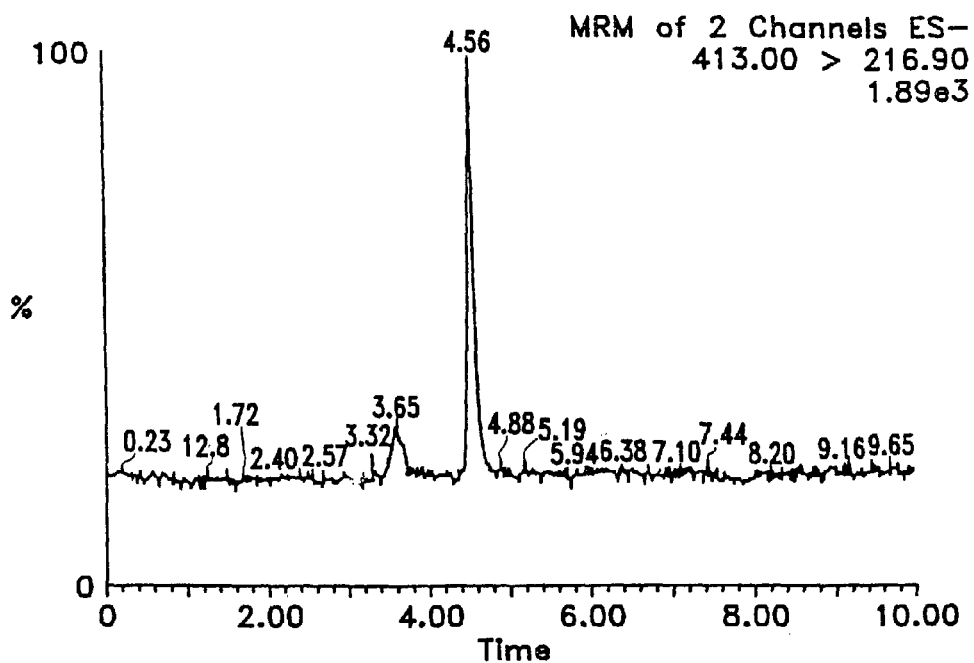
FIGS. 3A and 3B show detection of BVdUMP in H630R10 cells treated with NB1011. H630 R10 cells were treated with 100 µM NB1011 for 5 days, then analyzed by LC/MS as described in Materials and Methods.
Figure 3B:
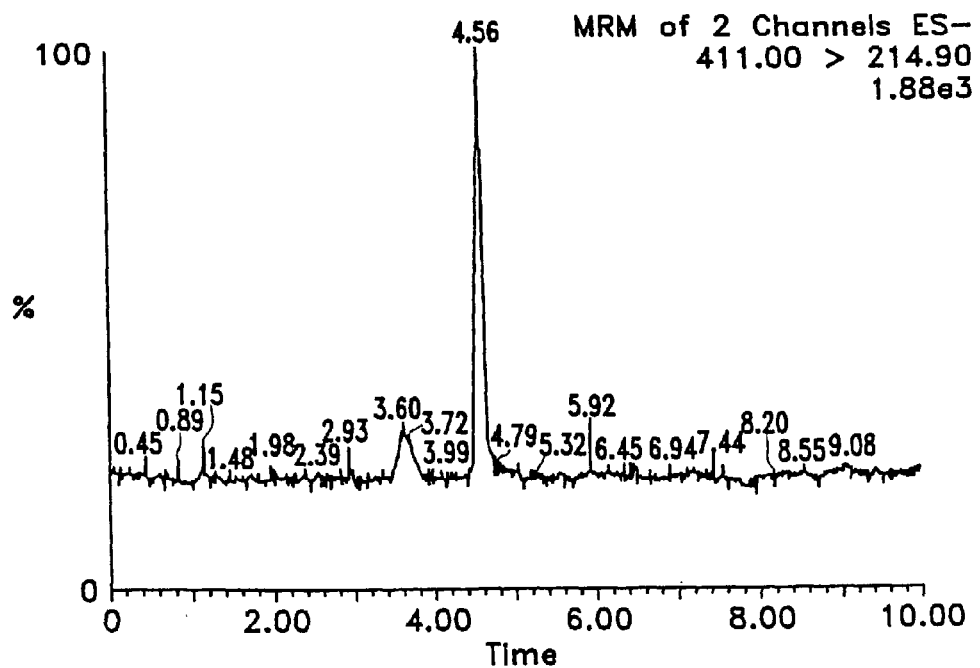

NB1011 is converted from the phosphoramidate to the monophosphate form in cells, as a prerequisite for binding to TS. To determine whether this crucial step in conversion was taking place advantage was taken of an unusual property of the bromine atom, i.e. that it exists in nature in two equally abundant isotopic forms. This situation allows detection of the bromine containing monophosphate by focusing the mass spectrometry analysis on the predicted mass ions of BVdUMP (411 and 413 daltons). H630 R10 tumor cells (which express high levels of TS) were incubated with 100 FM NB1011. Extracts of treated cell lysates were prepared as described herein. Detection using mass spectroscopy, following an initial purification with liquid chromatography relied upon formation of the unprotected nucleotide mass ions of BVdUMP which have identical retention times on reverse phase chromatography. Results are shown in FIGS. 3A and 3B.

Characterization of the Cytotoxic Activity of NB1011

1. The Tumor/normal Cell Screen.

As an initial step in characterizing the biological activity of NB1011, a large series of normal and tumor cell types were tested in the alamarBlue assay for sensitivity to both NB1011 and 5-fluorouracil.

Assays were carried out as described in Methods, above. Therapeutic index is calculated as the ratio of the average $IC_{50}$ for normal cells to the average $IC_{50}$ for tumor cells. All assays were done at least three times. See Table 5.

These data show that NB1011 has met the primary design goal for TS ECTA compounds, i.e. increased potency on tumor cells vs. normal cell types. Overall, NB1011 is about 2-fold more cytotoxic to tumor cells vs. normal cells, while 5-FU is 3-fold more toxic to normal cells than it is to tumor cells. The total benefit of NB1011 is therefore (2)×(3)=6-fold improvement in therapeutic index for NB1011 as compared with 5-FU. A critical tactic that allows for selection of chemotheraputics with a positive therapeutic index is screening of activity on both normal and tumor cell types. This approach has not been consistently employed in the field of new cancer drug discovery. For instance, screening of new candidate compounds on normal cell types is part of the National Cancer Institute's screening procedure (Curt (1996)).

2. NB1011 Does Not Inactivate TS in vivo.

Figure 4:
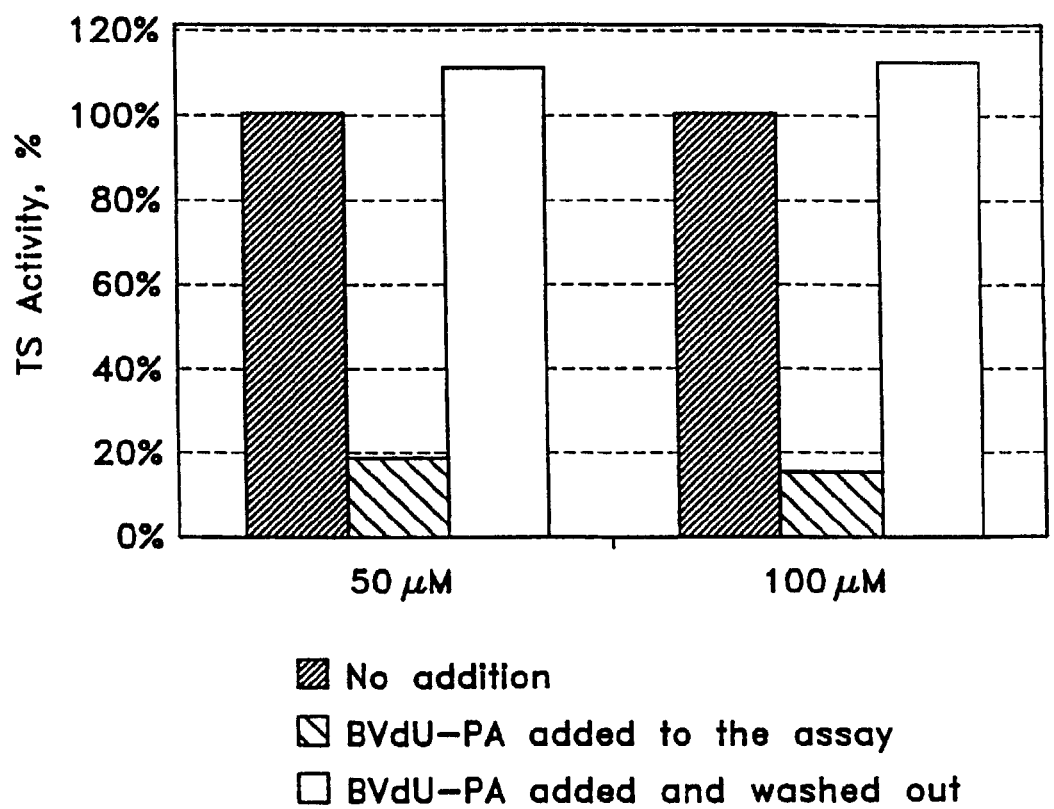
FIG. 4 demonstrates that NB1011 does not irreversibly inactivate TS in vivo. The effect of NB1011 on TS activity in intact cells is completely reversible. TS activity was measured in intact RKO cells by release of $[^3H]_2O$ from 5-$[^3H]$ deoxyuridine as described in Materials and Methods. NB1011 was washed out of cells by replacing with fresh media, incubating for 60 minutes at 37° C., then repeating this procedure. Control and untreated cells were subjected to the same washing procedure.

The results described above indicate that BVdUMP, generated intracellularly from NB1011, is unlikely to inactivate TS during its transformation to product(s). However, the cell free system is different from the intracellular milieu. In order to further explore this question, cell-based assays for TS activity were performed. In these experiments exogenous 5-(3H) deoxyuridine is added to cell culture medium and the release of tritiated water is monitored (Carreras, C. W. and Santi, D. V. (1995) and Roberts (1966)). FIG. 4 shows that the presence of NB1011 in cell culture media reduces the rate at which $[^3H]_2O$ is released from 5-$[^3H]$dUMP. In order to determine whether this is the result of irreversible inhibition of TS, NB1011-treated cells were allowed to briefly recover in fresh culture media, then assayed for TS activity. Cells that have been allowed to recover in culture media lacking NB1011 have the same level of TS activity as untreated cells.

This result supports the proposal that NB1011 does not irreversibly inactivate the TS enzyme following intracellular processing.

An additional approach was taken to understanding whether NB1011 might interfere with cell growth primarily by inactivating TS. This approach is based upon thymidine rescue of TS-blocked cells. Cells which are blocked by Tomudex or by 5FdUMP (following treatment by 5FdUrd) do not make dTMP by de novo synthesis. For this reason, they survive only by scavenger mechanisms. One of the important scavenger mechanisms is utilization of extracellular thymidine. Thymidine incorporated by target cells can be converted to dTMP, usually by thymidine kinase, and thus continue DNA synthesis. Other pathways for use of exogenous thymidine have also been described If an important mechanism for NB1011 activity is via inhibition of endogenous TS, then the cytotoxicity should be relieved when thymidine is added to the cell culture media. For this experiment, a number of tumor cell lines were screened for their sensitivity to Tomudex and 5FdUrd, and ability to be rescued from these agents via thymidine supplementation. The normal colon epthelial cell, CCD18co, was used because of its measurable sensitivity to NB1011, 5FUdR and Tomudex. Experiments were carried out as described by (Patterson, et al. (1998)) with or without 10 µM thymidine, except that the alamarBlue assay was employed to determine cytotoxicity. The results showed a 15-fold rescue from Tomudex ($IC_{50}$ change from 6.5 nM to 95 nM), a greater than 590-fold rescue from 5FudR (from an $IC_{50}$ of less than 0.01 µM to greater than 5.9 µM), and a slight decrease in the absence of thymidine to 223 µM in the presence of 10 µM thymidine.

3. Relationship Between TS Level and NB1011-mediated Cytotoxicity on Tumor Cell Lines.

Confirmation that TS participates in NB1011-mediated cytotoxicity was established using several approaches: 1). The activity of NB1011 was examined on normal colon cells vs. high TS expressing, 5FU-resistant, tumor cells; 2). transfection of TS into a tumor cell background, and generating clonal derivatives which differ primarily by TS expression level, but are otherwise very similar; and 3). Use of a specific inhibitor of TS, Tomudex, to decrease intracellular TS activity.

In the initial analysis, of NB1011 and 5FUdR-mediated cytotoxicity were compared on the CCD18co normal colon epithelial cell type and H630R[10], 5FU-resistant colon tumor cell line (Copur, S. et al. (1995)). This allows a determination of cytotoxicity vs. normal cells (CCD18co) as well as a measure of cytotoxicity vs. drug-resistant tumor cells (H630R10), which overexpress TS. This is important because a significant limitation to current chemotherapeutics is their toxicity to normal tissues. The results are presented in Table 5.

This experiment shows that 5FUdR is about 18-fold more toxic to normal colon cells (CCD18co) than to 5FU-resistant H630R10 tumor cells. This negative therapeutic index characterizes the major limitation of current chemotherapy, i.e. its toxicity to normal tissue. Such a negative therapeutic index has also been reported for doxorubicin (Smith, et al. (1985) and Smith, et al. (1990)). In contrast to 5FUdR, however, NB1011 has more than an 11-fold improved activity on drug-resistant H630R10 cells ($IC_{50}$=216.7 µM) vs. normal colon epithelial cells ($IC_{50}$ greater than 2500 µM). This result suggests that: 1). Activity of NB1011 is more pronounced on high TS expressing tumor cells; and 2). A total improvement in therapeutic index of (18)×(11)=198-fold is achievable using TS ECTA compounds vs. 5FUdR.

4. Overexpression of TS in HT1080 Tumor Cells Enhances Their Sensitivity to NB1011.

Activation of NB1011 requires several steps. These include cell penetration conversion to the nucleotide monophosphate, binding to TS, and subsequent toxic metabolism. The precise mechanisms of cell penetration and conversion are not fully defined. Cell entry may depend in part on nucleoside transport mechanisms (Cass, et al. (1998)). Similarly, processing from the phosphoramidate to the monophosphate employs poorly defined mechanisms (Abraham, et al. (1996)).

These results are particularly significant because they demonstrate, in a fairly uniform genetic background, that increasing TS levels predicts enhanced sensitivity to NB1011. In addition, the data also show that increasing TS levels predicts resistance to fluoropyrimidines, a result consistent with reports in the literature (Copur, et al. (1995); Banerjee, et al. (1998)).

5. Inhibitors of NB1011-mediated Cytotoxicity.

Tomudex is a chemotherapeutic that acts primarily via inhibition of TS. If NB1011 exerts cytotoxicity via the TS enzyme, then inhibition of TS with Tomudex should decrease NB1011-mediated cytotoxicity. To test this hypothesis directly, Tomudex-resistant MCF7 cells, which overexpress TS 11-fold compared to the parental MCF7 cell line, were exposed to NB1011 in the presence of increasing concentrations of TDX. Cells were plated and exposed to indicated concentrations of compound(s) as described above. Results are shown in Table 7.

The data show that blockade of TS using the specific inhibitor Tomudex, results in up to about 25-fold inhibition of NB1011-mediated cytotoxicity. These results support the concept that activity of NB1011 results from its metabolism by TS.

To further characterize the intracellular metabolism of NB1011, combination experiments with leucovorin (LV; 5-formyltetrahydrofolate) were performed. This experiment was initiated because we had observed that THF stimulates production of fluorescent product(s) in the cell-free reaction of BVdUMP and rHuTS. It was hypothesized that if the fluorescent products are related to the cytotoxic effects of NB1011, then enhancing intracellular levels of THF by providing LV in the culture media would also enhance NB1011-mediated cytotoxic effects. Surprisingly, in the presence of 3 µM LV, NB1011 activity on the H630R10 cell line was diminished by more than 90%, compared to NB1011 alone, as determined in the alamarBlue assay. The fact that NB1011 activity is abolished by LV, which supplements intracellular reduced folate pools, suggests that NB1011 may work in part by diminishing these pools. Alternatively, LV (or a metabolite) could directly impact the metabolism of BVdUMP by interfering with its interaction with TS.

To explore whether LV could directly impact the reaction of BVdUMP with TS, reactions were carried out +/−THF with BVdUMP, or with THF+dUMP, and +/−Methotrexate (MTX), LV or Tomudex (TDX).

The results (Table 8) are surprising in two respects: 1). Although an increase in fluorescent product was noted from BVdUMP in the presence of THF, a decreased rate of substrate consumption (BVdUMP) utilization occurs in the presence of the cofactor; and 2). In the presence of cofactor, all three compounds tested (MTX, TDX and LV) dramatically inhibited the BVdUMP+rHuTS reaction. In each case, the inhibition was more pronounced than that seen in the dUMP+ rHuTS reaction, or the reactions with BVdUMP in the absence of THF.

The results described above, demonstrating inhibition of the BVdUMP+TS reaction by LV, MTX and TDX, and further, that this effect is more pronounced in the presence of cofactor (THF), suggests that NB1011 activity may be modulated by other chemotherapeutics. Importantly, rescue of NB1011-treated cells is feasible by providing LV, similar to the LV rescue from MTX. In the case of MLX, LV rescue occurs via supplementation of intracellular folate pools, which are diminished via MTX inhibition of dihydrofolate reductase and TS. If reduced folates are diminished within the cell during BVdUMP reaction with TS, then other compounds that diminish intracellular thymidine or purine nucleotide pools by distinct mechanisms may give additive or synergistic anti-cellular effects when used together with NB1011. Examples of such compounds (Dorr and Von Hoff (1994)),include 6-mercaptopurine, thioguanine and 2i-deoxycoformycin, all of which interfere with purine metabolism. Azacytidine-mediated inhibition of orotidylate decarboxylase blocks pyrimidine biosynthesis, and so could lower intracellular thymidine levels in a cell by a mechanism distinct from that of NB 1011.

Pharmacogenomics of TS ECTA

1. Comparison of TS and HER2.

Figures 5A, 5B:
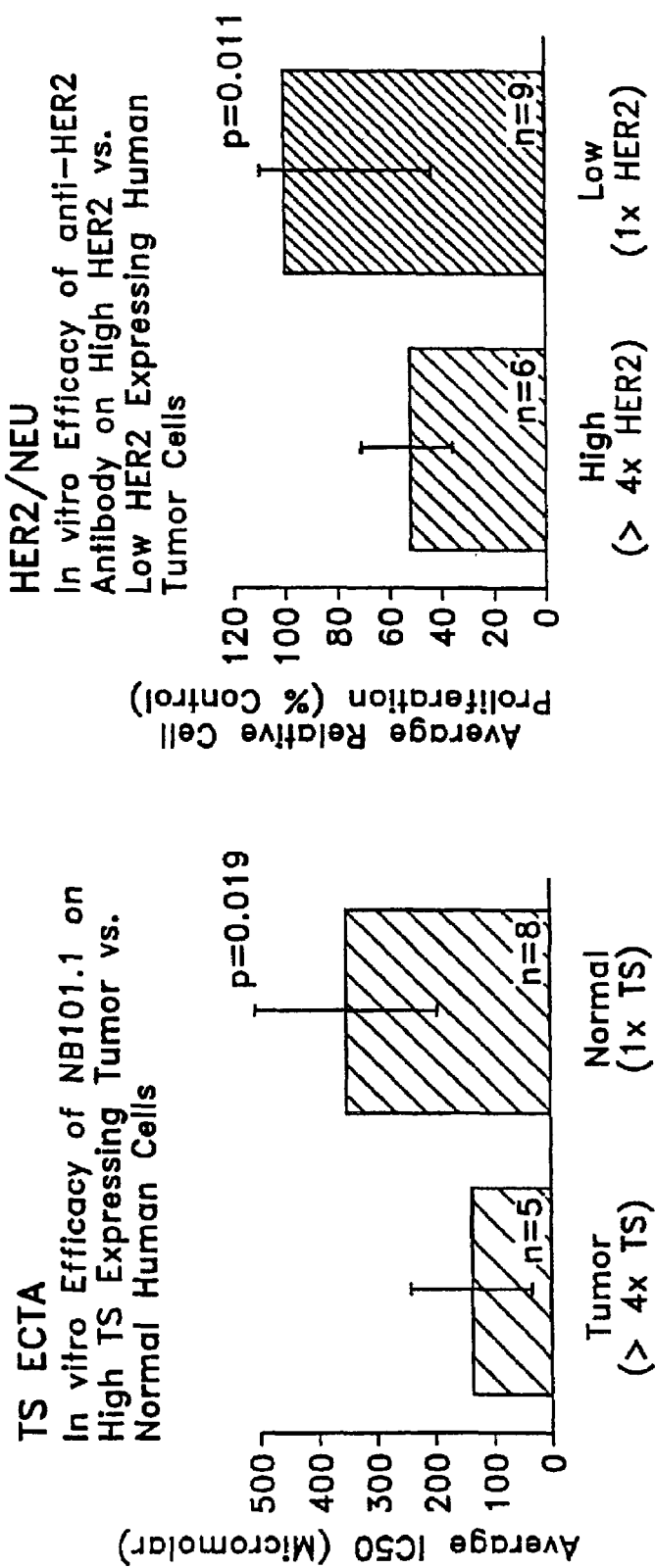
FIGS. 5A and 5B show that there are marked similarities between in vitro efficacy requirements for NB1011 and anti-HER2. A), Data are taken from Tables 4, 5, and 8. B). Data from Shepard, et al. (1991). Vertical bars show standard error of means calculated using the Mann-Whitney U test.
Figure 6:
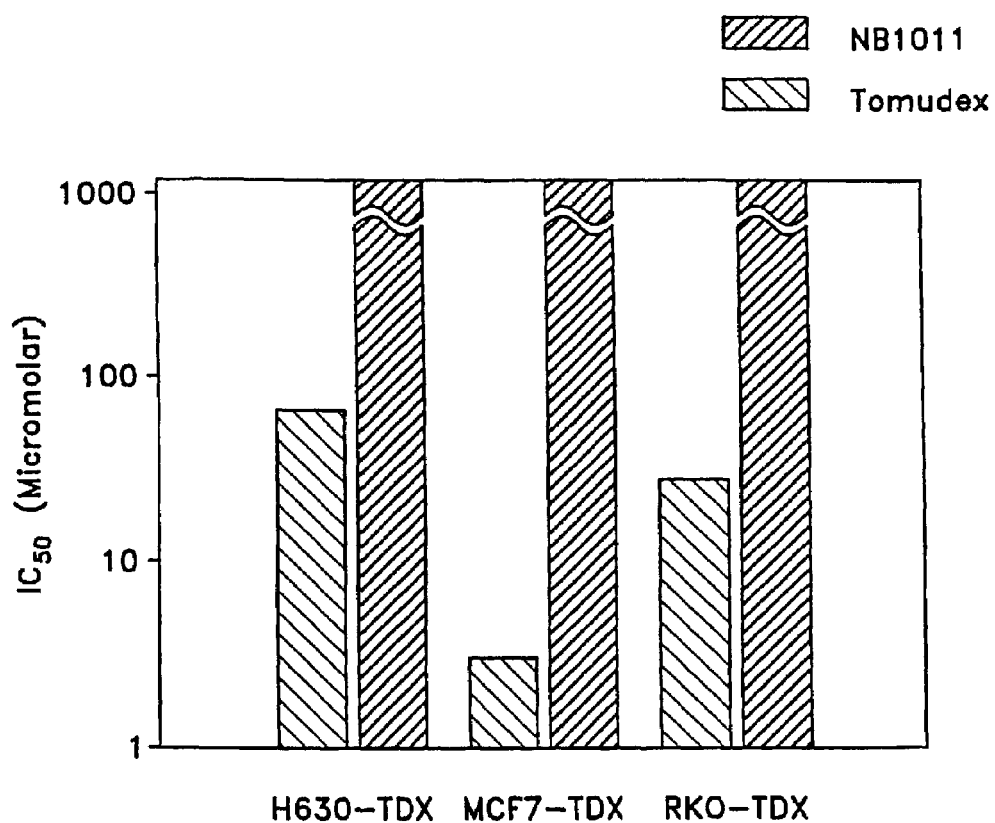
FIG. 6 shows that NB1011 is highly active against Tomudex resistant cancers. Cytotoxicity vs. $TDX^R$ cell lines was measured in the alamarBlue assay, as described in Materials and Methods, below.
Figure 7:
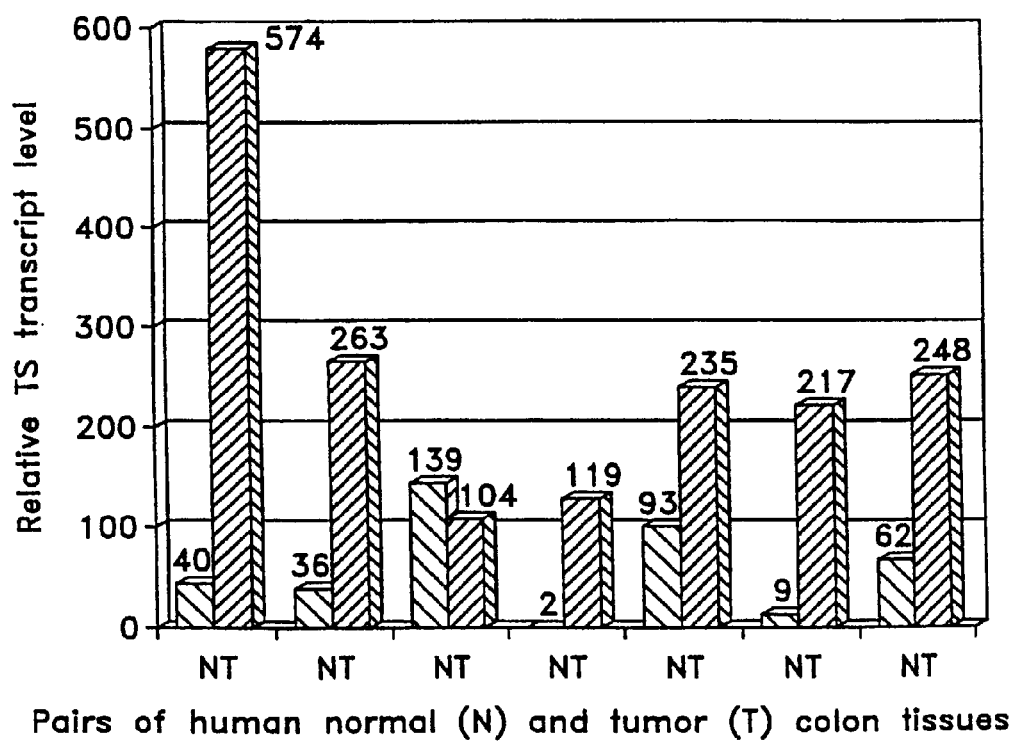
FIG. 7 shows transcript levels of thymidylate synthase in human normal and tumor colon tissues. RT-PCR analysis was performed as described in Materials and Methods, below. The ratio of TS mRNA in tumor vs. normal tissue samples, each normalized to β-actin was (left to right) 14.35, 7.31, 0.75, 59.5, 2.53, 24.1, and 4.0.

An important aspect of the current approach to discovery and development of novel therapeutics is the ability to identify patients who are most likely to respond to treatment (a positive pharmacogenomics selection). One of the pioneering drugs in this area is Herceptin, now used to treat breast cancers which overexpress the HER2 protooncogene. Early data with anti-HER2 antibodies showed that activity on randomly selected tumor cells and normal cells was minimal. However, if tumor cell lines were selected that had at least a 4-fold increased expression of HER2, then a significant activity and anti-HER2 antibody could be demonstrated, as compared to normal cells or tumor cells expressing lower amounts of the HER2 gene product (Shepard, et al. (1991) and (Lewis (1993)). The data shown in FIGS. 5A and 5B demonstrate that, similarly to the case with Herceptin.

The cell line results shown in FIG. 2 may suggest an additional similarity between the TS and HER2/NEU systems. The similarity is that each has a similar overexpression requirement (about 4-fold) which predicts more aggressive disease for both TS and HER2/NEU overexpressing patients (Johnston, et al. (1994)).

2. NB1011 is Active Against 5FU and Tomudex-resistant Colon and Breast Tumor Cell Lines.

Because NB1011 has promising anticancer activity, it is important to compare it with other chemotherapeutics with respect to safety. The utility of NB1011 in the treatment of cancer is further strengthened when it is compared with Tomudex, a chemotherapeutic which, like 5FU, is often used to treat colon and breast cancer, among other malignancies.

The results (FIG. 10) show that while NB1011 is more than 10-fold less toxic than TDX vs. normal cells (CCD18co), it is more than 30-fold more potent than TDX on MCF7-TDX resistant tumor cells. Similar results have been obtained for other TDX-resistant tumor cell lines. The low level of toxicity vs. normal cells and the high activity vs. $TDX^R$ tumor cells supports the application of NB1011 to drug resistant cancers that overexpress TS.

3. NB1011 is More Dependent Upon TS Protein Levels than TS Activity as Measured by Tritium Release from dUMP-$^3$H.

Four types of assays have been used to characterize TS levels in cells and tissues. Most commonly used is the antibody-based technique (Johnston (1994) and (Johnston (1995)) but RT-PCR, 5FdUMP-binding and tritium release (van Laar (1996), van Triest (1999), Jackman (1995), Larsson (1996), Komaki (1995) and Mulder (1994)) have also been measured in various studies. For characterization of cell lines we have focused on Western blotting and tritium release from $^3$H-dUMP. These assays were chosen because antibody-detection is commonly used for clinical samples and tritium release from labeled deoxyuridine is a direct measure of TS catalytic activity in cells.

Cells were grown and characterized as described above. TS expression level is relative to CCD18co, a normal colon epithelial cell line. Tritium release is background substracted as described in Methods. ND=Not detectable above background.

Analysis of the data presented in Table 7 indicates that there is a closer relationship between TS protein level and sensitivity to NB1011 than between TS activity (tritium release from $^3$H-dUMP) and NB1011 sensitivity. In each set of matched parental and drug-resistant tumor cell types, the drug-resistant derivatives, each with more TS protein than the parent, also have an increased sensitivity to NB1011. However, when the same comparison is done with respect to TS activity, the parental cell lines often have comparable, or greater, TS activity and are less sensitive to NB1011-mediated cytotoxicity.

While these results could occur via a number of different mechanisms, or combinations of mechanisms, it is likely that $^3$H-dUMP conversion to dTMP (and accompanying tritium release) may be subject to limitation by some component, perhaps cofactor availability. However, since conversion of BVdUMP is not dependent upon cofactor, then its reaction with TS can continue even in a cellular milieu in which cofactor is limiting. This observation is important because TS substrates as therapeutics would not be attempted based upon the results of typical tritium release assays for TS activity in which the most aggressive, and drug-resistant, tumor cells are observed to have a lower TS activity than their precursors. These results lend additional support to the proposal of selecting patients for TS ECTA therapy based simply on the level of TS detected by antibody staining.

4. TS Levels in Tumor Samples Often Exceed a 4-fold Increase Over Normal Tissue.

The results shown above suggest that TS ECTA therapy, at least with NB1011, will be most effective when used in patients whose cancers overexpress TS at least four-fold.

Figure 9:
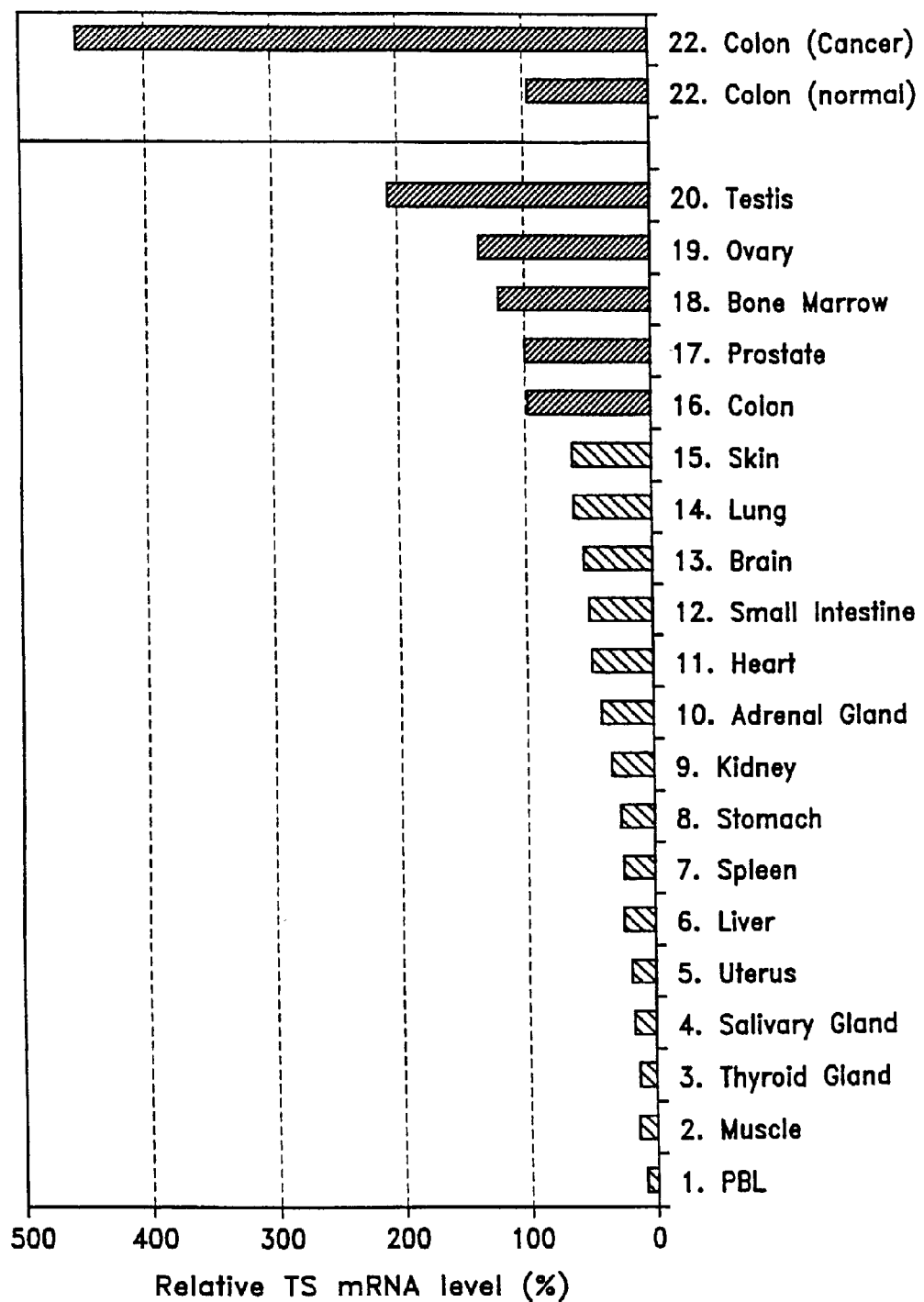
FIG. 9 is a graph showing mRNA levels of TS in multiple human tissues. TS mRNA levels were determined by using RT-PCR. The DNA bands corresponding to thymidylate synthase were quantified and normalized to that of β-actin by Molecular Dynamics Storm. Column 1 to 20 indicate the TS mRNA level in human normal tissues. The expression levels are expressed as values relative to that of colon (column 16). Columns 21 and 22 show the average TS transcript levels in 7 matched colon normal and cancer tissues. The expression values were relative to that of normal colon tissues (column 21).

The literature (Johnston (1994), Bathe (1999), Leichman (1998) and Lenz (1995)) suggests that overexpression in the range of 4-fold occurs in about 50% of cancers, and furthermore, that this level of overexpression predicts a more aggressive disease. To confirm the frequency of at least 4-fold overexpression of TS in human colon cancer, we obtained matched normal and tumor samples from the Cooperative Human Tissue Network. These samples were analyzed for TS mRNA level via RT-PCR, which gives results comparable to immunohistochemistry (Johnston, et al. (1994)). The results of the RT-PCR evaluation of the samples is shown in FIG. 9.

Five of the seven samples analyzed above have at least a 4-fold level of overexpressed TS as determined by the RT-PCR assay. None of these patients were previously treated with chemotherapy, which suggests that this frequency and level of overexpression is associated with invasive disease and not due to selection by chemotherapy. It is expected that cancer cells that have been exposed to TS inhibitors such as Tomudex or the anabolic derivative of 5FU or 5-FdUrd, 5FdUMP, may be selected for increased expression (Lonn, et al. (1996)). The average degree of overexpression, as measured by RT-PCR for all 7 samples, is about 4.7-fold. These data suggest that greater than 4-fold overexpression of TS in tumor foci is a common event.

5. Experimental Therapy of 5FU-resistant Human Colon Cancer.

The most important diseases for new compounds that target TS are the gastrointestinal cancers. To study the activity of NB1011 in an in vivo model, H630R10, 5FU-resistant human colon cancer cells, were grown subcutaneously to an average tumor size of 50 mm³ in nude mice. The mice were then treated, with excipient (DMSO, 5FU or NB1011).

Figure 8A:
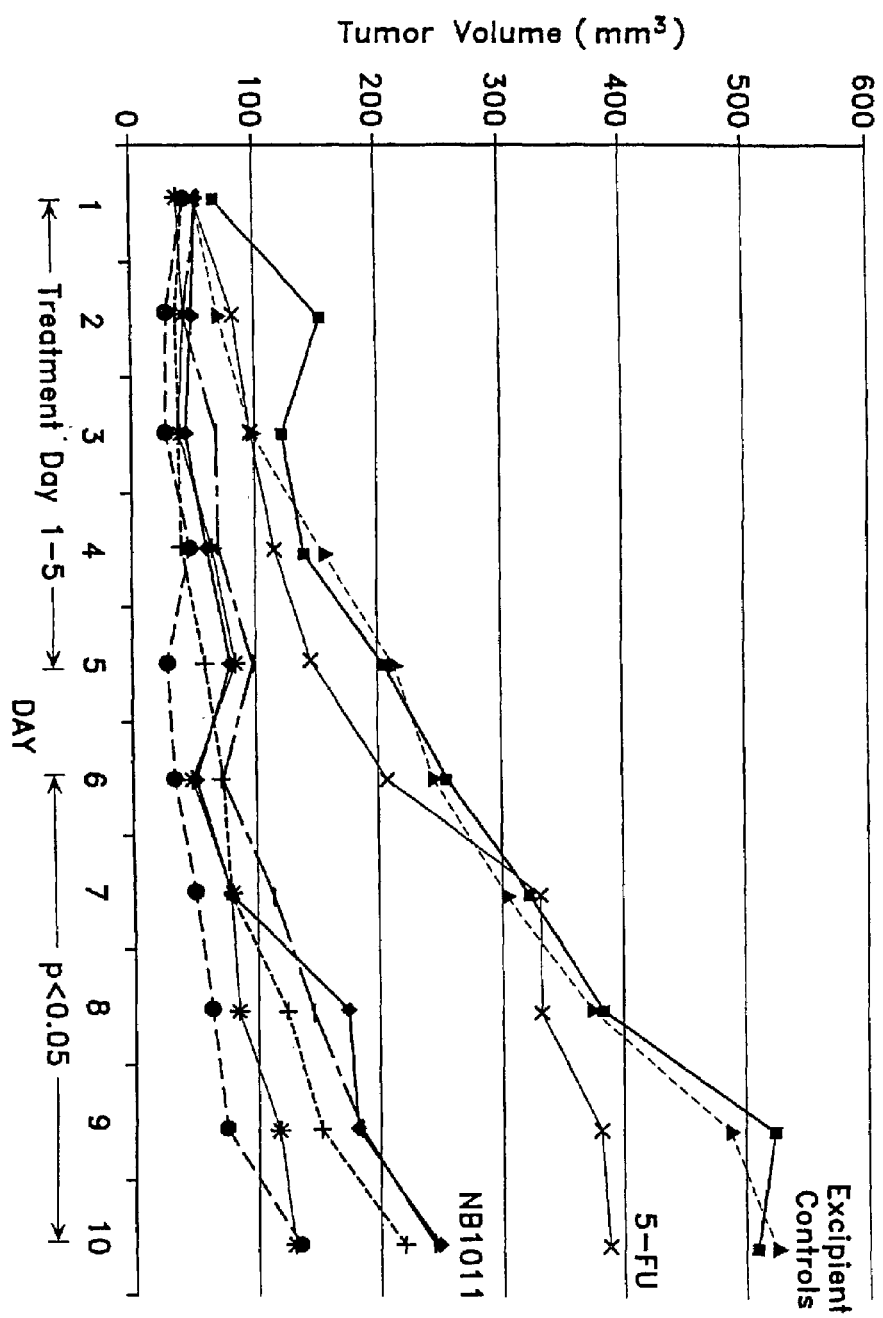
FIG. 8A shows that NB1011 inhibits growth of 5-FU resistant colon cancer. Treatment of nude mice bearing H630R10 (5FU Resistant) human colon carcinoma. Tumor measurements began on the first day of treatment (Day 1).
Figure 8B:
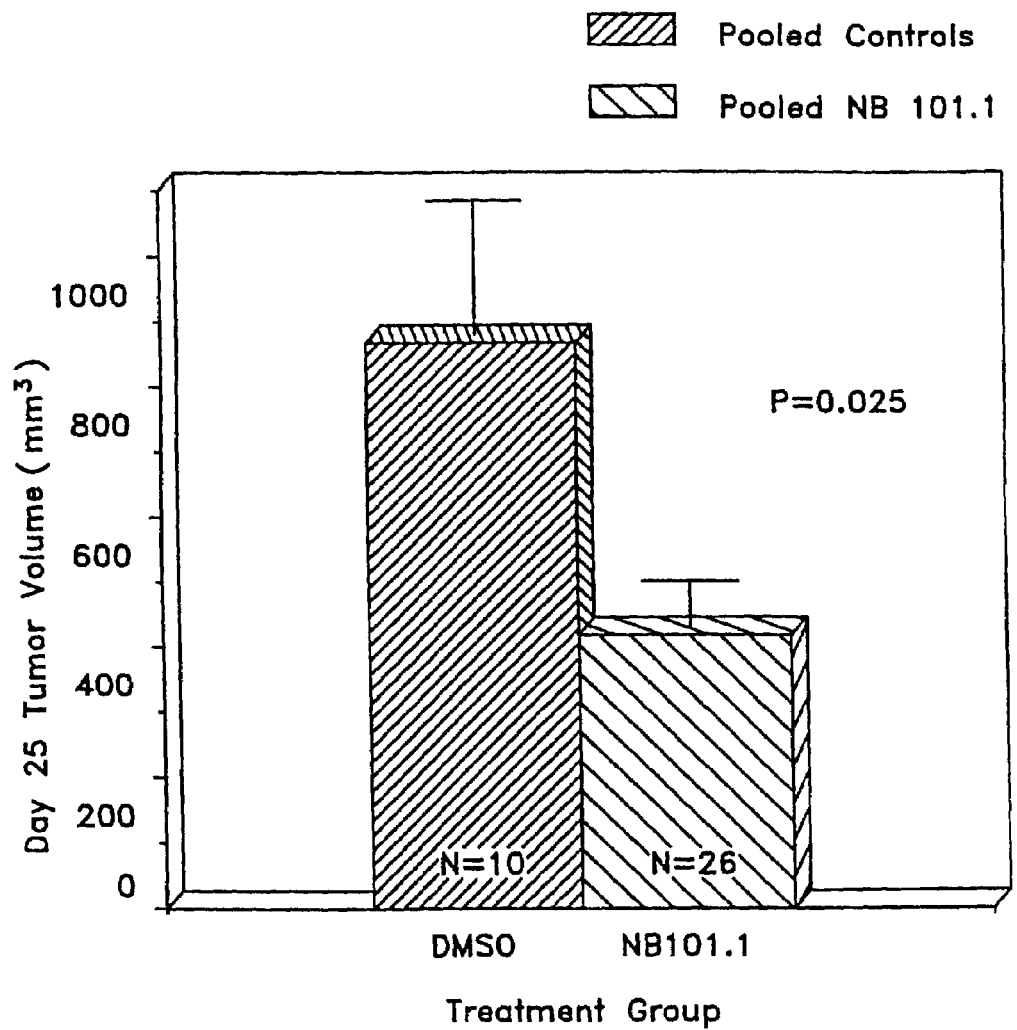
FIG. 8B shows long term response to NB1011. Analysis of pooled data at Day 25. Statistical analysis is described in the Materials and Methods section below.

Doses of 3.5 mg, 2.5 mg, and 1.25 mg of NB1011 were administered daily for 5 days, either peritumorally or intraperitoneally to tumor-bearing mice. FIG. 8A shows the initial block in tumor growth induced by treatment for 5 days with NB1011, as compared to excipient or 5FU treated animals. Although no statistically significant dose response relationship is evident among the NB1011 groups, there is a significant difference between the NB1011 groups vs. either the 5FU or excipient controls, starting with Day 6. This difference is maintained (FIG. 9B) until the control animals were sacrificed at Day 25, even though therapy was discontinued after Day 5.

TABLE 3

Comparison of Kinetic Parameters of Bacterial and rHuTS

| Kinetic Constants | *Lactobacillus casei* | rHuTS |
|---|---|---|
| dump | | |
| $K_m$ | 3.0 μM | 7.7 μM |
| $K_{cat}$ | 6.4 s⁻¹ | 0.2 s⁻¹ |

TABLE 3-continued

Comparison of Kinetic Parameters of Bacterial and rHuTS

| Kinetic Constants | *Lactobacillus casei* | rHuTS |
|---|---|---|
| $K_{cat}/K_m$ | $2.1 \times 10^6 \, M^{-1} s^{-1}$ | $2.6 \times 10^4 \, M^{-1} s^{-1}$ |
| $K_i$ (of BVdUMP) | 0.6 μM | 4.5 μM |
| BVdUMP | | |
| $K_m$ | 3.3 μM | 16 μM |
| $K_{cat}$ | 0.018 s⁻¹ | 0.0067 s⁻¹ |
| $K_{cat}/K_m$ | $5.6 \times 10^3 \, M^{-1} s^{-1}$ | $4.2 \times 10^3 \, M^{-1} s^{-1}$ |
| $K_i$ (of dUMP) | 2.0 μM | 17.5 μM |
| Relative catalytic efficiency (dUMP vs BVdUMP) | 385-fold | 60-fold |

Enzyme kinetics were done as described in Methods. Data for *Lactobacillus casei* are derived from Barr, et al. (1983) supra. The rHuTS was prepared as described in Materials and Methods, above.

TABLE 4

Inhibition of rHuTS reactions by Tomudex and 5-FdUMP

| Substrate + Cofactor | No Inhibitor | Tomusdex (500 nM) | 5-FdUMP (500 nM) |
|---|---|---|---|
| BVdUMP + THF | 109 ± 16 RFU/min (100%) | 67 ± 3 (61%) | 44 ± 2 (40%) |
| BVdUMP − THF | 75 ± 11 (100%) | 34 ± 3 (45%) | 93 ± 13 (129%) |
| dUMP + THF | 1500 ± 20 nmoles/min (100%) | 690 ± 40 (46%) | 290 ± 70 (19%) |

Inhibition of rHuTS reactions by Tomudex and 5-FdUMP. Thymidylate synthase reactions containing enzyme inhibitors or cofactor were incubated at 30° C. as described in Materials and Methods, and the initial rates of the enzyme reaction were determined by measuring the increase in relative fluorescence units at 340 nm excitation, 595 nm emission for the BVdUMP reactions, or increase in $A_{340}$ for the dUMP reaction.

TABLE 5

Cytotoxicity of NB1011 vs. 5FU on Normal and Tumor Cell Strains

| | IC₅₀ (μM) | | | IC₅₀ (μM) | |
|---|---|---|---|---|---|
| Normal Cells | NB101.1 | 5FU | Tumor Cells | NB101.1 | 5FU |
| CCD1800 (Colon) | 562 | 2.0 | H630R10 (Colon) | 65 | 41.6 |
| DET551 (Skin) | 262 | 0.8 | HT1080 (Colon) | 449 | 0.8 |
| NHDF (Skin) | 359 | 0.8 | COLO320 (Colon) | 401 | 1.5 |
| H527 (Skin) | 273 | 1.6 | COLO205 (Colon) | 105 | 1.3 |
| W138 (Lung) | 335 | 1.0 | SW620 (Colon) | 374 | 4.6 |
| MRC9 (Lung) | 303 | 1.1 | SKCO1 (Colon) | 184 | 1.4 |
| NHLF (Lung) | 139 | 0.9 | HCTC (Colon) | 280 | 2.8 |
| NHA (Brain) | 839 | 0.9 | MCF7 (Breast) | 141 | 1.0 |
| NHOST (Bone) | 642 | 4.7 | MDAMB361 (Breast) | 365 | 5.0 |
| NPRSC (Prostate) | 369 | 1.7 | MDAMB468 (Breast) | 172 | 4.4 |
| NHEPF (Liver) | 2085 | 1.7 | SW527 (Breast) | 431 | 4.3 |
| Average | 561 | 1.6 | NCI H520 (Lung) | 135 | 0.6 |
| | | | SKLU1 (Lung) | 270 | 7.9 |
| | | | SOAS2 (Bone) | 232 | 1.4 |
| | | | PANC1 (Pancreas) | 492 | 1.9 |
| | | | SKOV3 (Ovary) | 484 | 3.0 |
| | | | PC3 (Prostate) | 184 | 0.9 |
| | | | HEPG2 (Liver) | 704 | 22.8 |
| | | | SKHEP1 (Liver) | 247 | 1.7 |

TABLE 5-continued

Cytotoxicity of NB1011 vs. 5FU on Normal and Tumor Cell Strains

| | | |
|---|---|---|
| A431 (Skin) | 266 | 0.2 |
| MCIxc (Brain) | 61. | 1.2 |
| Average | 288 | 5.3 |

| | NB101.1 | 5FU |
|---|---|---|
| Therapeutic index (N/T) | 1.95 | 0.30 |

Cells were analyzed for response to either NB1011 or 5FU in the alamarBlue assay (Methods). All assays were performed at least three times. The standard deviation is less than 20%. Therapeutic index was calculated as the ratio of $IC_{50}$ (mean of all cell types) to $IC_{50}$ (mean of all tumor cell lines).

TABLE 6

NB1011 cytotoxicity on cell lines engineered to express HuTS.

| | | $IC_{50}$ | | | |
|---|---|---|---|---|---|
| Cell Line | TS Level (%)* | NB1011 (μM) | FUDR (μM) | 5-FU (μM) | TDX (μM) |
| C/HT1080 | 100 | 320 | <0.1 | 1.0 | 3.6 |
| TSL/HT1080 | 409 | 196 | 2.2 | 1.7 | 24 |
| TSL/HT1080 | 702 | 0.8 | 3.1 | 3.5 | 153 |

A cDNA encoding rHuTS was subcloned into ventor pEGFP-C3, in-frame with GFP. The construct was transfected into HT1080 cells and selected with G418 (750 ug/ml) in order to obtain clones that stably express fusion rHuTS. Individual cells were cloned based upon high or low fluorescence expression as described in Methods.

*TS levels were determined by using Western blot analysis, the quantified expression levels were expressed as values relative to that of cell strain CCD18co.

TABLE 7

Tomudex Inhibits NB1011 Mediated Cytotoxicity

| [Tomudex] (nM) | 0 nM | 1 nM | 10 nM | 100 nM | 1000 nM |
|---|---|---|---|---|---|
| NB1011 $IC_{50}$ (μM) | 5.7 | 25.5 | 87.7 | 140.3 | 103.0 |
| Fold Protection | 1 | 4.5× | 15.4× | 24.6× | 18.1× |

The Tomudex rescue assay (alamarBlue) was done with TDX-resistant MCF7 breast tumor cells as described in Methods.
"Fold Protection" was calculated as the ratio of $IC_{50}$ with and without added TDX.

TABLE 8

Impact of Folate Inhibitors

| Inhibitor | BVdUMP, with THF | BVdUMP, w/o THF | dUMP, with THF |
|---|---|---|---|
| None | 100% | 138% | 100% |
| MTX | 10% | 24% | 31% |
| LV | 17% | 97% | 77% |
| TDX | 0% | 25% | 18% |

Cell-free assays using rHuTS, the appropriate substrate and other components were combined as described in Methods. MTX (140 μM), LV (140 μM) or TDX (5 μM) were added to evaluate their inhibitory activity. Utilization of substrate (either BVdUMP or THF) was employed as a measure of reaction rate. The numbers indicate remaining activity.

TABLE 9

NB1011 activity is more associated with TS protein than with tritium release

| Cell Line | Drug Selection | TS Protein | Tritium Release | NB1011-$IC_{50}$ |
|---|---|---|---|---|
| H630 | None | 288 | 3206 | 414 |
| Colon cancer | 5FU | 2350 | 1840 | 65 |
| | TDX | 671 | 3980 | 2.3 |
| RKO | None | 142 | 4920 | 136 |
| Colon cancer | TDX | 279 | 1625 | 28 |
| MCF7 | None | 178 | 5185 | 327 |
| Breast cancer | TDX | 1980 | 875 | 2.8 |
| N1S1 | None | 197 | 12,565 | 494 |
| | 5FU | 1241 | ND | 204 |

TABLE 10

MDF7 TDX cells selected for resistance to NB1011 are more sensitive to 5-Fluorouracil and Tomudex

| | $IC_{50}$ (micromolar)* | | | Relative TS Protein Level |
|---|---|---|---|---|
| | 5-FU | Tomudex | NB1011 | |
| MCF7 | 10– | .026– | 291– | 1X– |
| MCF7 TDX | 32 | >10 | 2 | 11X |
| MCF7 TDX/1011 | 2 | .041 | 240 | 4X |

*= as determined by the alamarBlue assay described in Materials and Methods
TDX = Tomudex;
1011 = NB 1011

EXAMPLE 19

Co-Administration

Cell lines: Normal human colon epithelial cells (CCD18co) and skin fibroblasts (Det55 1) were purchased from ATCC (Rockville, Md.). MCF7TDX, human breast carcinoma cells resistant to 2 μM Tomudex were obtained from Dr. Patrick Johnston, Queens University, Belfast. H630R10, human colorectal carcinoma cells resistant to 10 μM 5-Fluorouracil were obtained from Dr. Edward Chu (Yale Cancer Center) and Dr. Dennis Slamon (UCLA). The MCF7TDX and the H630R10 cell lines have been previously described in Drake, J. C. et al. (1996) and Copur, S. et al. (1995) respectively.

Chemicals: Dipyridamole and nitrobenzylthioinosine were purchased from ICN Biomedicals (Aurora, Ohio). 5-Fluorouracil was purchased from Sigma (St. Louis, MO).

Tomudex was provided by Zeneca (Wilmington, Del.).

Culture Conditions: All cells were cultured under standard conditions of 37° C., 95% humidified air, 5% $CO_2$ in RPMI 1640 culture medium containing 10% fetal calf serum (Life Technologies) and penicillin/streptomycin/fungizone. MCF7TDX cells were maintained continuously in 2 μM Tomudex, and H630R10 cells were maintained continuously in 10 μM 5-FU. The medium was renewed or the cells were passaged about every three days to maintain optimal growth conditions. Normal cells were passaged a maximum of 15 times to avoid senescence.

Cytotoxicity Studies: 384-well interaction screening assay. 500 cells per well were transferred to a 384-well tissue culture plate (Corning Inc., Corning, N.Y.) and allowed to attach for 24 hours in standard culture conditions. Compounds were then applied in a bidirectional (checker board) pattern (Chou, T. C. and Talalay, P. (1984)). Following a 5-day incubation, the redox indicator dye, alamarBlue (AccuMed International, Westlake, Ohio) was added to each well at a 10% v/v ratio, and fluorescence was monitored at 535 excitation, 595 emission. Cytotoxic effect levels and drug interactions were assessed by the combination index method (Chou, T. C. and Talalay, P. (1984) and Bible, K. C. et al. (1997)), described briefly below. 96-well combination cytotoxicity assay. Exponentially growing cells were transferred at a density of 1.0-$5.5 \times 10^3$ cells per well to a 96-well tissue culture plate and allowed to attach for 24 hours. Compounds were then applied in duplicate half log serial dilutions. Each compound was tested separately, and mixed together at a single molar ratio approximately equal to the ratio of the individual $IC_{50}$ values. After an additional 72 hour incubation, cells were washed once with PBS and stained with 0.5% crystal violet in methanol. Plates were washed gently in water to remove unbound stain and allowed to dry overnight. Crystal violet stain bound to the total protein of attached cells was redissolved in Sorenson's buffer (0.025M sodium citrate, 0.025M citric acid in 50% ethanol), and absorbance monitored at 535 nM. Sigmoid curves were fit according to the Hill inhibitory Emax model, and $IC_{50}$ calculated as the average of three or more separate determinations. Where applicable, the combination index for multiple drug effects was calculated according to the median-effect principle (Chou, T. C. and Talalay, P. (1984)) using the CalcuSyn software from Biosoft (Ferguson, Mo.). Briefly, the ICso and the slope parameter (m) for each agent alone were determined from the median effect plot, an x,y plot of log(D) vs log $(f_a/f_u)$ based on Chou's median effect equation:

$$f_a/f_u = (D/D_m)^m \quad \text{[Equation 1]}$$

where D=dose of the drug, $D_m=IC_{50}$ as determined from the x-intercept of the median effect plot, $f_a$=fraction of cells affected, $f_u$=fraction of cells unaffected ($f_u = 1-f_a$), and m=an exponent signifying the steepness of the sigmoid dose-effect curve. Only experiments with linear correlation coefficients (r) >0.9 were accepted for analysis. A combination index (CI) was then calculated to assess synergism or antagonism according to the following equation which assumes an independent mechanism of drug action (mutual exclusivity):

$$CI = (D)_1/(D_x)_1 + (D)_2/(D_x)_2 + (D)_1(D)_2/(D_x)_1(D_x)_2 \quad \text{[Equation 2]}$$

where $(D)_1$ and $(D)_2$ are the concentrations of drug 1 and drug 2 which combined produce x% inhibition, and $(D_x)_1$ and $(D_x)_2$ are the concentrations of each drug which alone produce x% inhibition. CI=1 indicates an additive interaction, CI<1 indicates synergy, and CI>1 indicates antagonism. For each experiment CI's from several different effect levels and concentrations of a constant molar ratio were averaged. Student t-tests were applied to determine if the average differed significantly from 1.

Results:

384-well screening studies. To identify drugs which potentially synergize with NB1011, combination cytotoxicity experiments were performed with NB1011 and each of 10 antitumor agents from several different mechanistic classes using MCF7TDX and H630R10 tumor cells. Results from these initial 384-well alamarBlue screening assays are shown in Table 11. In general, a combination index of <1 indicates synergy, ~1 indicates additivity, and >1 indicates antagonism (Pegram, M. D. et al. (1999)).

TABLE 11

Drugs screened for interaction with NB1011

| | | Combination Index ± s.e.m. | |
|---|---|---|---|
| Drug | Class | MCF7TDX | H630R10 |
| Irinotecan | Inhibition of topoisomerase I | 1.36 ± 0.38 | 1.26 ± 0.20 |
| topotecan | | 2.45 ± 0.85 | ND |
| Etoposide | Inhibition of topoisomerase II | 3.13 ± 0.58 | 1.96 ± 0.28 |
| Vinblastine | Inhibition of microtubule assembly | 1.09 ± 0.16 | 0.78 ± 0.32 |
| Taxol | Stabilization of microtubules | 1.41 ± 0.32 | 0.99 ± 0.15 |
| Cisplatin | DNA damage | 1.51 ± 0.35 | ND |
| Thiotepa | Alkylation | 2.23 ± 0.45 | ND |
| Doxorubicin | Inhibition of nucleic acid synthesis | 0.55 ± 0.06 | 1.05 ± 0.13 |
| 5-fluorouracil | Inhibition of TS, DNA/RNA incorporation | 3.19 ± 0.35 | ND |
| Methotrexate | Antifolate, inhibition of DHFR, TS | 1.78 ± 0.44 | ND |

ND = not determined.
Combination Index (CI) = 1 indicates additivity, CI < 1 indicates synergy, and CI > 1 indicates antagonism. CI calculated as the average of at least 4 consecutive dose / effect levels. Class of drugs as indicated by Dorr, R. T. and Van Hoff, D. D. (1994).

Two of the ten agents screened, vinblastine and doxorubicin, showed potential synergy (CI≦1.1) with NB1011 in MCF7TDX and H630R10 cell. Two of the remaining 8 agents, irinotecan and taxol showed an additive or antagonistic interaction (CI=1-1.4) with NB1011, while all the other agents showed antagonism (CI>1.5). The most antagonistic interaction was observed with 5-Fluorouracil which gave CI=3.19 in MCF7TDX cells. In light of these results, vinblastine and doxorubicin were chosen for further study using a 96-well crystal violet combination cytotoxicity assay. 96-well combination cytotoxicity studies. The 96-well format was chosen for more detailed drug interaction studies. Three additional agents were included in the 96-well assay: oxaliplatin, a new platinum analog DNA damaging agent; dipyridamole (DP) and p-nitrobenzylthioinosine (NBMPR), both potent inhibitors of equilibrative nucleoside transport processes. Oxaliplatin was tested to confirm the antagonism results for cisplatin. The nucleoside transport inhibitors were tested because published data (Tsavaris, N. et al.(1990), Grem, J. L. (1992) and Wright, A. M. et al. (2000)) suggested they may modulate the activity of nucleoside based drugs. To analyze whether any of these drugs would enhance the activity of NB1011 specifically in tumor cells, two normal cell types, Det551 and CCD18co, were included in the assays.

Results of these experiments are shown in Table 12.

TABLE 12

Average combination index (CI) values for drugs tested in combination with NB1011 in tumor and normal cells

| Drug | Cell Line | CI | ±SEM | P value | Molar Ratio[a] | NB1011 Dose (µM) | Drug Dose (µM) | Interaction[b] |
|---|---|---|---|---|---|---|---|---|
| Dipyridamole | H630R10 | 0.75 | 0.11 | 0.052 | 2 | 11-150 | 5.5-75 | Syn |
| | MCF7TDX | 0.51 | 0.06 | 0.001 | 0.2 | 1.1-3.2 | 5.5-16 | Syn |
| | Det551 | 1.17 | 0.23 | 0.484 | 5 | 5.8-375 | 1.2-75 | Add |
| | CCD18co | 1.30 | 0.08 | 0.008 | 5 | 81-375 | 16-75 | Ant |
| p-Nitrobenzyl-Thioinosine (NBMPR) | H630R10 | 0.35 | 0.07 | 0.001 | 1 | 1.5-500 | 1.5-500 | Syn |
| | MCF7TDX | 0.57 | 0.17 | 0.029 | 3.33 | 0.15-150 | 0.045-45 | Syn |
| | Det551 | 1.43 | 0.16 | 0.026 | 3.33 | 32-300 | 9.7-90 | Ant |
| | CCD18co | 3.93 | 1.00 | 0.019 | 3.33 | 32-300 | 9.7-90 | Ant |
| Vinblastine | H630R10 | 0.63 | 0.10 | 0.003 | 6000 | 4.1-54 | 0.0005-0.015 | Syn |
| | MCF7TDX | 1.44 | 0.29 | 0.186 | 2000 | 0.4-1.9 | 0.0005-0.015 | Ant |
| | Det551 | 0.54 | 0.10 | 0.003 | 50000 | 2.9-47 | 0.0005-0.015 | Syn |
| | CCD18co | 0.65 | 0.10 | 0.008 | 50000 | 17-135 | 0.0005-0.015 | Syn |
| Oxaliplatin | H630R10 | 1.78 | 0.06 | 0.001 | 120 | 6.9-150 | 0.1-1.3 | Ant |
| | MCF7TDX | 2.24 | 0.33 | 0.004 | 12 | 0.6-15 | 0.1-1.3 | Ant |
| Doxorubicin | H630R10 | 1.39 | 0.13 | 0.012 | 300 | 117-150 | 0.039-0.5 | Ant |
| | MCF7TDX | 1.96 | 0.25 | 0.004 | 600 | 1.9-15 | 0.001-0.025 | Ant |

[a] Molar ratio of NB1011:Drug.
[b] Syn = synergy,
Ant = antagonism,
Add = additivity.

As can be seen in Table 12, doxorubicin, although promising in the initial screening assay, failed to synergize in the more detailed 96 well cytotoxicity assay (CI=1.39 and 1.96 in H630R10 and MCF7TDX cells, respectively). Oxaliplatin had an antagonistic interaction in the tumor cells (CI=1.78 and 2.24, respectively). Since both oxaliplatin and doxorubicin antagonized NB1011 in the tumor cells, they were not tested in the normal cell assays. Consistent with the initial screening data, vinblastine synergized with NB1011 in H630R10 cells (CI=0.63), however it antagonized NB1011 in MCF7TDX cells (CI=1.44). Furthermore, in Det551 and CCD18co normal cells, vinblastine interacted synergistically with NB1011 to a similar extent as in H630R10 cells (CI=0.54 and 0.65, respectively). This lack of selectivity in the potentiation of NB1011 by vinblastine would most likely limit the use of this combination in the clinic. The nucleoside transport inhibitor, dipyridamole, synergized with NB1011 in the tumor cells (CI=0.75 and 0.51), but failed to synergize with NB1011 in the normal cells (CI=1.17 and 1.30). Similarly, NBMPR, another NT inhibitor, showed synergy with NB31011 in the tumor cells (CI=0.35 and 0.57), but produced no synergy in the normal cells (CI=1.43 and 3.93). Taken together this data indicate that 2 of the 13 agents tested, DP and NBMPR, which are both inhibitors of equilibrative nucleoside transport, potentiate the activity of NB1011. This enhancement of NB1011 activity by DP and NBMPR appears specific for the tumor cells tested, since no synergy was observed for these combinations in the two normal cell types analyzed.

EXAMPLE 20

Induction and Assessment of Arthritis

Arthritis was induced in male DBA/1 mice (8-10 weeks old) by intradermal injection of bovine type II collagen, purified in-house at the Kennedy Institute of Rheumatology as previously described (Miller, E. J. et al. (1972)). Collagen was administered in complete Freund's adjuvant (Difco, Detroit, Mich.). Onset of arthritis is expected to be variable. Arthritis onset is considered to occur on the day that swelling and/or erythema were observed. Clinical score is a composite of disease severity and the number of limbs affected, and is monitored daily from onset of disease and used as an assessment of disease progress. An example for scoring is: 0, Normal; 1, slight swelling with erythema; 2, pronounced swelling; 3, joint rigidity. In addition, the extent of paw swelling reflects the degree of edema in affected limbs.

Anti-TNF antibody used in these experiments was as described by Marinova-Mutafchieva, L. et al. (2000). NB1011 was administered daily by intraperitoneal administration at 2.5 mg total dose per day. Anti-TNF antibody was compared with NB1011 because, at present, antiTNF antibody is the optimal single agent for treatment of collagen induced arthritis (Marinova-Mutafchieva, L. et al. (2000)).

Success in this model has been shown to be predictive for clinical success in the development of new agents to treat inflammatory disease, especially rheumatoid arthritis (Elliott et al. (1994) and Feldmann et al. (1998)). This model therefore represents an ideal setting for establishing proof of concept for new agents to treat rheumatoid arthritis, and potentially other autoimmune and inflammatory diseases.

Following immunization with collagen, mice were maintained until a significant clinical score for disease progression was achieved (between 2.5 and 3.5). Mice were then treated with control saline injections, NB1011, or with anti-TNF antibody as a positive control. The results showed that the NB1011-treated group exhibited significant disease suppression ($p<0.05$), similar to the anti-TNF control, when compared with the saline-treated control group. There was no significant difference between the NB1011 and anti-TNF groups with regard to clinical score. Paw swelling is an alternative measure of CIA disease severity. When paw swelling was used as a criteria for disease suppression, comparable results were observed. In this second measure of efficacy, both the NB1011 and anti-TNF groups demonstrated significant disease suppression as compared to the saline-treated control group ($p<0.05$). Again, there was no significant difference between the NB1011 and anti-TNF groups, although suppression of swelling may have been less dramatic with NB1011. A further significant outcome of this work is that by comparison with earlier reported work, NB1011 appears to have activity superior to anti-angiogenesis agents, an anti-CD4 immunosuppressive agent, and cannabidiol, a third experimental agent currently being considered for use to treat rheumatoid arthritis, and potentially other autoimmune and inflammatory disorders (Malfait, A. M. et al. (2000); Miotla, J. et al. (2000); Marinova-Mutafchieva, L. et al. (2000)).

Although the foregoing invention has been described in some detail by way of illustration and example for purposes of clarity of understanding, it will be apparent to those skilled in the art that certain changes and modifications will be practiced. Therefore, the description and examples should not be construed as limiting the scope of the invention, which is delineated by the appended claims.

REFERENCES

Abraham et al. (1996) *J. Med. Chem.* 39:4569-4575
Akdas, A. et al. (1996) *Eur. Urol.* 29(4):483-486
Almasan et al. (1995) *PNAS, USA* 92:5436-40
Almasan et al. (1995b) *Can. Metastasis Rev.* 14:59-73
Almasan et al. (1995) *PNAS, USA* 92:5436-5440
Almasan et al. (1995b) *Can. Metastasis Rev.* 14:59-73
Anglada, J. M. et al. (1996) *J. Heterocycl. Chem.* 33:1259-1270
Aoki, M. et. al. (1999) *Hypertension* 34(2):192-200
Asakura, J. et al. (1988) *Tetrahedron Lett.* 29:2855-2858
Asakura, J. et al. (1990) *J. Org. Chem.* 55:4929-4933
Aupperle, K. R. et al. (1998) *Am. J. Pathol.* 152(4):1091-8
Balzarini, J. et al. (1985) *Methods Find. Exp. Clin. Pharmacol.* 7:19-28
Balzarini (1987) *Mol. Pharmacol.* 32(3):410-416
Balzarini (1993) *J. Biol. Chem.* 268(9):6332-6337
Balzarini (1995) *FEBS Lett.* 373(1):41-44
Balzarini, J. et al. (1996) *Proc. Natl. Acad. Sci. USA* 93:7295-7299
Banerjee, D. et al. (1995) *Acta Biochim. Pol.* 42:457-464
Banerjee, D. et al. (1998) *Cancer Res.* 58:4292-4296
Barbato, et al. (1989) *Nucleosides Nucleotides* 8(4):515-528
Barr, P. J. and Robins, M. J. (1981) *J. Med. Chem.* 24(12):1385-1388
Barr, P. J. et al. (1983) *Biochemistry* 22:1696-1703
Barrett, J. E. et al. (1998) *J. Am. Chem. Soc.* 120:449-450
Bathe (1999) *Cancer J. Sci. Am.* 5(1):34-40
Bergstrom, D. E. et al. (1981) *J. Org. Chem.* 46(7):1432-1441
Bergstrom, D. E. et al. (1984) *J. Med. Chem.* 27:279-284
Bertino, J. R. et al. (1996) *Stem Cells* 14:5
Bible, K. C. et al. (1997) *Cancer Res.* 57(16):3375-80
Bigge, et al. (1980) *J. Amer. Chem. Soc.* 102:2033-2038
Carreras, C. W. and Santi, D. V. (1995) *Annu. Rev. Biochem.* 64:721-762
Carson, D. A. and Haneji, N. (1999) *Nature Medicine* 5(7):731-732
Carter, P. et al. (1992) *Proc. Natl. Acad. Sci. USA* 89:4285-4289
Cass, et al. (1998) *Biochem. Cell Biol.* 76(5):761-770
Catucci, M. et al. (1999) *J. Acquir. Immune Defic. Syndr.* 21:203-208
Chaudhuri, N. C. et al. (1995) *J. Am. Chem. Soc.* 117:10434-10442
Chen, L. et al. (1996) *Cancer Res.* 56:1331-1340
Cho, Y. M. et al. (1994) *Tetrahedron Lett.* 35:1149-1152
Chou, T. C. and Talalay, P. (1984) *Adv. Enzyme Regul.* 22:27-55
Clayman, G. L. (2000) *Semin Oncol* 27(4 Suppl 8):39-43
Copur, S. et al. (1995) *Biochem. Pharm.* 49(10):1419-1426
Cordon-Cardo, C. and Prives, C. (1999) *J. Exp. Med.* 190(10):1367-1370
Costi, et al. (1999) *J. Med. Chem.* 42(12):2112-2124
Crisp, G. T. (1989) *Synth. Commun.* 19:2117-2123
Curt (1996) *Oncologist* 1 (3):II-III
Dale, et al. (1973) *Proc. Natl. Acad. Sci. USA* 70:2238-2242
DeClercq, E. et al. (1978) *Proc. Intl. Chemo.* 1(1):352-354
DeClercq, E. et al. (1983) *J. Med. Chem.* 26:661-666
DeClercq, E. et al. (1994) *Nucl. And Nucleotides* 13(687):1271-1295
DeClercq, E. et al. (1997) *Clin. Micro. Review* 10(4):674-693
DiCiommo et al. (2000) *Cancer Biology* 10:255-269
Dorr, R. T. and Von Hoff, D. D., eds. (1994) "Cancer Chemotherapy Handbook" 2nd ed. (Appleton and Lange), pp. 768-773
Drake, et al. (1996) *Biochem. Pharmcol.* 51(10):1349-1355
Elliott et al. (1994) *Lancet* 344(8930):1105-1110
Feldmann et al. (1998) *Springer Semin. Immunopath.* 20(1-2):211-228
Felmingham and Washington (1999) *J. Chemother.* 11 Suppl 1:5-21
Grem, J. L. (1992) *Semin Oncol.* 19(2 Suppl 3):56-65.
Goodwin, J. T. et al. (1993) *Tetrahedron Lett.* 34:5549-5552
Graham, D. et al. (1998) *J. Chem. Soc. Perkin Trans.* 1:1131-1138
Guevara, N. V. et al. (1999) *Nat Med* 5(3):335-9
Han et al. (1999) *Arthritis Rheum* 42(6):1088-92
Haskell, C. M. ed., (1995) *Cancer Treatment* 4th Ed., W. B. Saunders Co., Philadelphia, Pa.
Hobbs, F. W. Jr. (1989) *J. Org. Chem.* 54:3420-3422
Holy, et al. (1999) *J. Med. Chem.* 42(12):2064-2086
Hong, T. M. et al. (2000) *Am. J. Respir. Cell. Mol. Biol.* 23(3):355-63
Hooker, et al. (1996) *J. Virol.* 70(10):8010-8018
Houze, T. A. (1997) *Tumour Biol.* 18:53-68
Hsiao, L. Y. et al. (1981) *J. Med. Chem.* 24:887-889
Hudson, J. D. et al. (1999) *J. Exp. Med.* 190:1375-1382
Hudziak, R. M. et al. (1988) *Proc. Natl. Acad. Sci. USA* 85:5102-6
Iglesias, M. et al (1998) *Oncogene* 17:1195-1205
Inazuka, M. (2000) *Rheumatology (Oxford)* 39(3):262-6
Jackman, A. L. (1995) *Ann. Oncol.* 6(9):871-881
Jackman, A. L. et al. (1995b) *Anticancer Drug Des.* 10:573
Jin, S. et al. (2000) *Oncogene* 19:4050-7
Johnston, et al. (1994) *J. Clin. Oncol.* 12:2640-2647
Johnston, et al. (1995) *Cancer Res.* 55:1407-1412
Jones, R. G and Mann, M. J. (1953) *J. Am. Cancer Soc.* 75:4048-4052
Kashani-Sabet et al. (1988) *Cancer Res.* 48:5775-5778
Kitasato, H. et al. (2000) *Arthritis Rheum.* 43(2):469-70
Knudson, A. G. (1993) *Proc. Natl. Acad. Sci. USA* 90(23):10914-21
Kobayashi, H. et al. (1995) *Japan. J. Cancer Res.* 86:1014-1018
Komaki (1995) *Breast Cancer Res. Treat.* 35(2):157-162
Krajewskas and Shugar (1982) *Biochem. Pharmacol.* 31(6):1097-1102
Kullmann, F. et al. (1999) *Arthritis Rheum.* 42(8): 1594-600
Kwong, A. D. et al. (1999) *Antiviral Res.* 41:67-84
Lang, S. M. et al (1999) *Gut.* 44:822-825
Larsson (1996) *Acta. Oncol.* 35(4):469-472
Lasic, D. D. (1996) *Nature* 380:561-562
Leichman (1998) *Oncol.* 12(8Suppl.6):43-47
Lenz (1995) *PCR Methods Appl.* 4:305-308
Lenz, H. J. et al. (1998) *Clin. Cancer Res.* 4:1227-1234
Less, A. et al. (1998) *Bio. Structure and Dynamics* 15(4):703-715
Lewis, J. G. et al. (1996) *Proc. Natl. Acad. Sci. USA* 93:3176-3181

Lewis (1993) *Cancer Immural Immunother.* 37(4):255-263
Li, W. et al.(1995) *Proc. Natl. Acad. Sci.* 92:10436-40
Lin, W. Y et al. (1997) *Eur. J. Nucl. Med.* 24:590-595
Livak, K. J. et al. (1992) *Nucleic Acids Res.* 20:4831-4837
Lönn, U. et al. (1996) *Cancer* 77(1): 107-112
Mahalingam, B. et al. (1999) *Eur. J. Biochem.* 263:23844-245
Malfait, A. M. et al. (2000) *Proc. Natl. Acad. Sci.* 97(17): 9561-9566
Marinova-Mutafchieva, L. et al.(2000) *Arthritis and Rheumatism* 43(3):638-644
Masciullo, V. et al. (2000) *Int. J. Oncol.* 17(5):897-902
McGuigan, C. (1993) *J. Med. Chem.* 36:1048-1052
McGuigan, C. (1996) *J. Med. Chem.* 39:1748-1753
McGuigan, C. et al. (1994) *FEBS Lett.* 351:11-14
Miller, E. J. et al. (1972) *Biochemistry* 11:4903-4909
Miller, J. H. "A short course in bacterial genetics: A laboratory manual and handbook for *E. coli* and related bacteria" Cold Spring Harbor Press (1992)
Miotla, J. et al. (2000) *Laboratory Investigation* 80(8): 1195-1205
Morgan, A. S. et al. (1998) *Cancer Res.* 58:2568-2575
Mountz, J. D. et al. (1994) *Arthritis & Rheumatism* 37(10): 1415-1420
Mulder (1994) *Anticancer Res.* 14(6B):2677-2680
Murray, B. E. (1997) *Adv. Int. Med.* 42:339-367
Negishi, et al. (1996) *Nuc. Acids Symp.* 35:137-138
Palmer, S. et al. (1999) *AIDS* 13(6): 661-667
Paradiso, A. et al. (2000) *Br. J. Cancer* 82(3):560-567
Patterson, et al. (1998) *Cancer Res.* 58:2737-2740
Pederson-Lane, J. (1997) *Protein Expression and Purification* 10:256-262
Pegram, M. D. et al. (1997) *Oncogene* 15:537-547
Pegram, M. D. et al. (1999) *Oncogene* 18(13):2241-51
Phelps, M. E. et al. (1980) *J. Med. Chem.* 23:1229-1232
Plath, T. et al. (2000) *J. Cell. Biol.* 150(6): 1467-78
Pluta, et al. (1999) *Boll. Chim. Farm.* 138(1):30-33
Portwine, C. (2000) *Pediatr. Res.* 47(5)573
Roberts (1966) *Biochem.* 5(11) 3546-3548
Robins, et al. (1981) *Tetrahedron Lett.* 22:421-424
Robins, et al. (1982) *Can. J. Chem.* 60:554-557
Robins, M. J. et al. (1983) *J. Org. Chem.* 48:1854-1862
Ruth, J. L. et al. (1978) *J. Org. Chem.* 43:2870-2876
Santi, D. V. (1980) *J. Med. Chem.* 23:103-111
Schaechter, M. et al., eds. (1993) *Mechanisms of Microbial Disease,* 2$^{nd}$ Ed., Williams and Wilkins
Shafer, R. W. and Vuitton, D. A. (1999) *Biomed. Pharamcother.* 53:73-86
Shepard, H. M. et al. (1988) *J. Clin. Immunol.* 8:333-341
Shepard, H. M. (1991) *J. Clin. Immunol.* 11(3):117-127
Shim, J. et al. (2000) *J. Biol. Chem.* 275(19):14107-14111
Simon, L. S. (2000) *Int. J. Clin. Pract.* 54(4):243-249
Simon, S. M. and Schindler, M. (1994) *Proc. Natl. Acad. Sci. USA* 91:3497
Smith, et al. (1985) *J. Natl. Cancer Inst.* 74(2):341-347
Smith, et al. (1990) *Cancer Res.* 50(10):2943-2948
Smith, et al. (1995) *Phil. Trans. Royal Soc. Lond. B* 347:49-56
Spector, D. L. et al. (1998) Cells, A Laboratory Manual, Vols I to III, Cold Spring Harbor Press
Stout (1999) *Biochemistry* 38(5):1607-17
Stühlinger, M. et al. (1994) *J. Steroid Biochem. Mol. Biol.* 49:39-42
Sun, Y. et al. (2000) *J. Biol. Chem.* 275(15):11327-32
Tak, P. P. et al. (2000) *Immunol. Today* 21(2):78-82
Tanaka, K. et al. (1999) *Circulation* 99(13):1656-1659
Tannock, I. F. (1996) *J. Clin. Oncol.* 14(12):3156-3174
Tolstikov, V. V. et al. (1997) *Nucleosides & Nucleotides* 16:215-225
Touroutoglou and Pazdur (1996) *Clin. Cancer Res.* 2(2):227-243
Tsavaris, N. et al. (1990) *J. Chemother.* 2(2):123-126
Troutner, D. A. (1987) *Nucl. Med. Biol.* 14:171-176
Turner, B. G. and Summers, M. F. (1999) *J. Mol. Biol.* 285: 1-32
van Laar (1996) *Clin. Cancer Res.* 2(8):1327-1333
van Triest (1999) *Clin. Cancer. Res.* 5(3):643-54
Wallis, et al. (1999) *Il Farmaco* 54(1-2):83-89
Wang, Q. M. (1999) *Prog. Drug Res.* 52:197-219
Wataya, Y. (1979) *J. Med. Chem.* 22:339-340
Weinberg, R. A. (1995) *Ann. NY Acad. Sci.* 758:331-8
Wettergren, Y. et al. (1994) *Mol. Genet.* 20:267-285
Whalen and Boyer (1998) *Semin. Liver Dis.* 18(4):345-358
Wilson, J. D. et al. (eds.) "Harrison's Principles of Internal Medicine" 12$^{th}$ ed., McGraw-Hill, Inc., pp. 21-76 (1991)
Wright, A. M. et al. (2000) *Leukemia.* 14(1):52-60
Wolff, B. and Naumann, M. (1999) *Oncogene* 18:2663-2666
Zeid, et al. (1999) *Nucleosides & Nucleotides* 18(1):95-111
Zhang, L. et al. (2000) *Cancer Research* 60:3655-3661

What is claimed is:

1. A compound or its pharmaceutically acceptable salt, ester or ether, wherein the compound has the formula:

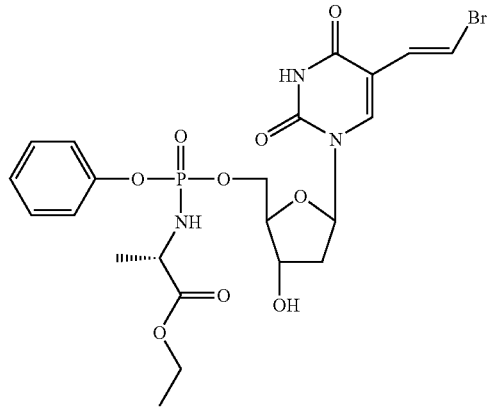

wherein the sugar moiety is 2'-deoxy-β-D-ribofuranosyl.

2. A compound or its pharmaceutically acceptable salt, ester or ether, wherein the compound has the formula:

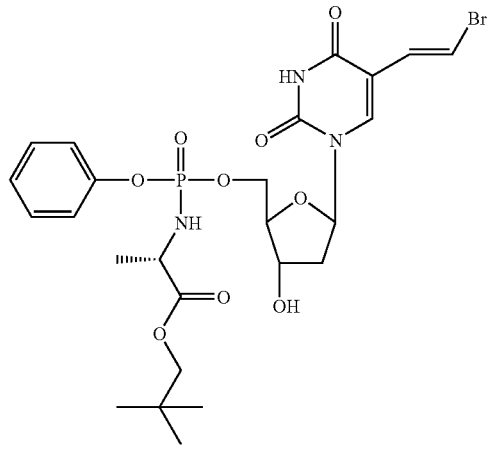

wherein the sugar moiety is 2'-deoxy-β-D-ribofuranosyl.

3. A compound or its pharmaceutically acceptable salt, ester or ether, wherein the compound has the formula:

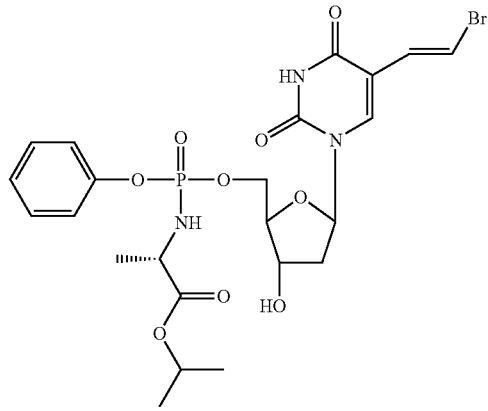

wherein the sugar moiety is 2'-deoxy-β-D-ribofuranosyl.

4. A compound or its pharmaceutically acceptable salt, ester or ether, wherein the compound has the formula:

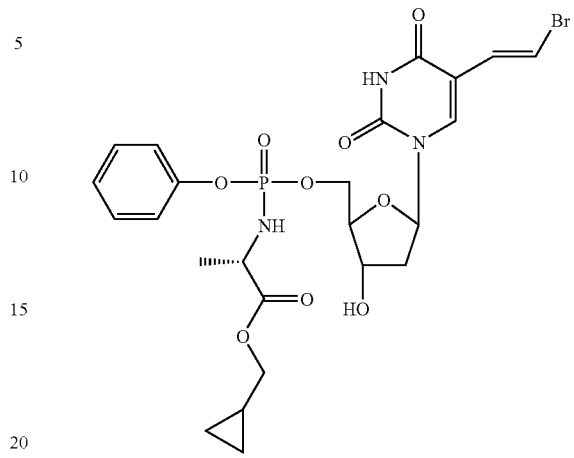

wherein the sugar moiety is 2'-deoxy-β-D-ribofuranosyl.

5. A compound or its pharmaceutically acceptable salt, ester or ether, wherein the compound has the formula:

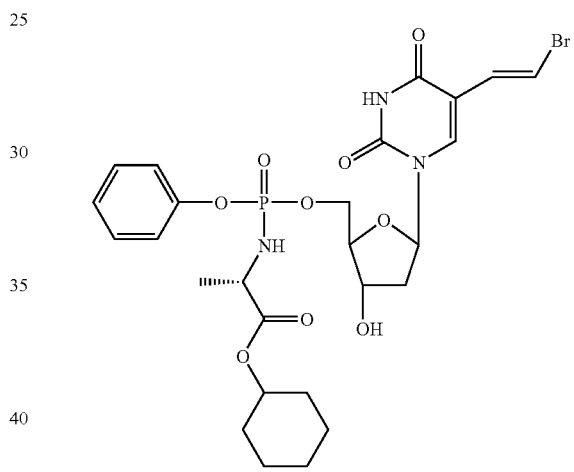

wherein the sugar moiety is 2'-deoxy-β-D-ribofuranosyl.

6. A compound or its pharmaceutically acceptable salt, ester or ether, wherein the compound has the formula:

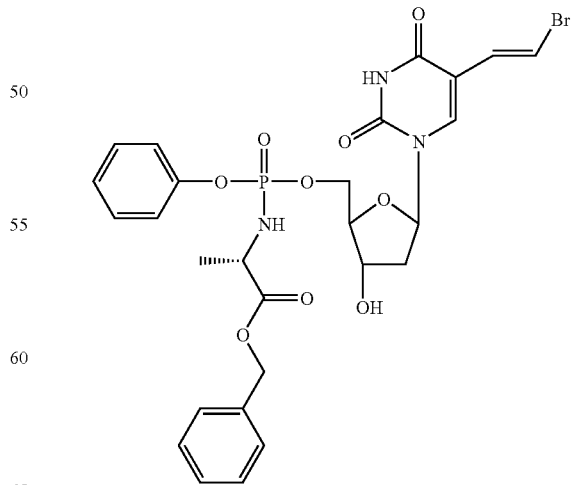

wherein the sugar moiety is 2'-deoxy-β-D-ribofuranosyl.

7. A compound or its pharmaceutically acceptable salt, ester or ether, wherein the compound has the formula:

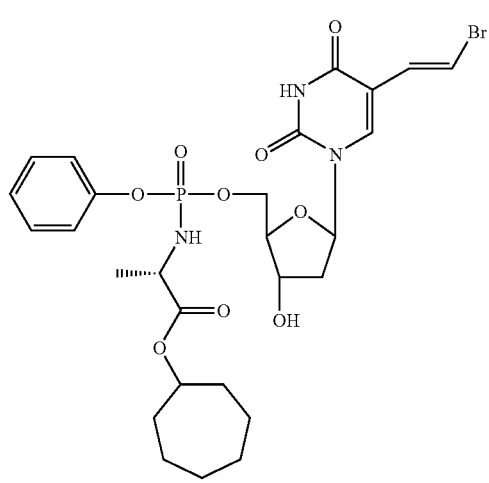

wherein the sugar moiety is 2'-deoxy-β-D-ribofuranosyl.

8. A compound or its pharmaceutically acceptable salt, ester or ether, wherein the compound has the formula:

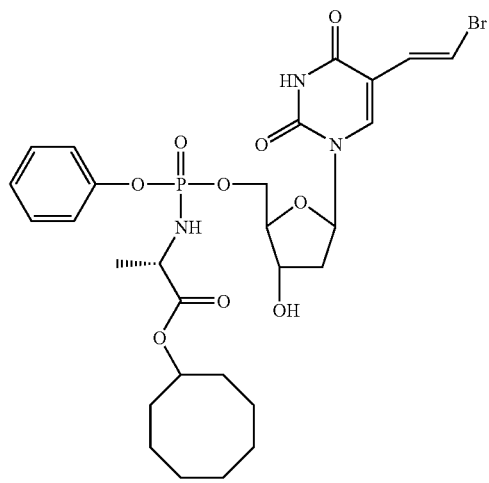

wherein the sugar moiety is 2'-deoxy-β-D-ribofuranosyl.

9. A compound or its pharmaceutically acceptable salt, ester or ether, wherein the compound has the formula:

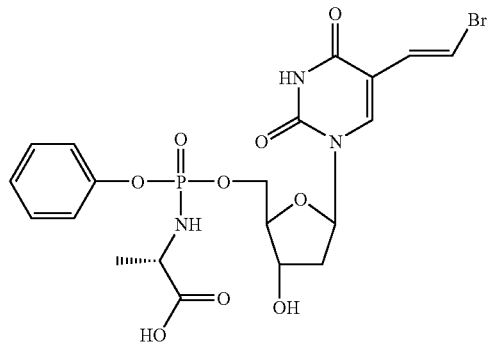

wherein the sugar moiety is 2'-deoxy-β-D-ribofuranosyl.

10. A compound or its pharmaceutically acceptable salt, ester or ether, wherein the compound has the formula:

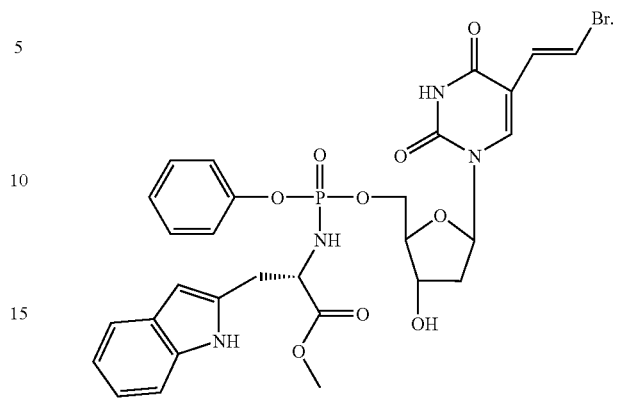

wherein the sugar moiety is 2'-deoxy-β-D-ribofuranosyl.

11. A compound or its pharmaceutically acceptable salt, ester or ether, wherein the compound has the formula:

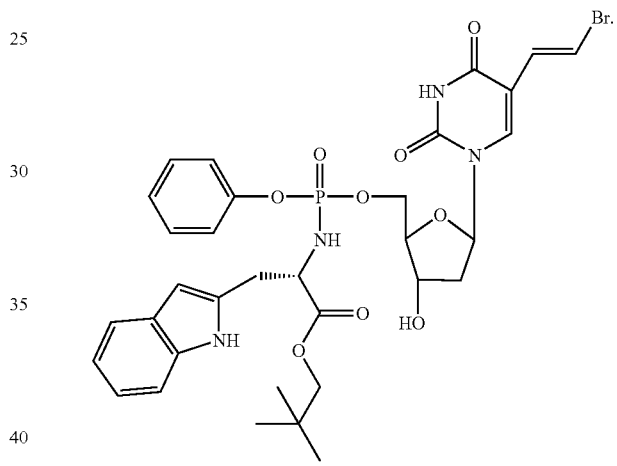

wherein the sugar moiety is 2'-deoxy-β-D-ribofuranosyl.

12. A compound or its pharmaceutically acceptable salt, ester or ether, wherein the compound has the formula:

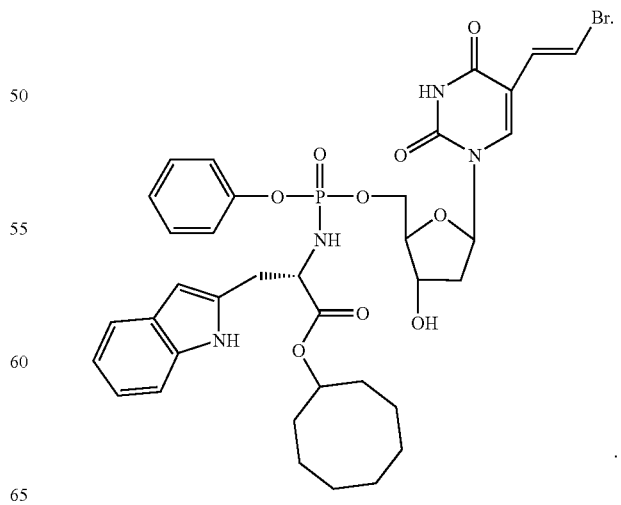

wherein the sugar moiety is 2'-deoxy-β-D-ribofuranosyl.

13. A compound or its pharmaceutically acceptable salt, ester or ether, wherein the compound has the formula:

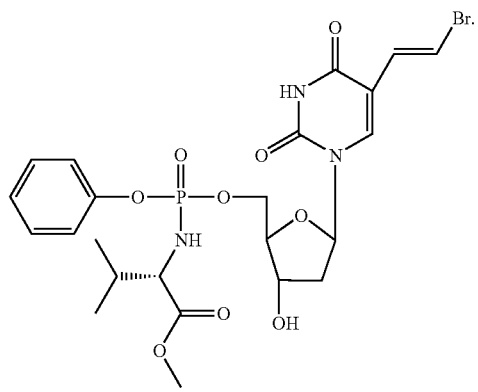

wherein the sugar moiety is 2'-deoxy-β-D-ribofuranosyl.

14. A compound or its pharmaceutically acceptable salt, ester or ether, wherein the compound has the formula:

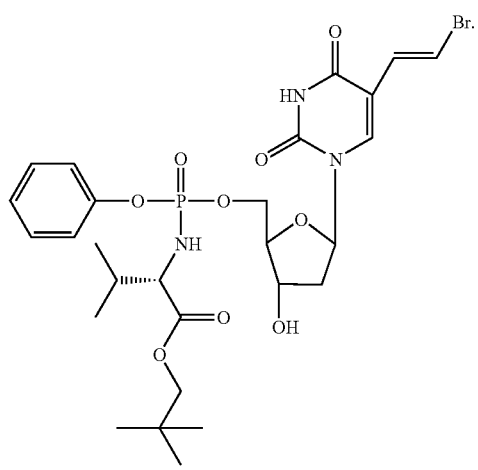

wherein the sugar moiety is 2'-deoxy-β-D-ribofuranosyl.

15. A compound or its pharmaceutically acceptable salt, ester or ether, wherein the compound has the formula:

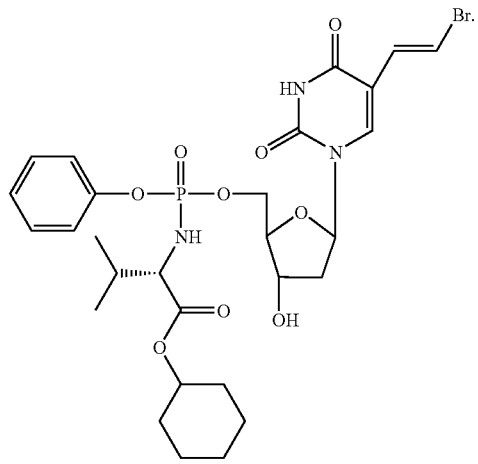

wherein the sugar moiety is 2'-deoxy-β-D-ribofuranosyl.

16. A compound or its pharmaceutically acceptable salt, ester or ether, wherein the compound has the formula:

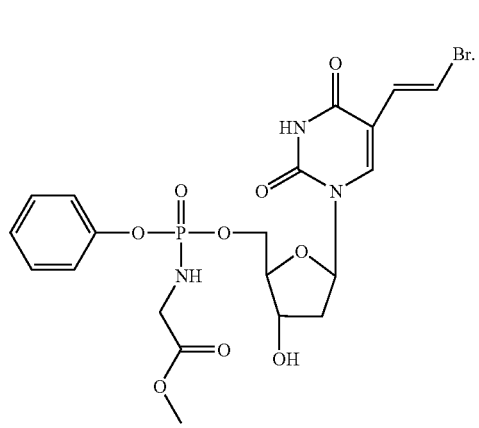

wherein the sugar moiety is 2'-deoxy-β-D-ribofuranosyl.

17. A compound or its pharmaceutically acceptable salt, ester or ether, wherein the compound has the formula:

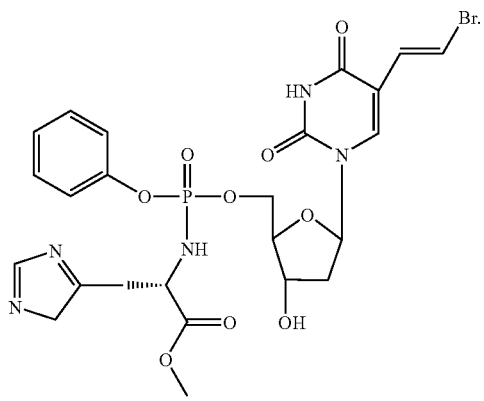

wherein the sugar moiety is 2'-deoxy-β-D-ribofuranosyl.

18. A compound or its pharmaceutically acceptable salt, ester or ether, wherein the compound has the formula:

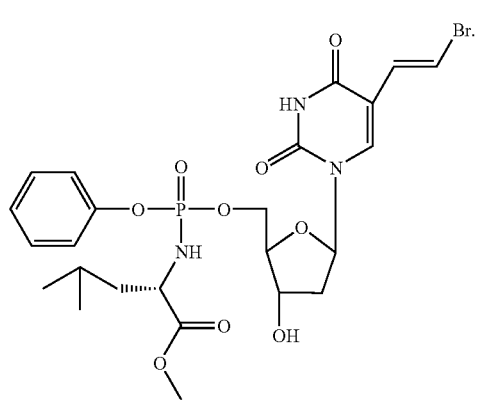

wherein the sugar moiety is 2'-deoxy-β-D-ribofuranosyl.

19. A compound or its pharmaceutically acceptable salt, ester or ether, wherein the compound has the formula:

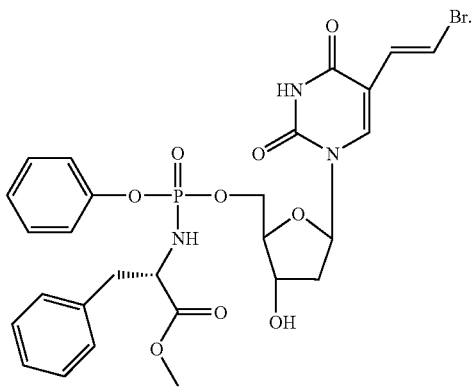

wherein the sugar moiety is 2'-deoxy-β-D-ribofuranosyl.

20. A compound or its pharmaceutically acceptable salt, ester or ether, wherein the compound has the formula:

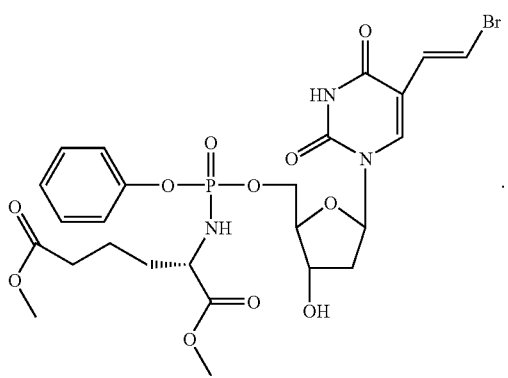

wherein the sugar moiety is 2'-deoxy-β-D-ribofuranosyl.

21. A composition comprising the compound of any of claims 1-20 and a carrier.

22. A pharmaceutical composition comprising the compound of any of claims 1-20 and a pharmaceutically acceptable carrier.

23. A method of inhibiting the proliferation of a cell that endogenously overexpresses thymidylate synthase, and wherein said cell is selected from the group consisting of a breast cancer cell, a hepatoma cell, a bone cancer cell, a a brain cancer cell, a liver cancer cell, a pancreatic cancer cell, a esophageal cancer cell, a bladder cancer cell, a gastrointestinal cancer cell, an ovarian cancer cell, a skin cancer cell, a prostate cancer cell, a gastric cancer cell, a colon cancer cell, and a lung cancer cell, comprising contacting the cell with an effective amount of the compound of any of claims 1-20.

24. A method for treating a patient suffering from rheumatoid arthritis, comprising administering to the patient an effective amount of the compound of any of claims 1-20.

25. The method of claim 23, wherein the contacting is in vitro.

26. The method of claim 23, wherein the contacting is in vivo.

27. A method of a patient suffering from a cancer selected from the group consisting of breast cancer, hepatoma, liver cancer, pancreatic cancer, bone cancer, brain cancer, esophageal cancer, bladder cancer, gastrointestinal cancer, ovarian cancer, skin cancer, prostate cancer, gastric cancer, colon cancer, and lung cancer cell and wherein the cell or tissue of the cancer endogenously overexpresses thymidylate synthase, comprising administering to the patient an effective amount of a compound of any of claims 1-20.

28. The method of claim 27, wherein the cancer is breast cancer or colon cancer.

* * * * *

UNITED STATES PATENT AND TRADEMARK OFFICE
CERTIFICATE OF CORRECTION

PATENT NO. : 7,462,605 B2  Page 1 of 1
APPLICATION NO. : 10/119927
DATED : December 9, 2008
INVENTOR(S) : Shepard et al.

It is certified that error appears in the above-identified patent and that said Letters Patent is hereby corrected as shown below:

At column 86, line 27, replace "A method of a patient" with -- A method of treating a patient --

Signed and Sealed this

Seventeenth Day of November, 2009

David J. Kappos
*Director of the United States Patent and Trademark Office*

SEQUENCE LISTING

```
<160> NUMBER OF SEQ ID NOS: 6

<210> SEQ ID NO 1
<211> LENGTH: 19
<212> TYPE: DNA
<213> ORGANISM: Homo sapiens

<400> SEQUENCE: 1
gggcagatcc aacacatcc                                          19
```

```
<210> SEQ ID NO 2
<211> LENGTH: 20
<212> TYPE: DNA
<213> ORGANISM: Homo sapiens

<400> SEQUENCE: 2
ggtcaactcc ctgtcctgaa                                              20

<210> SEQ ID NO 3
<211> LENGTH: 19
<212> TYPE: DNA
<213> ORGANISM: Homo sapiens

<400> SEQUENCE: 3
gccaacacag tgctgtctg                                               19

<210> SEQ ID NO 4
<211> LENGTH: 19
<212> TYPE: DNA
<213> ORGANISM: Homo sapiens

<400> SEQUENCE: 4
ctcctgcttg ctgatccac                                               19

<210> SEQ ID NO 5
<211> LENGTH: 26
<212> TYPE: DNA
<213> ORGANISM: Homo sapiens

<400> SEQUENCE: 5
cggaagcttg agccgcgtcc gccgca                                       26

<210> SEQ ID NO 6
<211> LENGTH: 26
<212> TYPE: DNA
<213> ORGANISM: Homo sapiens

<400> SEQUENCE: 6
gaaggtaccc taaacagcca tttcca                                       26
```